United States Patent
Kato et al.

(10) Patent No.: US 8,124,091 B2
(45) Date of Patent: Feb. 28, 2012

(54) HUMAN MONOCLONAL ANTIBODIES TO INFLUENZA M2 PROTEIN AND METHODS OF MAKING AND USING SAME

(75) Inventors: Shinichiro Kato, Chiba (JP); Rongfang Wang, Shanghai (CN)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 675 days.

(21) Appl. No.: 11/577,695

(22) PCT Filed: Dec. 5, 2005

(86) PCT No.: PCT/IB2005/004146
§ 371 (c)(1),
(2), (4) Date: Nov. 24, 2008

(87) PCT Pub. No.: WO2006/061723
PCT Pub. Date: Jun. 15, 2006

(65) Prior Publication Data
US 2009/0196872 A1    Aug. 6, 2009

Related U.S. Application Data

(60) Provisional application No. 60/633,846, filed on Dec. 6, 2004, provisional application No. 60/724,198, filed on Oct. 6, 2005.

(51) Int. Cl.
*A61K 39/42*    (2006.01)

(52) U.S. Cl. ............... 424/147.1; 424/139.1; 424/159.1; 424/186.1; 435/325; 435/331; 435/339

(58) Field of Classification Search ........................ None
See application file for complete search history.

(56) References Cited

U.S. PATENT DOCUMENTS
2003/0219442 A1 * 11/2003 Mikayama et al. ........ 424/159.1

FOREIGN PATENT DOCUMENTS
WO          99/07839 A2    2/1999
(Continued)

OTHER PUBLICATIONS

Liu, W., et al., Monoclonal Antibodies Recognizing EVETPIRN Epitope of Influenza A Virus M2 Protein Could Protect Mice From Lethal Influenza A Virus Challenge, Immunology Letters, 93:131-136 (2004).

(Continued)

*Primary Examiner* — Benjamin P Blumel
(74) *Attorney, Agent, or Firm* — Pillsbury Winthrop Shaw Pittman LLP

(57) ABSTRACT

Human, humanized and chimeric monoclonal antibodies that bind to influenza M2 protein. A human monoclonal antibody that binds to influenza M2 protein having different amino acid sequences. The antibodies are useful for, among other things, treatment, diagnostics, purifying and isolating M2 or influenza virus, and identifying the presence of M2 or influenza virus in a sample or a subject.

56 Claims, 7 Drawing Sheets

FOREIGN PATENT DOCUMENTS

WO 99/28478 A1 6/1999
WO 03/078600 A2 9/2003

OTHER PUBLICATIONS

Zou, P., et al., The Epitope Recognized by a Monoclonal Antibody in Influenza A Virus M2 Protein is Immunogenic and Confers Immune Protection, International Immunopharmacology, 5:631-635 (2005).

Lamb, R.A., et al., Influenza Virus M2 Protein is an Integral Membrane Protein Expressed on the Infected-Cell Surface, Cell, 1985, 627-633, 40.

Wang, Rongfang, et al, "Therapeutic potential of a fully human monoclonal antibody against influenza A virus M2 protein", Antiviral Research, 2008, 80:168-177.

* cited by examiner

Figure 6  Z3G1 antibody protects mice from a lethal dose of A/HK/1/68 challenge in the NK cell depleted condition.
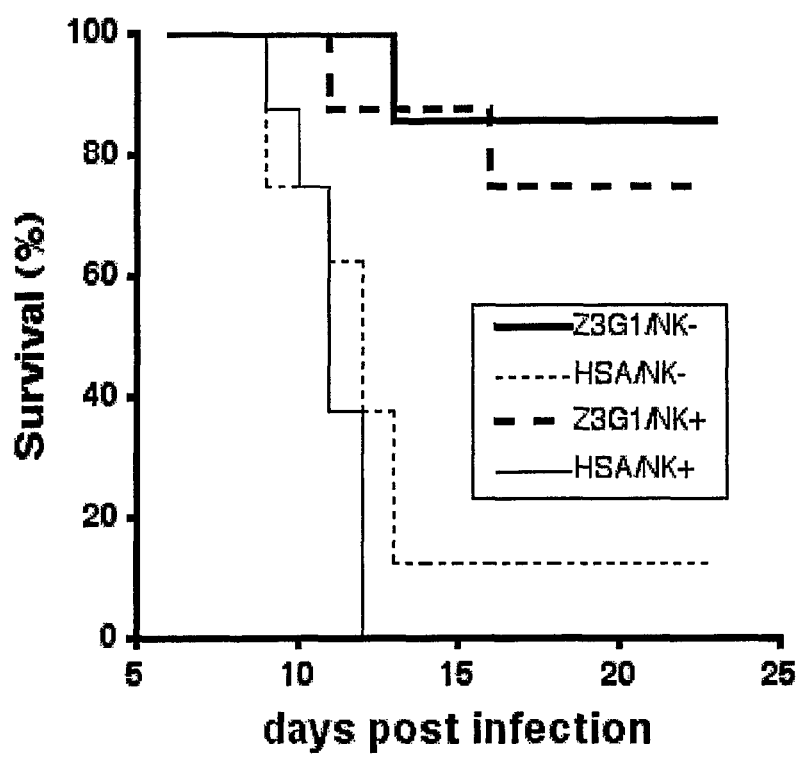

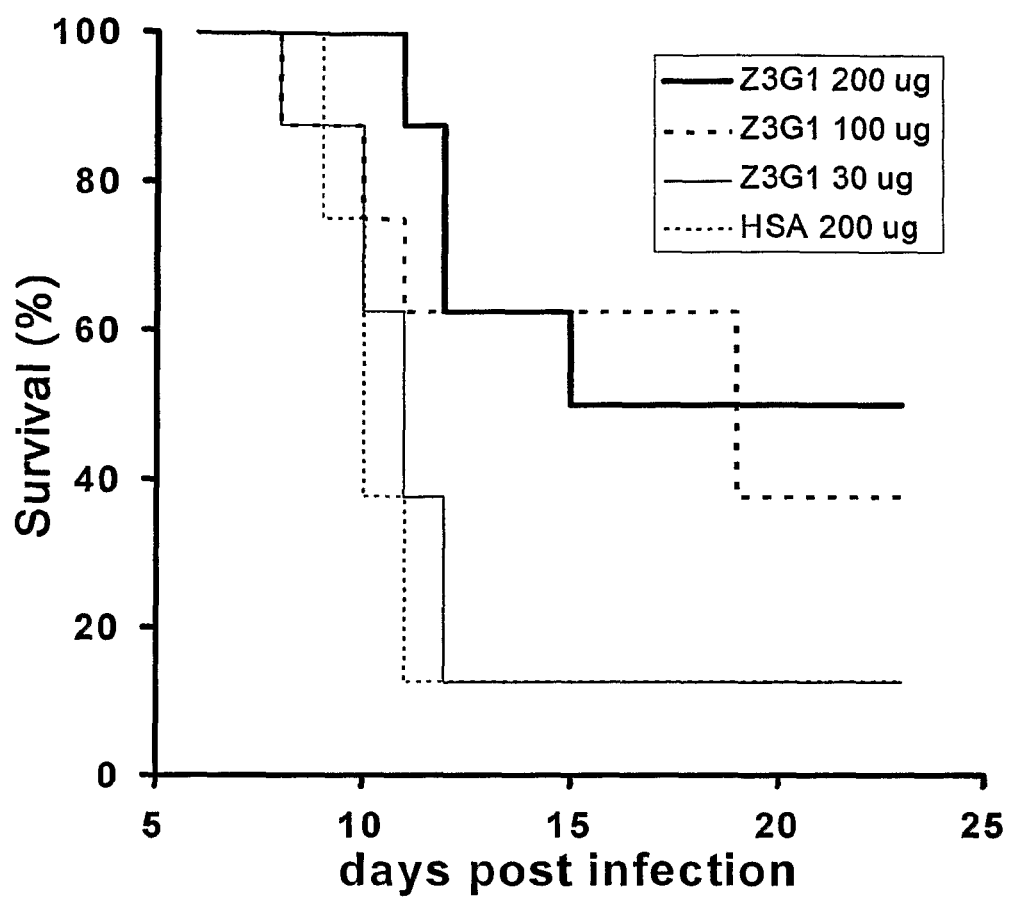
Figure 7 Z3G1 antibody protects mice from a lethal dose of A/HK/1/68 challenge at a therapeutic regimen.

SEQUENCE LISTING

<160> NUMBER OF SEQ ID NOS: 75

<210> SEQ ID NO 1
<211> LENGTH: 10
<212> TYPE: PRT
<213> ORGANISM: Influenza virus

<400> SEQUENCE: 1

Leu Leu Thr Glu Val Glu Thr Pro Ile Arg
1               5                   10

<210> SEQ ID NO 2
<211> LENGTH: 23
<212> TYPE: PRT
<213> ORGANISM: Influenza virus

<400> SEQUENCE: 2

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 3
<211> LENGTH: 23
<212> TYPE: PRT
<213> ORGANISM: Influenza virus

<400> SEQUENCE: 3

Ser Leu Leu Thr Glu Val Glu Thr Pro Ile Arg Ser Glu Trp Gly Cys
1               5                   10                  15

Arg Cys Asn Asp Ser Gly Asp
            20

<210> SEQ ID NO 4
<211> LENGTH: 23
<212> TYPE: PRT
<213> ORGANISM: Influenza virus

<400> SEQUENCE: 4

Ser Leu Leu Thr Glu Val Glu Thr Pro Ile Arg Asn Glu Trp Glu Cys
1               5                   10                  15

Arg Cys Asn Gly Ser Ser Asp
            20

<210> SEQ ID NO 5
<211> LENGTH: 23
<212> TYPE: PRT
<213> ORGANISM: Influenza virus

<400> SEQUENCE: 5

Ser Leu Pro Thr Glu Val Glu Thr Pro Ile Arg Asn Glu Trp Gly Cys
1               5                   10                  15

Arg Cys Asn Asp Ser Ser Asp
            20

<210> SEQ ID NO 6
<211> LENGTH: 23
<212> TYPE: PRT
<213> ORGANISM: Influenza virus

<400> SEQUENCE: 6

Ser Leu Leu Thr Glu Val Glu Thr Pro Ile Arg Asn Glu Trp Gly Cys

```
1               5                   10                  15
Arg Cys Asn Gly Ser Ser Asp
            20

<210> SEQ ID NO 7
<211> LENGTH: 23
<212> TYPE: PRT
<213> ORGANISM: Influenza virus

<400> SEQUENCE: 7

Ser Leu Leu Thr Glu Val Asp Thr Leu Thr Arg Asn Gly Trp Gly Cys
1               5                   10                  15

Arg Cys Ser Asp Ser Ser Asp
            20

<210> SEQ ID NO 8
<211> LENGTH: 23
<212> TYPE: PRT
<213> ORGANISM: Influenza virus

<400> SEQUENCE: 8

Ser Leu Leu Thr Glu Val Glu Thr Pro Ile Arg Lys Glu Trp Gly Cys
1               5                   10                  15

Asn Cys Ser Asp Ser Ser Asp
            20

<210> SEQ ID NO 9
<211> LENGTH: 23
<212> TYPE: PRT
<213> ORGANISM: Influenza virus

<400> SEQUENCE: 9

Ser Leu Leu Thr Glu Val Glu Thr Leu Ile Arg Asn Gly Trp Gly Cys
1               5                   10                  15

Arg Cys Ser Asp Ser Ser Asp
            20

<210> SEQ ID NO 10
<211> LENGTH: 23
<212> TYPE: PRT
<213> ORGANISM: Influenza virus

<400> SEQUENCE: 10

Ser Leu Leu Thr Glu Val Glu Thr Leu Thr Lys Asn Gly Trp Gly Cys
1               5                   10                  15

Arg Cys Ser Asp Ser Ser Asp
            20

<210> SEQ ID NO 11
<211> LENGTH: 23
<212> TYPE: PRT
<213> ORGANISM: Influenza virus

<400> SEQUENCE: 11

Ser Leu Leu Thr Glu Val Glu Thr Pro Ile Arg Ser Glu Trp Gly Cys
1               5                   10                  15

Arg Tyr Asn Asp Ser Ser Asp
            20

<210> SEQ ID NO 12
<211> LENGTH: 23
<212> TYPE: PRT
<213> ORGANISM: Influenza virus
```

<400> SEQUENCE: 12

Ser Leu Leu Thr Glu Val Glu Thr Pro Thr Arg Asn Gly Trp Glu Cys
1               5                   10                  15

Lys Cys Ser Asp Ser Ser Asp
            20

<210> SEQ ID NO 13
<211> LENGTH: 23
<212> TYPE: PRT
<213> ORGANISM: Influenza virus

<400> SEQUENCE: 13

Ser Leu Leu Thr Glu Val Glu Thr His Thr Arg Asn Gly Trp Glu Cys
1               5                   10                  15

Lys Cys Ser Asp Ser Ser Asp
            20

<210> SEQ ID NO 14
<211> LENGTH: 23
<212> TYPE: PRT
<213> ORGANISM: Influenza virus

<400> SEQUENCE: 14

Ser Leu Leu Thr Glu Val Lys Thr Pro Thr Arg Asn Gly Trp Glu Cys
1               5                   10                  15

Lys Cys Ser Asp Ser Ser Asp
            20

<210> SEQ ID NO 15
<211> LENGTH: 23
<212> TYPE: PRT
<213> ORGANISM: Influenza virus

<400> SEQUENCE: 15

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 16
<211> LENGTH: 23
<212> TYPE: PRT
<213> ORGANISM: Influenza virus

<400> SEQUENCE: 16

Ser Leu Leu Thr Glu Val Glu Thr Pro Thr Arg Asp Gly Trp Glu Cys
1               5                   10                  15

Lys Cys Ser Asp Ser Ser Asp
            20

<210> SEQ ID NO 17
<211> LENGTH: 23
<212> TYPE: PRT
<213> ORGANISM: Influenza virus

<400> SEQUENCE: 17

Ser Leu Leu Thr Glu Val Glu Thr Pro Thr Arg Asn Gly Trp Gly Cys
1               5                   10                  15

Arg Cys Ser Asp Ser Ser Asp
            20

-continued

```
<210> SEQ ID NO 18
<211> LENGTH: 23
<212> TYPE: PRT
<213> ORGANISM: Influenza virus

<400> SEQUENCE: 18

Ser Leu Leu Thr Glu Val Glu Thr Pro Thr Arg Asn Gly Trp Glu Cys
1               5                   10                  15

Lys Cys Asn Asp Ser Ser Asp
            20

<210> SEQ ID NO 19
<211> LENGTH: 23
<212> TYPE: PRT
<213> ORGANISM: Influenza virus

<400> SEQUENCE: 19

Ser Leu Leu Thr Glu Val Glu Thr Leu Thr Arg Asn Gly Trp Glu Cys
1               5                   10                  15

Lys Cys Ser Asp Ser Ser Asp
            20

<210> SEQ ID NO 20
<211> LENGTH: 23
<212> TYPE: PRT
<213> ORGANISM: Influenza virus

<400> SEQUENCE: 20

Ser Leu Leu Thr Glu Val Glu Thr Pro Ile Arg Asn Glu Trp Gly Cys
1               5                   10                  15

Lys Cys Asn Asp Ser Ser Asp
            20

<210> SEQ ID NO 21
<211> LENGTH: 23
<212> TYPE: PRT
<213> ORGANISM: Influenza virus

<400> SEQUENCE: 21

Ser Phe Leu Thr Glu Val Glu Thr Pro Ile Arg Asn Glu Trp Gly Cys
1               5                   10                  15

Arg Cys Asn Gly Ser Ser Asp
            20

<210> SEQ ID NO 22
<211> LENGTH: 23
<212> TYPE: PRT
<213> ORGANISM: Influenza virus

<400> SEQUENCE: 22

Ser Leu Leu Thr Glu Val Glu Thr Pro Thr Arg Asn Gly Trp Glu Cys
1               5                   10                  15

Arg Cys Asn Asp Ser Ser Asp
            20

<210> SEQ ID NO 23
<211> LENGTH: 23
<212> TYPE: PRT
<213> ORGANISM: Influenza virus

<400> SEQUENCE: 23

Ser Leu Leu Thr Glu Val Glu Thr Pro Ile Arg Lys Gly Trp Glu Cys
1               5                   10                  15
```

```
Asn Cys Ser Asp Ser Ser Asp
            20

<210> SEQ ID NO 24
<211> LENGTH: 23
<212> TYPE: PRT
<213> ORGANISM: Influenza virus

<400> SEQUENCE: 24

Ser Leu Leu Thr Glu Val Glu Thr Pro Thr Arg Asn Glu Trp Glu Cys
1               5                  10                  15

Arg Cys Ser Asp Ser Ser Asp
            20

<210> SEQ ID NO 25
<211> LENGTH: 23
<212> TYPE: PRT
<213> ORGANISM: Influenza virus

<400> SEQUENCE: 25

Ser Leu Leu Thr Gly Val Glu Thr His Thr Arg Asn Gly Trp Gly Cys
1               5                  10                  15

Lys Cys Ser Asp Ser Ser Asp
            20

<210> SEQ ID NO 26
<211> LENGTH: 23
<212> TYPE: PRT
<213> ORGANISM: Influenza virus

<400> SEQUENCE: 26

Ser Leu Leu Pro Glu Val Glu Thr His Thr Arg Asn Gly Trp Gly Cys
1               5                  10                  15

Arg Cys Ser Asp Ser Ser Asp
            20

<210> SEQ ID NO 27
<211> LENGTH: 8
<212> TYPE: PRT
<213> ORGANISM: Influenza virus

<400> SEQUENCE: 27

Leu Thr Glu Val Glu Thr Pro Ile
1               5

<210> SEQ ID NO 28
<211> LENGTH: 9
<212> TYPE: PRT
<213> ORGANISM: Influenza virus

<400> SEQUENCE: 28

Leu Leu Thr Glu Val Glu Thr Pro Ile
1               5

<210> SEQ ID NO 29
<211> LENGTH: 11
<212> TYPE: PRT
<213> ORGANISM: Influenza virus

<400> SEQUENCE: 29

Ser Leu Leu Thr Glu Val Glu Thr Pro Ile Arg
1               5                  10

<210> SEQ ID NO 30
```

<211> LENGTH: 11
<212> TYPE: PRT
<213> ORGANISM: Influenza virus

<400> SEQUENCE: 30

Leu Leu Thr Glu Val Glu Thr Pro Ile Arg Asn
1               5                   10

<210> SEQ ID NO 31
<211> LENGTH: 9
<212> TYPE: PRT
<213> ORGANISM: Influenza virus

<400> SEQUENCE: 31

Leu Thr Glu Val Glu Thr Pro Ile Arg
1               5

<210> SEQ ID NO 32
<211> LENGTH: 411
<212> TYPE: DNA
<213> ORGANISM: Homo sapiens

<400> SEQUENCE: 32
atggactgga cctggagcat ccttttcttg gtggcagcag caacaggtgc ccactcccag    60
gttcagctgg tgcagtctgg agctgaggtg aagaagcctg ggcctcagt gaaggtctcc    120 tgcaaggctt ctggttacac ctttaccagc tatggtatca gctgggtgcg acaggcccct    180
ggacaagggc ttgagtggat gggatggatc agcgcttaca atggtaacac aaactatgca    240
cagaagctcc agggcagagt caccatgacc acagacacat ccacgagcac agcctacatg    300
gagctgagga cctgagatc tgacgacacg gccgtgtatt actgtgcgag gcagcagct    360 ggcggatact ccagcactg gggccaggc accctggtca ccgtctcctc a              411

<210> SEQ ID NO 33
<211> LENGTH: 708
<212> TYPE: DNA
<213> ORGANISM: Homo sapiens

<400> SEQUENCE: 33
atggccagct ccctctcct cctcaccctc ctcactcact gtgcagggtc ctgggcccag    60
tctgtgctga ctcagccacc ctcagcgtct gggacccccg gcagagggt caccatctct    120 tgttctggaa gcaactccaa catcggaagt aaaactgtaa actggtacca gcagctccca    180
ggaacggccc ccaaactcct catctctagt aataatcagc ggccctcagg ggtccctgac    240
cgattctctg gctccaagtc tggcacctca gcctccctgg ccatcagtgg gctccagtct    300
gaggatgagg ctgattatta ctgtgcagca tgggatgaca gcctgaatgg tgtggtattc    360
ggcggaggga ccaagctgac cgtcctaggt cagcccaagg ctgcccctc ggtcactctg    420 ttcccaccct cctctgagga gcttcaagcc aacaaggcca cactggtgtg tctcataagt    480
gacttctacc cgggagccgt gacagtggcc tggaaggcag atagcagccc cgtcaaggcg    540
ggagtggaga ccaccacacc ctccaaacaa agcaacaaca gtacgcggc agcagctac    600 ctgagcctga cgcctgagca gtggaagtcc cacaaaagct acagctgcca ggtcacgcat    660
gaagggagca ccgtggagaa gacagtggcc cctacagaat gttcatag                708

<210> SEQ ID NO 34
<211> LENGTH: 137
<212> TYPE: PRT
<213> ORGANISM: Homo sapiens

```
<400> SEQUENCE: 34

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Ser Tyr Gly Ile Ser Trp Val Arg Gln Ala Pro Gly Gln Gly Leu
        50                  55                  60

Glu Trp Met Gly Trp Ile Ser Ala Tyr Asn Gly Asn Thr Asn Tyr Ala
65              70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ala Ala Ala Gly Gly Tyr Phe Gln His Trp Gly
        115                 120                 125

Gln Gly Thr Leu Val Thr Val Ser Ser
    130                 135

<210> SEQ ID NO 35
<211> LENGTH: 235
<212> TYPE: PRT
<213> ORGANISM: Homo sapiens

<400> SEQUENCE: 35

Met Ala Ser Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Asn Ser Asn Ile
            35                  40                  45

Gly Ser Lys Thr Val Asn Trp Tyr Gln Gln Leu Pro Gly Thr Ala Pro
        50                  55                  60

Lys Leu Leu Ile Ser Ser Asn Asn Gln Arg Pro Ser Gly Val Pro Asp
65              70                  75                  80

Arg Phe Ser Gly Ser Lys Ser Gly Thr Ser Ala Ser Leu Ala Ile Ser
                85                  90                  95

Gly Leu Gln Ser Glu Asp Glu Ala Asp Tyr Tyr Cys Ala Ala Trp Asp
            100                 105                 110

Asp Ser Leu Asn Gly Val Val Phe Gly Gly Gly Thr Lys Leu Thr Val
            115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
210                 215                 220

Val Glu Lys Thr Val Ala Pro Thr Glu Cys Ser
```

<210> SEQ ID NO 36
<211> LENGTH: 1404
<212> TYPE: DNA
<213> ORGANISM: Homo sapiens

<400> SEQUENCE: 36

```
atggactgga cctggagcat ccttttcttg gtggcagcag caacaggtgc ccactcccag      60
gttcagctgg tgcagtctgg agctgaggtg aagaagcctg gggcctcagt gaaggtctcc     120
tgcaaggctt ctggttacac ctttaccagc tatggtatca gctgggtgcg acaggcccct     180
ggacaagggc ttgagtggat gggatggatc agcgcttaca atggtaacac aaactatgca     240
cagaagctcc agggcagagt caccatgacc acagacacat ccacgagcac agcctacatg     300
gagctgagga gcctgagatc tgacgacacg gccgtgtatt actgtgcgag gcagcagct     360
ggcggatact tccagcactg ggggccaggggc accctggtca ccgtctcctc agctagcacc    420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
gacaaaactc acacatgccc accgtgccca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atga                                           1404
```

<210> SEQ ID NO 37
<211> LENGTH: 467
<212> TYPE: PRT
<213> ORGANISM: Homo sapiens

<400> SEQUENCE: 37

```
Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80
```

```
Gln Lys Leu Gln Gly Arg Val Thr Met Thr Thr Asp Thr Ser Thr Ser
                85                  90                  95
Thr Ala Tyr Met Glu Leu Arg Ser Leu Arg Ser Asp Asp Thr Ala Val
            100                 105                 110
Tyr Tyr Cys Ala Arg Ala Ala Gly Gly Tyr Phe Gln His Trp Gly
        115                 120                 125
Gln Gly Thr Leu Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
210                 215                 220
Lys Pro Ser Asn Thr Lys Val Asp Lys Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
450                 455                 460
Pro Gly Lys
465

<210> SEQ ID NO 38
<211> LENGTH: 31
<212> TYPE: DNA
```

```
<213> ORGANISM: Artificial Sequence
<220> FEATURE:
<223> OTHER INFORMATION: Description of Artificial Sequence: Primer

<400> SEQUENCE: 38
tcttgtccac cttggtgttg ctgggcttgt g                                      31

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 39
ggggccactg tcttctccac ggtgctc                                           27

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 40
ggtgccaggg ggaagaccga tgg                                               23

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 41
cacggctccc gggtagaagt cact                                              24

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 42
gtaaaacgac ggccagtg                                                     18

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 43
caggaaacag ctatgac                                                      17

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 44
agagagagag gtcgacccac catggactgg acctggagca tcctttt                     47
```

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 45
gagagagagg ctagctgagg agacggtgac cagggtg                          37

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 46
agagagagag atctcaccat ggccagcttc cctctcctcc t                     41

<210> SEQ ID NO 47
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 47
agagagagag gaattcctat gaacattctg tagggccac tgtc                   44

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 48
ggtacgtgaa ccgtcagatc gcctgga                                     27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 49
tctatataag cagagctggg tacgtcc                                     27

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 50
tgcacgccgc tggtcagggc gcctgagttc c                                31

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Primer -continued

```
<400> SEQUENCE: 51
tctcataagt gacttctacc cgggagc                                           27

<210> SEQ ID NO 52
<211> LENGTH: 15
<212> TYPE: PRT
<213> ORGANISM: Influenza virus

<400> SEQUENCE: 52

Leu Leu Thr Glu Val Glu Thr Pro Ile Arg Asn Glu Trp Gly Cys
1               5                   10                  15

<210> SEQ ID NO 53
<211> LENGTH: 16
<212> TYPE: PRT
<213> ORGANISM: Influenza virus

<400> SEQUENCE: 53

Ser Leu Leu Thr Glu Val Glu Thr Pro Ile Arg Asn Glu Trp Gly Cys
1               5                   10                  15

<210> SEQ ID NO 54
<211> LENGTH: 6
<212> TYPE: PRT
<213> ORGANISM: Influenza virus

<400> SEQUENCE: 54

Thr Pro Ile Arg Asn Glu
1               5

<210> SEQ ID NO 55
<211> LENGTH: 16
<212> TYPE: PRT
<213> ORGANISM: Influenza virus

<400> SEQUENCE: 55

Leu Leu Thr Glu Val Glu Thr Pro Ile Arg Asn Glu Trp Gly Cys Arg
1               5                   10                  15

<210> SEQ ID NO 56
<211> LENGTH: 15
<212> TYPE: PRT
<213> ORGANISM: Influenza virus

<400> SEQUENCE: 56

Leu Thr Glu Val Glu Thr Pro Ile Arg Asn Glu Trp Gly Cys Arg
1               5                   10                  15

<210> SEQ ID NO 57
<211> LENGTH: 12
<212> TYPE: PRT
<213> ORGANISM: Influenza virus

<400> SEQUENCE: 57

Val Glu Thr Pro Ile Arg Asn Glu Trp Gly Cys Arg
1               5                   10

<210> SEQ ID NO 58
<211> LENGTH: 17
<212> TYPE: PRT
<213> ORGANISM: Influenza virus

<400> SEQUENCE: 58

Glu Thr Pro Ile Arg Asn Glu Trp Gly Cys Arg Cys Asn Asp Ser Ser
1               5                   10                  15
```

Asp

<210> SEQ ID NO 59
<211> LENGTH: 16
<212> TYPE: PRT
<213> ORGANISM: Influenza virus

<400> SEQUENCE: 59

Thr Pro Ile Arg Asn Glu Trp Gly Cys Arg Cys Asn Asp Ser Ser Asp
1               5                   10                  15

<210> SEQ ID NO 60
<211> LENGTH: 15
<212> TYPE: PRT
<213> ORGANISM: Influenza virus

<400> SEQUENCE: 60

Pro Ile Arg Asn Glu Trp Gly Cys Arg Cys Asn Asp Ser Ser Asp
1               5                   10                  15

<210> SEQ ID NO 61
<211> LENGTH: 14
<212> TYPE: PRT
<213> ORGANISM: Influenza virus

<400> SEQUENCE: 61

Ile Arg Asn Glu Trp Gly Cys Arg Cys Asn Asp Ser Ser Asp
1               5                   10

<210> SEQ ID NO 62
<211> LENGTH: 13
<212> TYPE: PRT
<213> ORGANISM: Influenza virus

<400> SEQUENCE: 62

Arg Asn Glu Trp Gly Cys Arg Cys Asn Asp Ser Ser Asp
1               5                   10

<210> SEQ ID NO 63
<211> LENGTH: 12
<212> TYPE: PRT
<213> ORGANISM: Influenza virus

<400> SEQUENCE: 63

Asn Glu Trp Gly Cys Arg Cys Asn Asp Ser Ser Asp
1               5                   10

<210> SEQ ID NO 64
<211> LENGTH: 17
<212> TYPE: PRT
<213> ORGANISM: Influenza virus

<400> SEQUENCE: 64

Ser Leu Leu Thr Glu Val Glu Thr Pro Ile Arg Asn Glu Trp Gly Cys
1               5                   10                  15

Arg

<210> SEQ ID NO 65
<211> LENGTH: 16
<212> TYPE: PRT
<213> ORGANISM: Influenza virus

<400> SEQUENCE: 65

Ser Leu Leu Thr Glu Val Glu Thr Pro Ile Arg Asn Glu Trp Gly Cys

```
<210> SEQ ID NO 66
<211> LENGTH: 15
<212> TYPE: PRT
<213> ORGANISM: Influenza virus

<400> SEQUENCE: 66

Ser Leu Leu Thr Glu Val Glu Thr Pro Ile Arg Asn Glu Trp Gly
1               5                   10                  15

<210> SEQ ID NO 67
<211> LENGTH: 14
<212> TYPE: PRT
<213> ORGANISM: Influenza virus

<400> SEQUENCE: 67

Ser Leu Leu Thr Glu Val Glu Thr Pro Ile Arg Asn Glu Trp
1               5                   10

<210> SEQ ID NO 68
<211> LENGTH: 13
<212> TYPE: PRT
<213> ORGANISM: Influenza virus

<400> SEQUENCE: 68

Ser Leu Leu Thr Glu Val Glu Thr Pro Ile Arg Asn Glu
1               5                   10

<210> SEQ ID NO 69
<211> LENGTH: 12
<212> TYPE: PRT
<213> ORGANISM: Influenza virus

<400> SEQUENCE: 69

Ser Leu Leu Thr Glu Val Glu Thr Pro Ile Arg Asn
1               5                   10

<210> SEQ ID NO 70
<211> LENGTH: 10
<212> TYPE: PRT
<213> ORGANISM: Influenza virus

<400> SEQUENCE: 70

Ser Leu Leu Thr Glu Val Glu Thr Pro Ile
1               5                   10

<210> SEQ ID NO 71
<211> LENGTH: 9
<212> TYPE: PRT
<213> ORGANISM: Influenza virus

<400> SEQUENCE: 71

Ser Leu Leu Thr Glu Val Glu Thr Pro
1               5

<210> SEQ ID NO 72
<211> LENGTH: 8
<212> TYPE: PRT
<213> ORGANISM: Influenza virus

<400> SEQUENCE: 72

Ser Leu Leu Thr Glu Val Glu Thr
1               5
```

```
<210> SEQ ID NO 73
<211> LENGTH: 7
<212> TYPE: PRT
<213> ORGANISM: Influenza virus

<400> SEQUENCE: 73

Ser Leu Leu Thr Glu Val Glu
1               5

<210> SEQ ID NO 74
<211> LENGTH: 15
<212> TYPE: PRT
<213> ORGANISM: Influenza virus

<400> SEQUENCE: 74

Ser Leu Leu Thr Glu Val Glu Thr Pro Ile Arg Asn Glu Trp Gly
1               5                   10                  15

<210> SEQ ID NO 75
<211> LENGTH: 14
<212> TYPE: PRT
<213> ORGANISM: Influenza virus

<400> SEQUENCE: 75

Leu Leu Thr Glu Val Glu Thr Pro Ile Arg Asn Glu Trp Gly
1               5                   10
```

HUMAN MONOCLONAL ANTIBODIES TO INFLUENZA M2 PROTEIN AND METHODS OF MAKING AND USING SAME

RELATED APPLICATIONS

This application is the National Phase of International Application PCT/IB2005/004146 filed Dec. 5, 2005 which designated the U.S. and that International Application was published under PCT Article 21(2) in English.

This application claims the benefit of priority of application Ser. No. 60/633,846, filed Dec. 6, 2004, and application Ser. No. 60/724,198, filed Oct. 6, 2005, which are expressly incorporated herein by reference.

TECHNICAL FIELD

The invention relates to antibodies, more particularly to human, humanized and chimeric antibodies that specifically bind to influenza virus M2 protein. Furthermore, the invention relates to antibodies, more particularly to human, humanized and chimeric antibodies whose minimal binding sequence is LLTEVETPIR (SEQ ID NO: 1).

INTRODUCTION

Influenza types A or B viruses cause epidemics of disease almost every year in all countries and are a leading cause of death in the developed world. In the United States, influenza epidemics can cause illness in about 20% of people and are associated with an average of 20,000 deaths and 114,000 hospitalizations yearly. The present strategy for control of influenza is yearly vaccination with inactivated whole-virus or sub-unit vaccines.

Influenza vaccines have been demonstrated to have a protective effect against influenza infection. However, yearly emerging antigenic variants of influenza viruses necessitate surveillance to contemporary of circulating virus strains. In some cases, difficulty in the prediction of new variant strains has prevented the timely production of the vaccine (Frace et al., Vaccine 17:2237 (1999)). Recently, pandemic avian influenza has become a serious threat due to the emergence of avian influenza viruses such as H5N1 in southern Asia. The currently available vaccines would be ineffective against avian viruses (Lipatov et al., J. Virology 78:8951 (2004); Osterholm et al., N Engl. Med. 352:1839 (2005)). A third problem with the current vaccine is the ineffectiveness in certain populations with compromised immune systems, for instance premature infants, the elderly, AIDS and transplant patients.

Because of unavailability of the vaccine to avian viruses, nations around world are currently trying to stockpile the anti-influenza drug, Tamiflu, a neuraminidase inhibitor, to fight a possible global flu pandemic. The drug is now in short supply. Recently, a drug resistant avian virus was found in a 14-year-girl in Viet Nam. Resistance to Tamiflu has also been found in human influenza as well (Mai Le et al., Nature 437:1108 (2005)). The shed virus can become a problem if it transmitted to other people because Tamiflu is so far the most effective anti-influenza drug. Another concern about Tamiflu is that it is unclear whether it will be effective against severe avian influenza although it can accelerate recovery from mild infection with contemporary influenza strains in adults.

Hemagglutinin (HA) and neuraminidase (NA) are the two major antigens for the stimulation of antibody production. Due to frequent antigenic variation of these two proteins, they do not represent optimal targets for development of therapeutic antibody drugs. A third transmembrane protein of type A influenza virus, matrix protein 2 (M2), is abundantly expressed by virus-infected cells, where it is believed to provide an obligatory transmembrane proton flux for viral replication (Ciampor et al., Virus Research 22:247 (1992); Grambas and Hay, Virology 190:11 (1992); Sugrue et al., EMBO J. 9:3469 (1990)). Unlike HA and NA, M2 is conserved and may represent a target for the development of antibody-based passive immunotherapies for influenza patients (Ito et al., J. Virology 65:5491 (1991); Slepushkin et al., Vaccine 13:1399 (1995); Neirynck et al., Nature Med. 5:1157 (1999)).

SUMMARY

Compositions and methods for prophylaxis and treatment of influenza infection are provided. Compositions include fully human, humanized and chimeric (e.g., human/mouse chimera) monoclonal antibodies that recognize influenza matrix protein 2, M2 protein, from A/PR/8/34, A/HK/1/68 and other strains/isolates and have broad reactivity against differing influenza A strains/isolates and subtypes. Methods include passive immunization with human, humanized and chimeric (e.g., human/mouse chimera) monoclonal antibodies, anti-M2 antibodies, that bind to influenza matrix protein 2, M2 protein, before or after contact with, exposure or infection with influenza.

Human monoclonal anti-M2 antibodies can protect mice from a lethal challenge with influenza A viruses (A/HK/1/68 and A/PR/8/34) when antibody is administered before or after animals were infected with influenza A. Influenza virus replication was dramatically inhibited in vivo. Human anti-M2 antibodies include antibodies having broad antigenic specificity that can bind to a wide variety of M2 sequences. For example, an exemplary antibody binds to most M2 sequence variants including variants from potentially pandemic/epidemic avian influenza isolates. Such human, humanized and chimeric anti-M2 monoclonal antibody that have broad specificity to M2 variant peptides are useful against a variety of influenza trains/isolates and subtypes.

The invention therefore provides human, humanized and chimeric anti-M2 monoclonal antibodies that bind to influenza virus protein M2, compositions including human, humanized and chimeric anti-M2 monoclonal antibodies such as pharmaceutical compositions including human, humanized and chimeric anti-M2 monoclonal antibodies, and kits containing antibody. Human, humanized and chimeric anti-M2 monoclonal antibodies of the invention are useful for treating influenza in a subject having or at risk of having influenza, before infection (prophylaxis) or following infection (therapeutic); influenza detection and diagnostics, including measuring virus titer; purification/isolation including purifying or isolating whole virus or M2 protein; and other assay systems. The invention therefore also provides methods of using the antibodies in therapeutic (e.g., treatment of influenza infection) and non-therapeutic applications such as diagnostics (detecting or measuring amounts of influenza or M2 protein in a sample) and purification (purifying or isolating influenza virus or M2 protein).

In one embodiment, a human antibody that specifically binds to at least a part of the M2 extracellular domain, also referred to and used interchangeably herein as M2 ectodomain (M2e), is provided. In particular aspects, the extracellular/ecto-domain includes or consists of the amino acid sequence SLLTEVETPIRNEWGCRCNDSSD (SEQ ID NO:2), a subsequence thereof or an amino acid variant thereof (e.g., an amino acid substitution, insertion, deletion or addition). In another aspect, the extracellular/ecto-domain is a sequence that includes or consists of an amino acid sequence selected from: SLLTEVETPIRSEWGCRCNDSGD (SEQ ID NO:3), SLLTEVETPIRNEWECRCNGSSD (SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO: 10), SLLTEVETPIRSEWGCRYNDSSD (SEQ ID NO: 11), SLLTEVETPTRNGWECKCSDSSD (SEQ ID NO: 12), SLLTEVETHTRNGWECKCSDSSD (SEQ ID NO:13), SLLTEVKTPTRNGWECKCSDSSD (SEQ ID NO: 14), SLLTEVETLTRNGWGCRCSDSSD (SEQ ID NO: 15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO:18), SLLTEVETLTRNGWECKCSDSSD (SEQ ID NO:19), SLLTEVETPIRNEWGCKCNDSSD (SEQ ID NO:20), SFLTEVETPIRNEWGCRCNGSSD (SEQ ID NO. 21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO:25) and SLLPEVETHTRNGWGCRCSDSSD (SEQ ID NO:26).

In additional aspects, the antibody is produced by a cell line (e.g., hybridoma or a CHO cell line) denoted as no. Z3G1 (ATCC Deposit No. PTA-5967; deposited Mar. 13, 2004, American Type Culture Collection, 10801 University Blvd., Manassas, Va., 20110-2209, USA) and no. Z3G3 (Z3.16.25.1) (ATCC Deposit No. PTA-5968; deposited Mar. 13, 2001, American Type Culture Collection, Manassas, Va., USA).

Antibodies of the invention include polyclonal and monoclonal antibodies and mixtures thereof, which can be any of IgG, IgA, IgM, IgE, IgD, and any isotype thereof, for example, IgG1, IgG2, IgG3 or IgG4. In the case of a monoclonal antibody, an exemplary class of antibody is IgG. Subclasses of IgG include, for example, IgG1, IgG2, IgG3 and IgG4. Antibodies include intact human, humanized and chimeric immunoglobulin molecules with two full-length heavy chains and two full-length light chains (e.g., mature portion of heavy and light chain variable region sequences) as well as subsequences/fragments of heavy or light chain which retain at least a part of a function (M2 binding specificity, M2 binding affinity, or anti-influenza virus activity) of parental intact antibody that specifically binds M2. Subsequences can have the same or substantially the same binding specificity, binding affinity or anti-influenza virus activity as parental intact human, humanized and chimeric antibody.

Exemplary subsequences include Fab, Fab', F(ab')2, Fv, Fd, single-chain Fvs (scFv), disulfide-linked Fvs (sdFv) and VL or VH, or other M2 protein binding fragment of an intact immunoglobulin. Antibodies of the invention therefore include heavy-chain variable region sequence and light-chain variable region sequence of antibody produced by the hybridoma or a CHO cell line denoted as no. Z3G1 (ATCC Deposit No. PTA-5967; deposited Mar. 13, 2004, American Type Culture Collection, Manassas, Va., USA) and no. Z3G3 (Z3.16.25.1)(ATCC Deposit No. PTA-5968; deposited Mar. 13, 2004, American Type Culture Collection, Manassas, Va., USA).

Antibodies further include human, humanized and chimeric antibodies having the same or substantially the same binding specificity, affinity, or anti-influenza virus activity, of an antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA). In a particular embodiment, an antibody having the same binding specificity as antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds to at least one of the M2 variant sequences to which antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds. In an additional particular embodiment, an antibody having substantially the same binding specificity as antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds to or weakly binds to at least 5 to 10, 10 to 15, 15 to 20, 20 to 25 or more of the M2 variant sequences to which antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds. In a further particular embodiment, an antibody having substantially the same binding specificity as antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds to or weakly binds to at least 10 to 15, 15 to 20, 20 to 25 or more of the M2 variant sequences to which antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds, but does not bind to, or only weakly binds to, an M2 sequence to which anti-M2 antibody L66, N547, C40G1 or 14C2 antibody binds.

In additional embodiments, the affinity, or anti-influenza virus activity, is within about 5 to 1000 fold greater or less than a reference antibody. Thus, where the reference antibody has a Kd of $10^{-9}$ M, for example, antibodies of the invention include antibodies having a Kd within 5 to 1000 fold greater or less than $10^{-9}$ M. Thus, in one aspect, an antibody has a binding affinity within about 5 to 1000 fold greater or less than an antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA).

In further embodiments, an antibody binds to the same epitope as a reference antibody. Thus, in one aspect, an antibody binds to the same epitope as an antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA). In another aspect, an antibody binds to an epitope to which the antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds. In still another aspect, an antibody binds to an epitope within any M2 amino acid sequence, for example, SLLTEVETPIRNEWGCRCNDSSD (SEQ ID NO:2), SLLTEVETPIRSEWGCRCNDSGD (SEQ ID NO:3), SLLTEVETPIRNEWECRCNGSSD (SEQ ID NO:4), SLPTEVETPIRNEWGCRCNDSSD (SEQ ID NO. 5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO: 11), SLLTEVETPTRNGWECKCSDSSD (SEQ ID NO: 12), SLLTEVETHTRNGWECKCSDSSD (SEQ ID NO: 13), SLLTEVKTPTRNGWECKCSDSSD (SEQ ID NO:14), SLLTEVETLTRNGWGCRCSDSSD (SEQ ID NO: 15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO: 18), SLLTEVETLTRNGWECKCSDSSD (SEQ ID NO: 19), SLLTEVETPIRNEWGCKCNDSSD (SEQ ID NO. 20), SFLTEVETPIRNEWGCRCNGSSD (SEQ ID NO. 21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO: 25), SLLPEVETHTRNGWGCRCSDSSD (SEQ ID NO:26) and LLTEVETPIR (SEQ ID NO: 1).

Antibodies of the invention further include human, humanized and chimeric antibodies that bind to a minimal binding sequence of M2 protein. In various aspects, an antibody binds to a minimal binding sequence within LLTEVETPIR (SEQ ID NO: 1). In particular aspects, a minimal binding sequence for antibody binding is LLTEVETPIR (SEQ ID NO:1). In further aspects, a minimal binding sequence for human M2 antibody is the same or substantially the same as LLTEVET-PIR (SEQ ID NO:1). In additional aspects, human M2 antibody binds to a minimal binding sequence that is LLTEVET-PIR (SEQ ID NO:1). Still additional aspects include M2 antibodies that bind to a minimal binding sequence within any of SLLTEVETPIRNEWGCRCNDSSD (SEQ ID NO:2), SLLTEVETPIRSEWGCRCNDSGD (SEQ ID NO:3), SLLTEVETPIRNEWECRCNGSSD (SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO:11), SLLTEVETPTRNGWECKCSDSSD (SEQ ID NO:12), SLLTEVETHTRNGWECKCSDSSD (SEQ ID NO:13), SLLTEVKTPTRNGWECKCSDSSD (SEQ ID NO:14), SLLTEVETLTRNGWGCRCSDSSD (SEQ ID NO:15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO:18), SLLTEVETLTRNGWECKCSDSSD (SEQ ID NO:19), SLLTEVETPIRNEWGCKCNDSSD (SEQ ID NO:20), SFLTEVETPIRNEWGCRCNGSSD (SEQ ID NO:21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO:25) and SLLPEVETHTRNGWGCRCSDSSD (SEQ ID NO:26). Antibodies of the invention additionally include human, humanized and chimeric antibodies having a function or activity as the exemplified antibodies produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA), for example, ability to inhibit virus infection in vitro or in vivo or inhibit M2 binding of a cell in vitro or in vivo (e.g., MDCK cell). In various aspects, an antibody has an EC50 less than 2.0 to 3.0, 1.0 to 2.0, 0.5 to 1.0, 0.1 to 0.5 or less than 0.1 µg/ml (e.g., 0.05 to 0.1 µg/ml) for inhibiting influenza virus infection of MDCK cells, as determined by a cell based-ELISA assay. In additional aspects, an antibody has an EC50 less than 2.0 to 3.0, 1.0 to 2.0, 0.5 to 1.0, 0.1 to 0.5 or less than 0.1 µg/ml (e.g., 0.05 to 0.1 µg/ml) for inhibiting M2 binding to MDCK cells, as determined by a cell based-ELISA assay. In further aspects, the influenza virus is influenza A virus, such as A/PR/8/34 (H1N1) or A/1K/T/68 (H3N2) strain/isolate, or other subtype, such as H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 or H5N3.

Antibodies of the invention further include human, humanized and chimeric antibodies that bind to two or more M2 proteins having different amino acid sequences (e.g., having different extracellular/ecto-domain sequences of M2, i.e., M2e), which may optionally be present on different influenza viruses (e.g., strains/isolates or subtypes). In one embodiment, the antibody binds to at least a part of an M2 extracellular/ecto-domain sequence, M2e. In particular aspects, an M2e sequence includes or consists of the amino acid sequence SLLTEVETPIRNEWGCRCNDSSD (SEQ ID NO:2), a subsequence thereof or an amino acid variant thereof (e.g., an amino acid substitution, insertion, deletion or addition), such as SLLTEVETPIRSEWGCRCNDSGD (SEQ ID NO:3). In other particular aspects, an M2e sequence includes or consists of an amino acid sequence selected from: SLLTEVETPIRSEWGCRCNDSGD (SEQ ID NO:3), SLLTEVETPIRNEWECRCNGSSD (SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO:11), SLLTEVETPTRNGWECKCSDSSD (SEQ ID NO:12), SLLTEVETHTRNGWECKCSDSSD (SEQ ID NO:13), SLLTEVKTPTRNGWECKCSDSSD (SEQ ID NO:14), SLLTEVETLTRNGWGCRCSDSSD (SEQ ID NO:15), SLLTEVETPTRDGWECKCSDSSD (SEQ ID NO:16), SLLTEVETPTRNGWGCRCSDSSD (SEQ ID NO:17),
SLLTEVETPTRNGWECKCNDSSD (SEQ ID NO:18),
SLLTEVETLTRNGWECKCSDSSD (SEQ ID NO:19),
SLLTEVETPIRNEWGCKCNDSSD (SEQ ID NO:20),
SFLTEVETPIRNEWGCRCNGSSD (SEQ ID NO:21),
SLLTEVETPTRNGWECRCNDSSD (SEQ ID NO:22),
SLLTEVETPIRKGWECNCSDSSD (SEQ ID NO:23),
SLLTEVETPTRNEWECRCSDSSD (SEQ ID NO:24),
SLLTGVETHTRNGWGCKCSDSSD (SEQ ID NO:25) and
SLLPEVETHTRNGWGCRCSDSSD (SEQ ID NO:26) Antibodies of the invention include those that have been modified to form oligomers, e.g., through the covalent attachment of an oligomerization domain (e.g., leucine zipper motif) or via a cross-linking agent (e.g., chemical cross linker). Thus, antibodies of the invention include multimeric forms, for example, dimers, trimers, tetramers or higher order human, humanized and chimeric antibody oligomers. Such antibody multimers typically exhibit increased avidity for M2 in comparison to monomeric antibody.

Antibodies of the invention further include one or more heterologous domains that impart a distinct function or activity on an antibody that binds M2. Antibodies include an amino acid heterologous domain when one or more amino acids are distinct from the antibody (i.e., they are not a part of the native antibody). In one embodiment, a heterologous domain comprises a binding protein (e.g., receptor or ligand binding), an enzyme activity, a drug, an antiviral, a toxin, an immune-modulator, a detectable moiety or a tag. In one aspect, the binding protein comprises an antibody having a different binding specificity or affinity than a human, humanized or chimeric antibody that specifically binds to influenza protein M2. Thus, the invention further provides multi-specific and multi-functional antibodies (e.g., bispecific and bifunctional antibodies, such as antibodies that bind to two or more antigens or that have two or more functions or activities, respectively).

Antibodies of the invention can bind to influenza protein M2, optionally present on one or more influenza strains/isolates or subtypes. Thus, the antibodies have one or more effects on M2 or influenza virus infectivity, replication, proliferation, titer, progression, severity, frequency, duration or probability of one or more symptoms or complications associated with influenza, or susceptibility of influenza virus infection, i.e., anti-influenza virus activity.

In one embodiment, a human, humanized or chimeric antibody inhibits infection of a cell in vitro or in vivo, or inhibits influenza binding of a cell in vitro or in vivo, by one or more influenza strains/isolates or subtypes. In another embodiment, a human, humanized or chimeric antibody reduces influenza virus titer or an amount of an influenza viral protein of one or more influenza strains/isolates or subtypes. In yet another embodiment, a human, humanized or chimeric antibody inhibits or prevents increases in influenza virus titer or an amount of an influenza viral protein of one or more influenza strains/isolates or subtypes. In still another embodiment, a human, humanized or chimeric antibody protects a subject from infection or decreases susceptibility of the subject to infection by one or more influenza strains/isolates or subtypes. In a further embodiment, a human, humanized or chimeric antibody decreases progression, severity, frequency, duration or probability of one or more symptoms or complications associated with infection by one or more influenza strains/isolates or subtypes (e.g., chills, fever, cough, sore throat, nasal congestion, sinus congestion, nasal infection, sinus infection, body ache, head ache, fatigue, pneumonia, bronchitis, ear infection, ear ache or death). In various aspects, human, humanized or chimeric antibody is administered systemically (e.g., intravenous injection, subcutaneous injection, intravenous infusion, intramuscular injection), or locally to mucosal tissue (e.g., nasal passages, sinuses, throat, larynx, esophagus, ear or ear canal) or lung of a subject. In various aspects, the influenza is influenza A, and an influenza A strain is selected from A/PR/8/34 (H1N1) or A/HK/1/68 (H3N2) strain/isolate, or subtype, such as H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 or H5N3.

Host cells that express invention human, humanized and chimeric antibodies are also provided. Cells include but are not limited to bacteria, yeast, plant, animal (e.g., mammalian cells such as hybridoma cell lines and CHO cell lines) as well as whole organisms such as non-human animals and plants that express invention human, humanized or chimeric antibodies. Host cells can be used to produce antibodies, which optionally can be subsequently isolated or purified.

Nucleic acids encoding antibodies of the invention, including subsequences/fragments and variants thereof, are further provided. In particular embodiments, a nucleic acid encodes a heavy-chain sequence or a light-chain sequence as set forth in Example 1 (e.g., SEQ ID NOs:34, 35 and 37), and subsequences thereof (e.g., variable heavy-chain or light-chain sequence). Nucleic acids include vectors for cloning or other genetic manipulation of the nucleic acid or for expression in solution, in a cell, or in any organism. Nucleic acids can therefore be used to produce antibodies in solution (e.g., in vitro translation), in a cell in vitro or in vivo, which optionally can be subsequently isolated or purified.

Combination compositions including antibodies of the invention are also provided. In one embodiment, a composition includes human, humanized or chimeric antibody that binds influenza M2 protein and an antiviral agent. In another embodiment, a composition includes a human, humanized or chimeric antibody that binds influenza M2 protein and an agent that inhibits one or more symptoms or complications associated with influenza infection (e.g., chills, fever, cough, sore throat, nasal congestion, sinus congestion, nasal infection, sinus infection, body ache, head ache, fatigue, pneumonia, bronchitis, ear infection, ear ache or death).

Pharmaceutical compositions including antibodies of the invention and a pharmaceutically acceptable carrier or excipient are provided. In one embodiment, a carrier is suitable for administration systemically, regionally, or locally, to mucosal tissue (e.g., nasal passages, sinuses, throat, larynx, esophagus) or lung of a subject.

Kits that include one or more antibodies of the invention are also provided. In one embodiment, a kit includes instructions for treating (prophylaxis or therapeutic), inhibiting, preventing, decreasing susceptibility to, or reducing progression, severity, frequency, duration or probability of one or more symptoms or complications associated with influenza virus infection of a subject by one or more influenza strains/isolates or subtypes. In another embodiment, a kit includes an article of manufacture, such as an aerosol, spray or squeeze bottle or other delivery means suitable for inhalation or nasal administration to a subject. In yet another embodiment, the kit or article of manufacture includes an antiviral agent (e.g., an antibody or a drug) or an agent that inhibits one or more symptoms or complications associated with influenza infection.

Methods for treating influenza infection of a subject are provided. In one embodiment, a method includes administering to the subject an amount of a human, humanized or chimeric antibody that specifically binds influenza M2 effective to treat influenza infection of the subject. In various aspects, the antibody is administered substantially contemporaneously with or following infection of the subject, i.e., therapeutic treatment. In another aspect, the antibody provides a therapeutic benefit. In various aspects, a therapeutic benefit includes reducing or decreasing progression, severity, frequency, duration or probability of one or more symptoms or complications of influenza infection, virus titer, virus replication or an amount of a viral protein of one or more influenza strains. Symptoms or complications of influenza infection that can be reduced or decreased include, for example, chills, fever, cough, sore throat, nasal congestion, sinus congestion, nasal infection, sinus infection, body ache, head ache, fatigue, pneumonia, bronchitis, ear infection, ear ache or death. In still another aspect, a therapeutic benefit includes hastening or accelerating a subject's recovery from influenza infection.

Methods for inhibiting infection of a subject by one or more influenza strains or isolates are also provided. In one embodiment, a method includes administering to the subject an amount of a human, humanized or chimeric antibody that specifically binds influenza M2 effective to inhibit infection of the subject or reduce susceptibility of the subject to influenza infection by one or more influenza strains or isolates. In various aspects, the antibody is administered prior to (prophylaxis), substantially contemporaneously with or following infection of the subject. In another aspect, the antibody provides a therapeutic benefit. In various aspects, a therapeutic benefit includes reducing or decreasing onset or progression, severity, frequency, duration or probability of one or more symptoms or complications of influenza infection (e.g., chills, fever, cough, sore throat, nasal congestion, sinus congestion, nasal infection, sinus infection, body ache, head ache, fatigue, pneumonia, bronchitis, ear infection, ear ache or death), virus titer or an amount of a viral protein of one or more influenza strains or isolates, or susceptibility of a subject to infection by one or more influenza strains or isolates.

Methods for preventing an increase in influenza virus titer, virus replication, virus proliferation or an amount of an influenza viral protein in a subject are further provided. In one embodiment, a method includes administering to the subject an amount of a human, humanized or chimeric antibody that specifically binds influenza M2 effective to prevent an increase in influenza virus titer, virus replication or an amount of an influenza viral protein of one or more influenza strains or isolates in the subject.

Methods for protecting a subject from infection or decreasing susceptibility of a subject to infection by one or more influenza strains/isolates or subtypes, i.e., prophylactic methods, are additionally provided. In one embodiment, a method includes administering to the subject an amount of a human, humanized or chimeric antibody that specifically binds influenza M2 effective to protect the subject from infection, or effective to decrease susceptibility of the subject to infection, by one or more influenza strains/isolates or subtypes. In one aspect, the protection includes reducing or decreasing influenza infection or one or more symptoms or complications associated with influenza infection (e.g., chills, fever, cough, sore throat, nasal congestion, sinus congestion, nasal infection, sinus infection, body ache, head ache, fatigue, pneumonia, bronchitis, ear infection, ear ache or death).

Methods of the invention can be practiced with antibody having the binding specificity or binding affinity of an antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA. Antibodies can be included in a pharmaceutically acceptable carrier or excipient prior to administration to a subject. Methods that include administration to a subject include systemic, regional or local delivery.

Methods of the invention, including therapeutic/prophylactic, diagnostic/detection and purification/isolation are applicable to any influenza strains/isolate or subtype, or combination of strains/isolates or subtypes. In various embodiments, the influenza is influenza A, and an influenza A is selected from as A/PR/8/34 (H1N1) or A/HK/1/68 (H3N2) strain/isolate, or other subtype, such as H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N3.

Methods for producing human M2 antibodies are provided. In one embodiment, a method includes, administering M2 or an immunogenic subsequence/fragment thereof to an animal (e.g., a non-human animal) capable of expressing human immunoglobulin; screening the animal for expression of human M2 antibody; selecting an animal that produces a human M2 antibody; isolating an antibody from the animal producing human M2 antibody; and determining whether the human M2 antibody binds to M2. In another embodiment, a method includes, administering M2 or an immunogenic subsequence/fragment thereof to an animal (e.g., a non-human animal) capable of expressing human immunoglobulin; screening the animal for expression of human M2 antibody; selecting an animal producing an human M2 antibody; isolating spleen cells from the animal that produces human M2 antibody; fusing the spleen cells with a myeloma cell to produce a hybridoma; and screening the hybridoma for expression of a human M2 antibody. In various aspects, the M2 or immunogenic subsequence/fragment thereof includes or consists of an M2 extracellular/ecto-domain, M2e. In additional aspects, M2e includes a minimal binding sequence for human M2 antibody that is the same or substantially the same as LLTEVETPIR (SEQ ID NO: 1). In further aspects, an M2e includes a minimal binding sequence that is LLTEVETPIR (SEQ ID NO: 1).

In yet another embodiment, a method includes, providing an animal (e.g., non-human animal) or cell that produces a human M2 antibody; and isolating an antibody from the animal or cell. In still another embodiment, a method includes, providing an animal (e.g., non-human animal) that produces a human M2 antibody; isolating spleen cells from the animal that produces human M2 antibody; fusing the spleen cells with a myeloma cell to produce a hybridoma; and screening the hybridoma for expression of a human M2 antibody. In various aspects, the animal or cell expresses an antibody having the binding specificity or the same or substantially the same binding affinity or anti-influenza virus activity as antibody produced by a hybridoma or a CHO cell line denoted as no. Z3G1 (ATCC Deposit No. PTA-5967; deposited Mar. 13, 2004, American Type Culture Collection, Manassas, Va., USA, and no. Z3G3 (Z3.16.25.1) (ATCC Deposit No. PTA-5968; deposited Mar. 13, 2004, American Type Culture Collection, Manassas, Va., USA). In additional aspects, the animal or cell expresses an antibody having binding specificity for an M2 extracellular domain that includes a minimal binding sequence that is the same or substantially the same as LLTEVETPIR (SEQ ID NO: 1). In further aspects, the animal or cell expresses an antibody having binding specificity for an M2 extracellular domain that includes a minimal binding sequence that is LLTEVETPIR (SEQ ID NO:1). In still additional aspects, the animal or cells expresses an antibody that binds to a minimal binding sequence within any of SLLTEVETPIRNEWGCRCNDSSD (SEQ ID NO:2), SLLTEVETPIRSEWGCRCNDSGD (SEQ ID NO:3), SLLTEVETPIRNEWECRCNGSSD(SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO:11), SLLTEVETPTRNGWECKCSDSSD (SEQ ID NO:12), SLLTEVETHTRNGWECKCSDSSD (SEQ ID NO:13), SLLTEVKTPTRNGWECKCSDSSD (SEQ ID NO:14), SLLTEVETLTRNGWGCRCSDSSD (SEQ ID NO:15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO:18), SLLTEVETLTRNGWECKCSDSSD (SEQ ID NO:19), SLLTEVETPIRNEWGCKCNDSSD (SEQ ID NO:20), SFLTEVETPIRNEWGCRCNGSSD (SEQ ID NO:21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO:25) and SLLPEVETHTRNGWGCRCSDSSD (SEQ ID NO:26).

DESCRIPTION OF DRAWINGS

FIG. 6 shows that M2 antibody Z3G1 protects NK depleted mice from a lethal dose of A/HK/1/68 challenge. NK cell depleted (NK) or non depleted (NK+) mice were administered anti M2 antibody Z3G1 or an isotype control antibody (HSA) at a dose of 100 μg/mouse one day before infection with a lethal dose of A/LK/1/68. Survival rate was observed from day 1 to day 23 post infection.

FIG. 7 shows that M2 antibody Z3G1 protects mice from a lethal dose of A/HK/1/68 challenge at a therapeutic regimen. Mice were administered anti M2 antibody Z3G1 at doses of 200 μg, 100 μg or 30 μg per mouse or an isotype control antibody (HSA) at 200 μg per mouse one day after infection with a lethal dose of A/HK/1/68. Survival rate was observed from day 1 to day 23 post infection.

DETAILED DESCRIPTION

Figure 1:
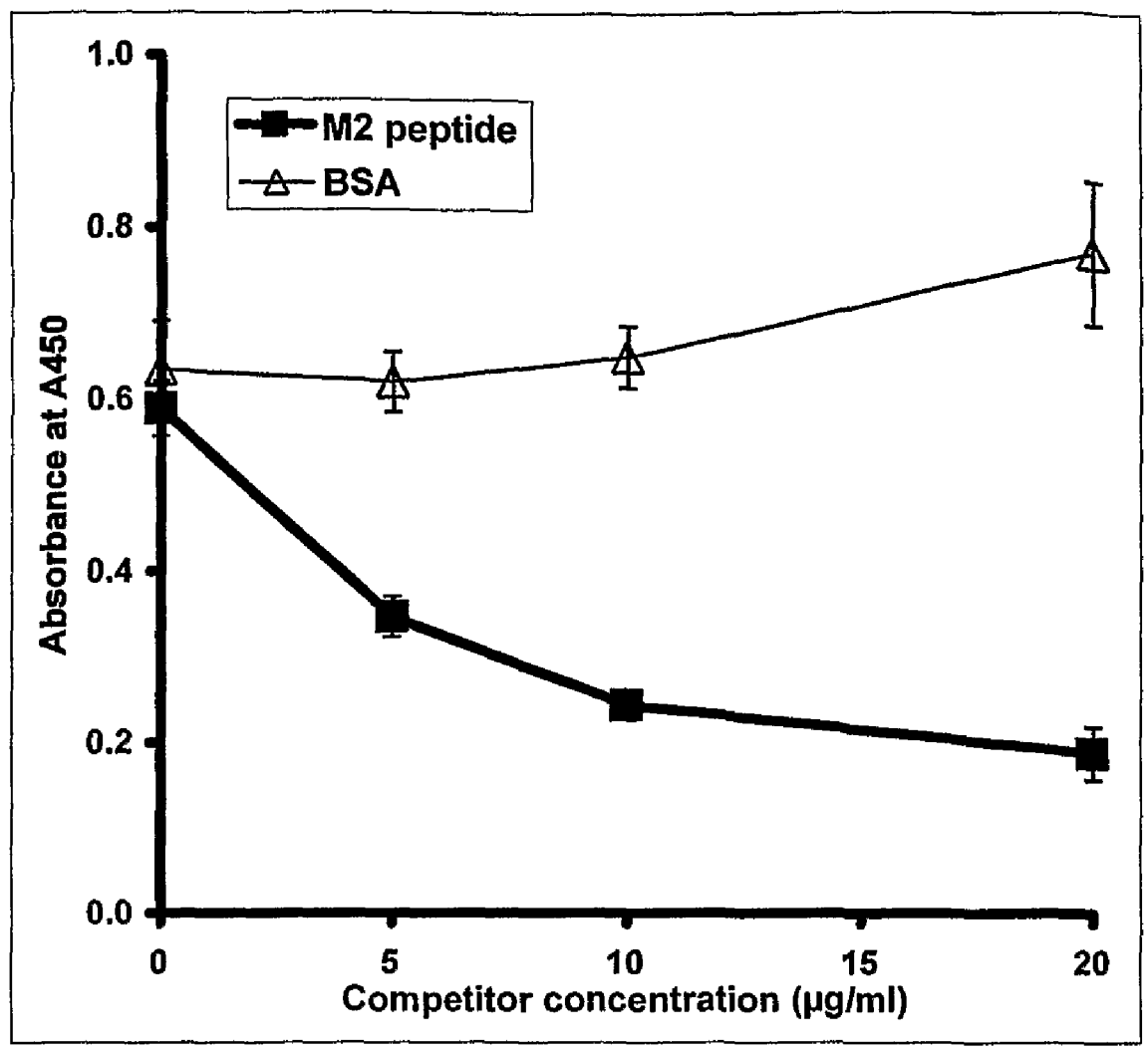
FIG. 1 shows that antibody no. Z3G1 binding to M2 on surface of A/PR/8/34 infected cells is specifically inhibited by soluble M2 peptide, but not irrelevant protein, BSA. Antibody binding to A/PR/8/34 infected MDCK cells was measured by ELISA.

The invention is based at least in part on human, humanized and chimeric anti-M2 monoclonal antibodies. Several of the invention antibodies have broad reactivity against various M2 extracellular domain sequences based upon divergent influenza A virus strains. Passive transfer of an invention human anti-M2 monoclonal antibody protected animals from a lethal dose challenge of influenza A/HK/1/68, in both prophylactic (prior to virus infection) and therapeutic (following virus infection) mouse influenza models. Antibodies of the invention are therefore useful for treating a broad array of influenza strains or isolates. In addition, invention human antibodies are less likely to induce hypersensitivity from repeated administration and are more likely to remain in a subject's (e.g., a human) body for a longer period of time.

Thus, in accordance with the invention, there are provided human, humanized and chimeric antibodies that specifically bind to influenza M2 protein. In one embodiment, a human, humanized or chimeric antibody that specifically binds to influenza protein M2 extracellular/ecto-domain, M2e, is provided. In a particular aspect, M2e comprises the amino acid sequence SLLTEVETPIRNEWGCRCNDSSD (SEQ ID NO:2), a portion thereof or an amino acid variant thereof (e.g., an amino acid substitution, insertion, deletion or addition), such as, for example, SLLTEVETPIRSEWGCRCNDSGD (SEQ ID NO:3). In particular aspects, an M2e has an amino acid substitution selected from: SLLTEVETPIRSEWGCRCNDSGD (SEQ ID NO:3), SLLTEVETPIRNEWECRCNGSSD (SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO:11), SLLTEVETPTRNGWECKCSDSSD (SEQ ID NO:12), SLLTEVETHTRNGWECKCSDSSD (SEQ ID NO:13), SLLTEVKTPTRNGWECKCSDSSD (SEQ ID NO:14), SLLTEVETLTRNGWGCRCSDSSD (SEQ ID NO:15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO:18), SLLTEVETLTRNGWECKCSDSSD (SEQ ID NO:19), SLLTEVETPIRNEWGCKCNDSSD (SEQ ID NO:20), SFLTEVETPIRNEWGCRCNGSSD (SEQ ID NO:21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO:25) and SLLPEVETHTRNGWGCRCSDSSD (SEQ ID NO:26).

The term "antibody" refers to a protein that binds to other molecules (antigens) via heavy and light chain variable domains, $V_H$ and $V_L$, respectively. "Antibody" refers to any polyclonal or monoclonal immunoglobulin molecule, such as IgM, IgG, IgA, IgE, IgD, and any subclass thereof, such as $IgG_1$, $IgG_2$, $IgG_3$, $IgG_4$, etc. The term "antibody" also means a functional fragment or subsequence of immunoglobulin molecules, such as, for example, Fab, Fab', F(ab')$_2$, Fv, Fd, scFv and sdFv, unless otherwise expressly stated.

The terms "M2 antibody" or "anti-M2 antibody" means a polyclonal or monoclonal antibody that specifically binds to influenza M2 protein, such as M2 extracellular/ecto-domain, M2e. Specific binding is that which is selective for an epitope present in M2 protein. That is, binding to proteins other than M2 is such that the binding does not significantly interfere with detection of M2, unless such other proteins have a similar or the same epitope or minimal binding sequence as in M2 protein so as to be recognized by an M2 antibody. Selective binding can be distinguished from non-selective binding using assays known in the art.

The term "isolated," when used as a modifier of an invention composition (e.g., antibodies, modified forms, subsequences, nucleic acids encoding same, etc.), means that the compositions are made by the hand of man or are separated, at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms, such as polypeptide multimers, post-translational modifications (e.g., phosphorylation, glycosylation) or derivatized forms.

An "isolated" composition such as an antibody can also be "substantially pure" when free of most or all of the materials with which it typically associates with in nature. Thus, an isolated antibody that also is substantially pure does not include polypeptides or polynucleotides present among millions of other sequences, such as antibodies of an antibody library or nucleic acids in a genomic or cDNA library, for example. A "substantially pure" molecule can be combined with one or more other molecules. Thus, "substantially pure" does not exclude combinations of compositions.

Exemplary M2 antibodies of the invention are denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA 5968; deposited Mar. 13, 2004, American Type Culture Collection, Manassas, Va., USA). Exemplary heavy-chain sequence and light-chain sequence is an amino acid sequence set forth in Example 1 (e.g., SEQ ID NOs:34, 35 and 37).

As used herein, the term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced. As used herein, a specific name, numeral or other designation given to a hybridoma or other cell line (e.g., CHO) that produces an antibody, such as no. Z3G1, N547, L66 and C40G1, can also be used to refer to the antibody.

The term "human" when used in reference to an antibody, means that the amino acid sequence of the antibody is fully human. A "human M2 antibody" or "human anti-M2 antibody" therefore refers to an antibody having human immunoglobulin amino acid sequences, i.e., human heavy and light chain variable and constant regions that specifically bind to M2. That is, all of the antibody amino acids are human or exist in a human antibody. Thus, for example, an antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4th Ed., U.S. Department of Health and Human Services. Public Health Service (1987); and Chothia and Lesk, *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I based on a survey of 30 known human kappa I sequences is described in Padlan *Mol. Immunol.* 31:169 (1994); and Padlan *Mol, Immunol.* 28:489 (1991)). Human antibodies therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, etc.) of one or more determining regions (CDRs) that specifically bind to the desired antigen (e.g., M2) in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human framework regions can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or framework sequences. For example, a framework substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)). Antibodies referred to as "primatized" in the art are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

As used herein, the term "chimeric" and grammatical variations thereof, when used in reference to an antibody, means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine heavy or light chain variable region). Thus, a chimeric antibody is a molecule in which different portions of the antibody are of different species origins. Unlike a humanized antibody, a chimeric antibody can have the different species sequences in any region of the antibody.

As used herein, the terms "M2," "M2 protein," "M2 sequence" and "M2 domain" refer to all or a portion of an M2 protein sequence (e.g., a subsequence such as the extracellular domain) isolated from, based upon or present in any naturally occurring or artificially produced influenza virus strain or isolate. Thus, the term M2 and the like include naturally occurring M2 sequence variants produced by mutation during the virus life-cycle or produced in response to a selective pressure (e.g., drug therapy, expansion of host cell tropism or infectivity, etc.), as well as recombinantly or synthetically produced M2 sequences. M2e is used to refer to the extracellular portion or "ectodomain" of the M2 sequence.

The term "M2 peptide" refers to the extracellular amino acid sequence or ectodomain, M2e, of full length M2 protein. An exemplary M2e consists of the sequence SLLTEVET- PIRNEWGCRCNDSSD (SEQ ID NO:2). Additional exemplary M2e sequences consist of: SLLTEVETPIRNEWECRCNGSSD (SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO:11), SLLTEVETPTRNGWECKCSDSSD (SEQ ID NO:12), SLLTEVETHTRNGWECKCSDSSD (SEQ ID NO:13), SLLTEVKTPTRNGWECKCSDSSD (SEQ ID NO:14), SLLTEVETLTRNGWGCRCSDSSD (SEQ ID NO: 15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO:18), SLLTEVETLTRNGWECKCSDSSD (SEQ ID NO:19), SLLTEVETPIRNEWGCKCNDSSD (SEQ ID NO:20), SFLTEVETPIRNEWGCRCNGSSD (SEQ ID NO:21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO:25) and SLLPEVETHTRNGWGCRCSDSSD (SEQ ID NO:26).

M2 antibodies of the invention include antibodies having kappa or lambda light chain sequences, either full length as in naturally occurring antibodies, mixtures thereof (i.e., fusions of kappa and lambda chain sequences), and subsequences/fragments thereof, as described herein. Naturally occurring antibody molecules contain two kappa and two lambda light chains. The primary difference between kappa and lambda light chains is in the sequences of the constant region.

M2 antibodies of the invention can belong to any antibody class or subclass. Exemplary subclasses for IgG are $IgG_1$, $IgG_2$, $IgG_3$ and $IgG_4$. Invention antibodies include antibodies having either or both of antibody-dependent cell-mediated cytotoxicity (ADCC) and complement-mediated cytotoxicity (CDC) activities, which are expected for effective therapeutic or prophylactic treatment of influenza A (i.e., killing influenza A infected cells or influenza A virus). An exemplary M2 antibody of IgG subclass $IgG_1$ (Z3G1, ATCC Deposit No. PTA-5967; deposited Mar. 13, 2004, American Type Culture Collection, Manassas, Va., USA) exhibits both ADCC and CDC activities (see, for example, Example 5).

Invention M2 antibodies include antibodies having the binding specificity of the M2 antibodies exemplified herein, e.g., having the binding specificity of an antibody denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA 5968; deposited Mar. 13, 2004, American Type Culture Collection, Manassas, Va., USA). In one aspect, an M2 antibody has a heavy (H) or light (L) chain sequence, or a subsequence thereof, as set forth in any of nos. Z3G1 (ATCC Deposit No. PTA-5967; deposited Mar. 13, 2004, American Type Culture Collection, Manassas, Va., USA) or Z3G3 (Z3.16.25.1) (ATCC Deposit No. PTA-5968; deposited Mar. 13, 2004, American Type Culture Collection, Manassas, Va., USA), provided that the heavy or light chain sequence, or subsequence of the antibody has the binding specificity of no. Z3G1 (ATCC Deposit No. PTA-5967; deposited Mar. 13, 2004, American Type Culture Collection, Manassas, Va., USA) or no. Z3G3 (Z3.16.25.1) (ATCC Deposit No. PTA-5968; deposited Mar. 13, 2004, American Type Culture Collection, Manassas, Va., USA).

The term "binding specificity," when used in reference to an antibody, means that the antibody specifically binds to all or a part of the same antigenic epitope as the reference antibody. Thus, an M2 antibody having the binding specificity of the antibody denoted as Z3G1 specifically binds to all or a part of the same epitope as the M2 antibody denoted as Z3G1. Accordingly, antibodies that bind to the same epitope or a part of the same epitope as an antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) are provided.

A part of an antigenic epitope means a subsequence or a portion of the epitope. For example, if an epitope includes 8 contiguous amino acids, a subsequence and, therefore, a part of an epitope may be 7 or fewer amino acids within this 8 amino acid sequence epitope. In addition, if an epitope includes non-contiguous amino acid sequences, such as a 5 amino acid sequence and an 8 amino acid sequence which are not contiguous with each other, but form an epitope due to protein folding, a subsequence and, therefore, a part of an epitope may be either the 5 amino acid sequence or the 8 amino acid sequence alone.

Antibodies having the same or substantially the same binding specificity of the M2 antibodies exemplified herein compete with the binding of no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA). An antibody of the invention having binding specificity of the M2 antibodies exemplified herein may be characterized by any method known in the art for determining competitive binding, for example, the immunoassays disclosed herein. Because the binding affinity of such antibodies may differ from the exemplified antibodies (i.e., have greater or less affinity), the antibodies will vary in their ability to compete for binding to M2. Such antibodies with greater or less affinity may have the same or substantially the same binding specificity as the exemplified antibodies. In particular embodiments, the antibody competitively inhibits binding by at least 95%, at least 90%, at least 85%, at least 80%, at least 75%, at least 70%, at least 65%, at least 60%, at least 55%, at least 50%, at least 45%, at least 40%, at least 35%, or at least 30%, or less.

In particular embodiments, an antibody having the same binding specificity as antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds to at least one of the M2 variant sequences to which antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds. In additional particular embodiments, an antibody having substantially the same binding specificity as antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds to or weakly binds to at least 5 to 10, 10 to 15, 15 to 20, 20 to 25 or more of the M2 variant sequences to which antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds. In further particular embodiments, an antibody having substantially the same binding specificity as antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds to or weakly binds to at least 10 to 15, 15 to 20, 20 to 25 or more of the M2 variant sequences to which antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA) binds, but does not bind to, or only weakly binds to, an M2 sequence to which anti-M2 antibody L66, N547, C40G1 or 14C2 antibody binds.

Epitopes typically are short amino acid sequences, e.g. about five to 15 amino acids in length. Epitopes may be identified, as set forth in Example 3. Systematic techniques for identifying epitopes are also known in the art and are described, for example, in U.S. Pat. No. 4,708,871. Briefly, a set of overlapping oligopeptides derived from an M2 antigen (e.g., M2e) may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-M2 monoclonal antibody. Alternatively, phage display peptide library kits (New England BioLabs) are commercially available for epitope mapping. Using these methods, binding affinity for every possible subset of consecutive amino acids may be determined in order to identify the epitope that a particular antibody binds. Epitopes may also be identified by inference when epitope length peptide sequences are used to immunize animals from which antibodies that bind to the peptide sequence are obtained. Continuous epitopes can also be predicted using computer programs, such as BEPITOPE, known in the art (Odorico et al., *J. Mol. Recognit.* 16:20 (2003))

An exemplary epitope of M2e for Z3G1, is within an amino acid sequence, LLTEVETPIR (SEQ ID NO:1). Exemplary epitope for Z3G1 is also within an amino acid sequence, SLLTEVETPIRSEWGCRCNDSGD (SEQ ID NO:3), SLLTEVETPIRNEWECRCNGSSD (SEQ ID NO:4), SLPTEVETPIRNEWGCRCNDSSD (SEQ ID NO:5), SLLTEVETPIRNEWGCRCNGSSD (SEQ ID NO:6), SLLTEVDTLTRNGWGCRCSDSSD (SEQ ID NO:7), SLLTEVETPIRKEWGCNCSDSSD (SEQ ID NO:8), SLLTEVETLIRNGWGCRCSDSSD (SEQ ID NO:9), SLLTEVETLTKNGWGCRCSDSSD (SEQ ID NO:10), SLLTEVETPIRSEWGCRYNDSSD (SEQ ID NO:11), SLLTEVETPTRNGWECKCSDSSD (SEQ ID NO:12), SLLTEVETHTRNGWECKCSDSSD (SEQ ID NO:13), SLLTEVKTPTRNGWECKCSDSSD (SEQ ID NO:14), SLLTEVETLTRNGWGCRCSDSSD (SEQ ID NO:15), SLLTEVETPTRDGWECKCSDSSD (SEQ ID NO:16), SLLTEVETPTRNGWGCRCSDSSD (SEQ ID NO:17), SLLTEVETPTRNGWECKCNDSSD (SEQ ID NO:18), SLLTEVETLTRNGWECKCSDSSD (SEQ ID NO:19), SLLTEVETPIRNEWGCKCNDSSD (SEQ ID NO:20), SFLTEVETPIRNEWGCRCNGSSD (SEQ ID NO:21), SLLTEVETPTRNGWECRCNDSSD (SEQ ID NO:22), SLLTEVETPIRKGWECNCSDSSD (SEQ ID NO:23), SLLTEVETPTRNEWECRCSDSSD (SEQ ID NO:24), SLLTGVETHTRNGWGCKCSDSSD (SEQ ID NO:25) and SLLPEVETHTRNGWGCRCSDSSD (SEQ ID NO:26).

As used herein, the term "minimal binding sequence," when used in reference to an M2 peptide, means a contiguous amino acid sequence of M2 peptide (e.g., SEQ ID NO:1) that is minimally required for binding of the anti-M2 antibody to M2 peptide. A minimal binding sequence is determined by creating various peptides consisting of N-terminal truncated M2 peptide, and C-terminal truncated M2 peptide, and measuring antibody binding to these peptides based on the method described in Example 3. Thus, a minimal binding sequence represents the N-terminal and C-terminal borders of a sequence within M2 peptide that is minimally required for antibody binding to the peptide. As disclosed in Example 3, exemplary minimal binding sequences include for Z3G1, LLTEVETPIR (SEQ ID NO:1).

A minimal binding sequence (MBS) contains all or a part of an epitope to which the M2 antibody paratope binds, sufficient to mediate anti-M2 antibody binding. An epitope contains 3-4 or more amino acid sequences, contiguous or non-contiguous, within a minimal binding sequence, that mediates antibody binding.

The term "the same minimal binding sequence" means that the minimal binding sequence of an antibody is identical to that of a reference antibody. Thus, an M2 antibody having the same minimal binding sequence as antibody denoted as Z3G1 specifically binds to the same minimal binding sequence as the M2 antibody denoted as Z3G1. The term "substantially same minimal binding sequence," and grammatical variations thereof, means a minimal binding sequence of an antibody having a single amino acid addition or deletion at N-terminus and/or C-terminus as compared to the minimal binding sequence of the reference antibody. Thus, an M2 antibody having substantially the same minimal binding sequence as antibody denoted as Z3G1 specifically binds to a minimal binding sequence having a single amino acid addition or deletion at N-terminus and/or C-terminus relative to the minimal binding sequence for M2 antibody denoted as Z3G1.

As a non-limiting illustration of antibodies that bind to the same or substantially the same minimal binding sequence, the minimal binding sequence for Z3G1 is LLTEVETPIR (SEQ ID NO:1). Thus, an antibody having the same minimal binding sequence as Z3G1 will have the LLTEVETPIR (SEQ ID NO:1) minimal binding sequence. A substantially the same minimal binding sequence of Z3G1 could be, for example, LTEVETPI (SEQ ID NO:27), LLTEVETPI (SEQ ID NO:28), SLLTEVETPIR (SEQ ID NO:29), LLTEVETPIRN (SEQ ID NO:30), LTEVETPIR (SEQ ID NO:31), etc. Thus, an antibody that binds to substantially the same minimal binding sequence as Z3G1 could therefore bind to, for example, any of LTEVETPI (SEQ ID NO:27), LLTEVETPI (SEQ ID NO:28), SLLTEVETPIR (SEQ ID NO:29), LLTEVETPIRN (SEQ ID NO:30), LTEVETPIR (SEQ ID NO:31), etc. The invention therefore provides antibodies having the same or substantially the same minimal binding sequence as anti-M2 antibodies exemplified herein, Z3G1.

To obtain anti-M2 antibodies that have the same or substantially same minimal binding sequence as another anti-M2 antibody, antibodies that compete for the binding of the antibody to M2 peptide are screened using a conventional competition binding assay. Screened antibodies are selected that have the same or substantially same minimal binding sequence as a reference antibody, as described in Example 3. As a non-limiting example, for Z3G1, at the first step, antibodies that compete with Z3G1 in the binding to M2 peptide are screened among anti-M2 antibodies using a competition binding assay. In the second step, antibodies that compete for Z3G1 binding to M2 are selected on the ability to bind to the same or substantially same minimal binding sequence as Z3G1, namely LLTEVETPIR (SEQ ID NO:1) minimal binding sequence, or a substantially the same minimal binding sequence, for example, LTEVETPI (SEQ ID NO:27), LLTEVETPI (SEQ ID NO:28), SLLTEVETPIR (SEQ ID NO:29), LLTEVETPIRN (SEQ ID NO:30), LTEVETPIR (SEQ ID NO:31), etc.

Invention M2 antibodies also include human, humanized and chimeric antibodies having the same binding affinity and having substantially the same binding affinity as the M2 antibodies exemplified herein. For example, an M2 antibody of the invention may have an affinity greater or less than 2-5, 5-10, 10-100, 100-1000 or 1000-10,000 fold affinity or any numerical value or range or value within such ranges, as the reference antibody. Thus, in additional embodiments the invention provides M2 antibodies having the same binding affinity and having substantially the same binding affinity as the antibodies denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA), provided that the heavy or light chain sequence, or subsequence thereof has the binding specificity of no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA).

Binding affinity can be determined by association ($K_a$) and dissociation ($K_d$) rate. Equilibrium affinity constant, K, is the ratio of $K_a/K_d$. As used herein, the term "the same," when used in reference to antibody binding affinity, means that the dissociation constant ($K_d$) is within about 1 to 100 fold of the reference antibody (1-100 fold greater affinity or 1-100 fold less affinity, or any numerical value or range or value within such ranges, than the reference antibody). The term "substantially the same" when used in reference to antibody binding affinity, means that the dissociation constant ($K_d$) is within about 5 to 5000 fold of the reference antibody (5-5000 fold greater affinity or 5-5000 fold less affinity than the reference antibody). The term "the same," when used in reference to association constant ($K_a$) is within about 1 to 100 fold of the reference antibody (within 1-100 fold greater or 1-100 fold less than the association constant, $K_a$, of the reference antibody). The term "substantially the same" when used in reference to association constant ($K_a$), means that the association constant is within about 5 to 5000 fold greater or less than the association constant, $K_a$, of the reference antibody (5-5000 fold greater or 5-5000 fold less than the reference antibody).

At least a part of binding affinity can be when the antibody has less affinity, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or less (e.g., $K_d$), or any numerical value or range of values within such ranges. At least a part of binding affinity can be when the antibody has more affinity, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or more (e.g., $K_d$), or any numerical value or range of values within such ranges.

Association ($K_a$) and dissociation ($K_d$) rates can be measured using surface plasmon resonance (SPR) (Rich and Myszka, *Curr. Opin. Biotechnol* 11:54 (2000); Englebienne, *Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)). $K_d$ values for the exemplary antibodies set forth herein are defined as the antibody concentration required to saturate one half (50%) of the binding sites on the M2 antigen on the surface of either A/PR/8/34 or A/HK/1/68 infected MDCK cells.

Additional antibodies included in the invention have a binding specificity of the antibodies denoted as no. Z3G1 (ATCC Deposit No. PTA-5967; deposited Mar. 13, 2004, American Type Culture Collection, Manassas, Va., USA) and no. Z3G3(Z3.16.25.1) (ATCC Deposit No. PTA-5968; deposited Mar. 13, 2004, American Type Culture Collection, Manassas, Va., USA), and binding affinity for M2 with a dissociation constant ($K_d$) less than $5\times10^{-2}$ M, $10^{-2}$ M, $5\times10^{-3}$ M, $10^{-3}$ M $5\times10^{-4}$ M, $10^{-4}$ M $5\times10^{-5}$M, $10^{-5}$M $5\times10^{-6}$ M, $10^{-6}$ M $5\times10^{-7}$ M, $10^{-7}$ M $5\times10^{-8}$ M, $10^{-8}$ M $5\times10^{-9}$ M, $10^{-9}$ M $5\times10^{-10}$ M, $10^{-10}$ M $5\times10^{-11}$ M, $10^{-11}$ M $5\times10^{-12}$ M, $10^{-12}$ M $5\times10^{-13}$ M, $10^{-13}$ M $5\times10^{-14}$ M, $10^{-14}$ M $5\times10^{-15}$ M, and $10^{-15}$ M. Antibodies further included in the invention bind to an epitope to which the antibodies denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, deposited Mar. 13, 2004, American Type Culture Collection, Manassas, Va., USA) bind. Yet additional antibodies have an EC50 less than 2.0 to 3.0, 1.0 to 2.0, 0.5 to 1.0, 0.1 to 0.5 or less than 0.1 μg/ml (e.g., 0.05 to 0.1 μg/ml) for inhibiting influenza A virus infection of MDCK cells, as determined by a cell based-ELISA assay.

Invention human M2 antibodies include antibodies having at least a part of one or more anti-influenza activities of the M2 antibodies exemplified herein (e.g., inhibit influenza virus infection of a cell in vitro or in vivo, inhibit influenza virus proliferation or replication, decrease one or more symptoms or complications associated with influenza virus infection, decrease susceptibility to influenza virus infection, accelerate recovery from influenza virus infection, etc.). Thus, in additional embodiments the invention provides M2 antibodies having at least a part of one or more anti-influenza activities of the antibodies denoted as no. Z3G1 (ATCC Deposit No. PTA-5967; deposited Mar. 13, 2004, American Type Culture Collection, Manassas, Va., USA) or no, Z3G3 (Z3.16.25.1) (ATCC Deposit No. PTA-5968; deposited Mar. 13, 2004, American Type Culture Collection, Manassas, Va., USA).

The term "activity," when used in comparing an antibody to a reference antibody, means that the antibody has at least a part of an activity as the reference antibody, for example, binding affinity (e.g., $K_d$), binding specificity or anti-influenza activity. Thus, an antibody having an activity of the M2 antibody denoted as Z3G1 has at least a part of one or more activities of the M2 antibody denoted as Z3G1. The term "at least a part" means that the antibody may have less activity but the antibody retains at least a measurable or detectable amount of the activity of the reference M2 antibody, e.g., at least partial binding affinity for M2, at least partial anti-influenza activity, etc. Invention human M2 antibodies having at least a part of one or more anti-influenza activities of the M2 antibodies exemplified herein may also have a greater activity than a reference antibody, such as M2 antibodies exemplified herein.

Antibodies having an activity of exemplified human M2 antibodies can be identified through various methods disclosed herein or known in the art. For example, using binding assay with plate-bound M2 peptide as a coating antigen (ELISA), binding assay to M2 protein on viral infected MDCK cells (cell based ELISA), and specific inhibition of antibody binding to M2 on the viral infected MDCK cells with M2 peptide (M2e). Additional assays include in vitro cell infectivity assays with influenza virus (Zebedee et al., *J. Virology* 62:2762 (1988)) as well as in vivo animal assays as set forth in Examples 1, 3 and 4.

Methods of producing human polyclonal and monoclonal antibodies are disclosed herein and known in the art. For example, as disclosed herein a mixture of proteins, M2 peptide and M2SG peptide conjugated to KLH or BSA, were used to immunize human transchromosomic KM Mice™ (WO 02/43478) or HAC mice (WO 02/092812). KM Mice™ or HAC mice express human immunoglobulin genes. Using conventional hybridoma technology, splenocytes from immunized mice that were high responders to M2 antigen were isolated and fused with myeloma cells. A monoclonal antibody was obtained, denoted no. Z3G1, that reacted to M2 peptide and/or M2-BSA conjugates, but did not bind to the BSA or KLH carriers. An overview of the technology for producing human antibodies is described in Lonberg and Huszar (*Int. Rev. Immunol.* 13:65 (1995)). Transgenic animals with one or more human immunoglobulin genes (kappa or lambda) that do not express endogenous immunoglobulins are described, for example in, U.S. Pat. No. 5,939,598. Additional methods for producing human polyclonal antibodies and human monoclonal antibodies are described (see, e.g., Kuroiwa et al., *Nat. Biotechnol* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

M2 monoclonal antibodies can also be readily generated using other techniques including hybridoma, recombinant, and phage display technologies, or a combination thereof (see U.S. Pat. Nos. 4,902,614, 4,543,439, and 4,411,993; see, also *Monoclonal Antibodies Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Suitable techniques that additionally may be employed in the method including M2 affinity purification, non-denaturing gel purification, HPLC or RP-HPLC, purification on protein A column, or any combination of these techniques. The antibody isotype can be determined using an ELISA assay, for example, a human Ig can be identified using mouse Ig-absorbed anti-human Ig.

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l Acad. Sci. USA* 81:6851 (1984); Boulianne et al., *Nature* 312:643 (1984); Capon et al., *Nature* 337:525 (1989); and Traunecker et al., *Nature* 339:68 (1989).

M2 protein suitable for generating antibodies can be produced by any of a variety of standard protein purification or recombinant expression techniques known in the art. For example, M2 can be produced by standard peptide synthesis techniques, such as solid-phase synthesis. A portion of the protein may contain an amino acid sequence such as a T7 tag or polyhistidine sequence to facilitate purification of expressed or synthesized M2. M2 may be expressed in a cell and protein produced by the cells may be purified. M2 protein may be expressed as a part of a larger protein by recombinant methods.

Forms of M2 suitable for generating an immune response include peptide subsequences of full length M2, such as M2e (e.g., typically four to five amino acids or more in length). Additional forms of M2 include M2 containing preparations or extracts, partially purified M2 as well as cells or viruses that express M2 or preparations of such expressing cells or viruses.

Animals which may be immunized include mice, rabbits, rats, sheep, cows or steer, goats, or guinea pigs; such animals include those genetically modified to include human IgG gene loci. Such animals can therefore be used to produce human antibodies in accordance with the invention. Additionally, to increase the immune response, M2 can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of M2 antigen preparation, and may be at regular or irregular intervals.

Thus, in another embodiment, the invention provides methods of producing human M2 antibodies, including antibodies having one or more an anti-influenza activities, such as inhibiting influenza virus infection, replication, proliferation, or titer, or inhibiting increases in virus replication, proliferation or titer, or reducing the progression, severity, frequency, duration or probability of one or more symptoms or complications associated with influenza infection, or susceptibility to infection, or having broad reactivity against various influenza virus strains or isolates. In one embodiment, a method includes administering M2 or an immunogenic fragment thereof to an animal (e.g., a mouse, cow or steer) capable of expressing human immunoglobulin; screening the animal for expression of human M2 antibody; selecting an animal that produces a human M2 antibody; isolating an antibody from the animal that produces human M2 antibody; and determining whether the human M2 antibody binds to M2. In another embodiment, a method includes administering human M2 or an immunogenic fragment thereof to an animal (e.g., a mouse, cow or steer) capable of expressing human immunoglobulin; isolating spleen cells from the mouse that produces human M2 antibody; fusing the spleen cells with a myeloma cell to produce a hybridoma; and screening the hybridoma for expression of a human M2 antibody that has an anti-influenza activity.

The invention further provides human M2 antibodies that have been modified. Examples of modifications include one or more amino acid substitutions, additions or deletions of the antibody, provided that the modified antibody has all or at least part of an activity of unmodified M2 antibody, e.g., binding affinity, specificity, or an anti-influenza activity, etc.

A particular example of a modification is where an antibody of the invention is altered to have a different isotype or subclass by, for example, substitution of the heavy chain constant region (see, for example, Example 2). An alteration of the Ig subclass of an M2 antibody Z3 from IgG3 to IgG1 results in an improvement in an anti-influenza activity. Thus, modifications include deleting small and large regions of amino acid sequences from an antibody and substituting the deleted region with another amino acid sequence, whether the sequence is greater or shorter in length than the deleted region.

Additional modifications of M2 antibodies included in the invention are antibody derivatives, i.e., the covalent attachment of any type of molecule to the antibody. Specific examples of antibody derivatives include antibodies that have been glycosylated, acetylated, phosphorylated, amidated, formylated, ubiquitinated, and derivatization by protecting/blocking groups and any of numerous chemical modifications.

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications further include structural and functional analogues, for example, peptidomimetics having synthetic or non-natural amino acids or amino acid analogues and derivatized forms.

Modifications include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids, lipids, etc.

Modifications include an activity or function of a reference composition (e.g., specific binding to M2). Modified antibodies having altered characteristics, such as increased binding affinity, can be produced using methods known in the art. For example, affinity maturation techniques can be used to improve antibody binding affinity (US 2004/0162413 A1; U.S. Pat. Nos. 6,656,467, 6,531,580, 6,590,079 and 5,955,358; Fiedler et al., *Protein Eng.* 15:931 (2002); Pancook et al., *Hybrid. Hybridomics* 20:383 (2001); Daugherty et al., *Protein Eng.* 11:825 (1998); Wu et al., *Proc. Nat'l Acad. Sci. USA* 95:6037 (1998); and Osbourn et al., *Immunotechnology* 2:181 (1996)).

A modified protein can have an amino acid substitution, addition or deletion (e.g., 1-3, 3-5, 5-10 or more residues). In a particular non-limiting example, the substitution is a conservative amino acid substitution.

Amino acid substitutions can be conservative or non-conservative and may be in the constant or variable region of the antibody. One or a few conservative amino acid substitutions in constant or variable regions are likely to be tolerated. Non-conservative substitution of multiple amino acids in hypervariable regions is likely to affect binding activity, specificity or antibody function or activity.

Regional mutability analysis can be used to predict the effect of particular substitutions in CDR and FR domains (Shapiro et al., *J Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Predictive models based upon QSAR can in turn be used to predict the effect of mutations. For example, the effect of mutations on the association and dissociation rate of an antibody interacting with its antigen has been used to construct quantitative predictive models for both kinetic ($K_a$ and $K_d$) constants, which can in turn be used to predict the effect of other mutations on the antibody (De Genst et al., *J. Biol. Chem.* 277:29897 (2002)).

The effect of a substitution can be assayed in order to identify antibodies retaining at least a part of the binding activity, specificity or antibody function or activity of unsubstituted antibody. For example, an amino acid substitution in a hypervariable region may be assayed for binding activity or specificity, or an anti-influenza activity. Such antibodies having amino acid substitutions are included so long as at least a part of binding affinity, binding specificity, or an anti-influenza activity of a reference antibody (e.g., unmodified human M2 antibody) is retained by the substituted antibody.

A "conservative substitution" means the replacement of one amino acid by a biologically, chemically or structurally similar residue. Biologically similar means that the substitution is compatible with biological activity, e.g., specifically binds to M2. Structurally similar means that the amino acids have side chains with similar length, such as alanine, glycine and serine, or similar size. Chemical similarity means that the residues have the same charge or are both hydrophilic or hydrophobic. Particular non-limiting examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Modified antibodies include amino acid sequence with 50-100%, or 50%, 60%, 70%, 75%, 80%, 85%, 90%, 95%, 96%, 97%, 98%, 99%, or more identity to a sequence of a monoclonal antibody denoted as no. Z3G1. The identity can be over a defined area (region or domain) of the protein.

The term "identity" and grammatical variations thereof mean that two or more referenced entities are the same. Thus, where two antibody sequences are identical, they have the same amino acid sequence. "Areas, regions or domains of identity" mean that a portion of two or more referenced entities are the same. Thus, where two antibody sequences are identical over one or more sequence regions, they share identity in these regions. The term "substantial identity" means that the identity is structurally or functionally significant. That is, the identity is such that the molecules are structurally identical or have at least one of the same functions (e.g., specific binding to M2) even though the molecules are different.

Due to variation in the amount of sequence conservation between structurally and functionally related proteins, the amount of sequence identity for substantial identity will depend upon the protein, the region and any function of that region. Although there can be as little as 30% sequence identity for proteins to have substantial identity, typically there is more, e.g., 50%, 60%, 75%, 85%, 90%, 95%, 96%, 97%, 98%, identity to a reference sequence. For nucleic acid sequences, 50% sequence identity or more typically constitutes substantial homology, but again can vary depending on the comparison region and its function, if any.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol. Biol.* 132: 185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Human monoclonal M2 antibodies of the invention include subsequences (e.g., fragments) and modified forms (e.g., sequence variants) as set forth herein. In particular embodiments, human M2 antibody subsequences include an Fab, Fab' and F(ab')2, Fd, single-chain Fvs (scFv), single-chain antibodies, disulfide-linked Fvs (sdFv) and VL or VH domain fragments. In particular aspects, an Fab, Fab' and F(ab')2, Fd, single-chain Fvs (scFv), single-chain antibodies, disulfide-linked Fvs (sdFv) and $V_L$ or $V_H$ domain subsequence has the same binding affinity, substantially the same binding affinity, the same binding specificity, or one or more anti-influenza activities, e.g., efficacy in inhibiting influenza infection of a cell in vitro or in vivo as the reference M2 antibody (e.g., the full length or unmodified M2 antibody). Individual M2-binding antibody subsequences can be combined. For example, a combination of $V_L$ or $V_H$ subsequences can be joined by a linker sequence thereby forming a $V_L$-$V_H$ chimera. A combination of single-chain Fvs (scFv) subsequences can be joined by a linker sequence thereby forming a scFv-scFv chimera. M2-binding antibody subsequences, including single-chain antibodies, include variable region(s) alone or in combination with all or a portion of other subsequences, as well as, one or more of the following: hinge region, CH1, CH2, and CH3 domains. Also included are antigen-binding subsequences of any combination of variable region(s) with a hinge region, CH1, CH2, and CH3 domains.

M2 antibody subsequences (e.g., Fab, Fab', F(ab')2, Fd, scFv, sdFv and VL or VH) of the invention can be prepared by proteolytic hydrolysis of the antibody, for example, by pepsin or papain digestion of whole antibodies. The terms "functional subsequence" and "functional fragment" when referring to an antibody of the invention refers to a portion of an antibody that retains at least a part of one or more functions or activities as the intact reference antibody.

Antibody fragments produced by enzymatic cleavage with pepsin provide a 5S fragment denoted F(ab')2. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used. Genetic techniques include expression of all or a part of the M2 antibody gene into a host cell such as Cos cells or *E. coli*. The recombinant host cells synthesize intact or single antibody chain, such as a scFv (see, e.g., Whitlow et al., In: *Methods: A Companion to Methods in Enzymology* 2:97 (1991), Bird et al., *Science* 242:423 (1988); and U.S. Pat. No. 4,946,778). Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

Additional modifications of M2 antibodies included in the invention are antibody additions/insertions. For example, an addition can be the covalent or non-covalent attachment of any type of molecule to the antibody. Specific examples of antibody additions include glycosylation, acetylation, phosphorylation, amidation, formylation, ubiquitinatation, and derivatization by protecting/blocking groups and any of numerous chemical modifications.

Additions further include fusion (chimeric) polypeptide sequences, which is an amino acid sequence having one or more molecules not normally present in a reference native (wild type) sequence covalently attached to the sequence. A particular example is an amino acid sequence of another antibody to produce a multispecific antibody.

Another particular example of a modified M2 antibody having an amino acid addition is one in which a second heterologous sequence, i.e., heterologous functional domain is attached that confers a distinct or complementary function upon the antibody. For example, an amino acid tag such as T7 or polyhistidine can be attached to M2 antibody in order to facilitate purification or detection of M2 or influenza virus(es). Yet another example is an antiviral attached to an M2 antibody in order to target cells infected with influenza for virus killing, proliferation inhibition, replication inhibition, etc. Thus, in other embodiments the invention provides M2 antibodies and a heterologous domain, wherein the domain confers a distinct function, i.e., a heterologous functional domain, on the antibody.

Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), metals (gold, silver), etc.

Linker sequences may be inserted between the antibody sequence and the heterologous functional domain so that the two entities maintain, at least in part, a distinct function or activity. Linker sequences may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Additional examples of heterologous functional domains are detectable labels. Thus, in another embodiment, the invention provides human M2 antibodies that are detectably labeled.

Specific examples of detectable labels include fluorophores, chromophores, radioactive isotopes (e.g., S35, P32, I125), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified. Ligands may bind other molecules such as biotin, which may bind avidin or streptavidin, and IgG, which can bind protein A.

It is understood that a M2 antibody may have two or more variations, modifications or labels. For example, a monoclonal antibody may be coupled to biotin to detect its presence with avidin as well as labeled with I125 so that it provides a detectable signal. Other permutations and possibilities will be readily apparent to those of ordinary skill in the art, and are considered to be within the scope of the invention.

The invention further provides nucleic acids encoding the human M2 antibodies of the invention, including modified forms, subsequences/fragments, chimeras, etc. In particular embodiments, a nucleic acid encodes intact or single chain M2 antibody denoted as no. Z3G1 (ATCC Deposit No. PTA-5967; deposited Mar. 13, 2004, American Type Culture Collection, Manassas, Va., USA) and no. Z3G3 (Z3.16.25.1) (ATCC Deposit No. PTA-5968; deposited Mar. 13, 2004, American Type Culture Collection, Manassas, Va., USA). In additional embodiments, a nucleic acid encodes intact or single chain as set forth in Example 1 (SEQ ID NOs:34, 35 and 37).

The terms "nucleic acid" or "polynucleotide" are used interchangeably to refer to all forms of nucleic acid, including deoxyribonucleic acid (DNA) and ribonucleic acid (RNA). The nucleic acids can be double, single strand, or triplex, linear or circular. Nucleic acids include genomic DNA, cDNA, and antisense. RNA nucleic acid can be spliced or unspliced mRNA, rRNA, tRNA or antisense. Nucleic acids of the invention include naturally occurring, synthetic, as well as nucleotide analogues and derivatives. Such altered or modified polynucleotides include analogues that provide nuclease resistance, for example.

Nucleic acid can be of any length. For example, a subsequence of any of no. Z3G1 (ATCC Deposit No. PTA-5967; deposited Mar. 13, 2004, American Type Culture Collection, Manassas, Va., USA) or no. Z3G3 (Z3.16.25.1) (ATCC Deposit No. PTA-5968; deposited Mar. 13, 2004, American Type Culture Collection, Manassas, Va., USA), that encodes a protein having one or more anti-influenza activities. In a particular embodiment, a nucleic acid includes a heavy-chain sequence and light-chain sequence as set forth in Example 1 (SEQ ID NOs:32, 33 and 36). In another particular embodiment, a nucleic acid encodes a heavy-chain sequence and light-chain sequence as set forth in Example 1 (SEQ ID NOs:34, 35 and 37).

As a result of the degeneracy of the genetic code, nucleic acids include sequences that are degenerate with respect to sequences encoding no. Z3G1 (ATCC Deposit No. PTA-5967; deposited Mar. 13, 2004, American Type Culture Collection, Manassas, Va., USA) and no. Z3G3(Z3.16.25.1) (ATCC Deposit No. PTA-5968; deposited Mar. 13, 2004, American Type Culture Collection, Manassas, Va., USA) subsequences thereof and modified forms as set forth herein.

Nucleic acid can be produced using any of a variety of well known standard cloning and chemical synthesis methods and can be altered intentionally by site-directed mutagenesis or other recombinant techniques known to those skilled in the art. Purity of polynucleotides can be determined through sequencing, gel electrophoresis and the like.

Nucleic acids of the invention may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

The nucleic acids of the invention may be inserted into a plasmid for propagation into a host cell and for subsequent genetic manipulation if desired. A plasmid is a nucleic acid that can be stably propagated in a host cell; plasmids may optionally contain expression control elements in order to drive expression of the nucleic acid encoding M2 antibody in the host cell. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of M2 antibody encoding nucleic acids, producing M2 antibodies or antisense, and expressing the M2 antibodies in host cells or organisms, for example.

Nucleic acids encoding variable regions of the antibody heavy and light chains, or encoding fill length antibody heavy and light chains can be isolated from a hybridoma. Isolated nucleic acids may be inserted into a suitable expression vector, and introduced into suitable host cells such as yeast or CHO cells which can be cultured for the production of recombinant M2 antibodies.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a M2 antibody in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In. *Current Protocols in Molecular Biology*, Vol. 2, Ch. 13, ed., Greene Publish. Assoc. & Wiley Interscience, 1988; Grant et al. *Methods in Enzymology,* 153: 516 (1987), eds. Wu & Grossman; Bitter *Methods in Enzymology,* 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 kb).

Host cells including nucleic acids encoding human M2 antibodies are also provided. In one embodiment, the host cell is a prokaryotic cell. In another embodiment, the host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded M2 antibody expressed. The term also includes any progeny or subclones of the host cell. Progeny cells and subclones need not be identical to the parental cell since there may be mutations that occur during replication and proliferation. Nevertheless, such cells are considered to be host cells of the invention.

Host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression, are provided.

Expression vectors also can contain a selectable marker conferring resistance to a selective pressure or identifiable marker (e.g., β-galactosidase), thereby allowing cells having the vector to be selected for, grown and expanded. Alternatively, a selectable marker can be on a second vector that is cotransfected into a host cell with a first vector containing an invention polynucleotide.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk-, hgprt- or aprt-cells, respectively. Additionally, antimetabolite resistance can be used as the basis of selection for dhfr, which confers resistance to methotrexate (O'Hare et al., *Proc. Nail. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1 (1981)); puromycin; and hygromycin gene, which confers resistance to hygromycin (Santerre et al., Gene 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

Methods for treating influenza virus infection of a subject include administering to the subject an amount of a human, humanized or chimeric antibody that specifically binds influenza M2 protein effective to treat influenza virus infection of the subject. The antibody can be administered prior to infection, i.e., prophylaxis, substantially contemporaneously with infection, or following infection of the subject, i.e., therapeutic treatment.

Methods of the invention include providing a therapeutic benefit to a subject, for example, reducing or decreasing progression, severity, frequency, duration or probability of one or more symptoms or complications associated with influenza virus infection, reducing or inhibiting increases in virus titer, virus replication, virus proliferation, or an amount of a viral protein of one or more influenza virus strains or isolates, or stabilizing the condition (i.e., preventing or inhibiting worsening of a symptom or complication associated with influenza virus infection, or progression of the infection). Symptoms or complications associated with influenza virus infection whose progression, severity, frequency, duration or probability can be reduced or decreased include, for example, chills, fever, cough, sore throat, nasal congestion, sinus congestion, nasal infection, sinus infection, body ache, head ache, fatigue, pneumonia, bronchitis, ear infection or ear ache. A therapeutic benefit can also include reducing susceptibility of a subject to influenza virus infection or hastening or accelerating a subject's recovery from influenza virus infection.

In one embodiment, a method includes administering to the subject an amount of a human, humanized or chimeric antibody that specifically binds influenza virus M2 effective to inhibit virus infection of the subject or reduce susceptibility of the subject to virus infection by one or more influenza virus strains/isolates or subtypes. In various aspects, the antibody is administered prior to (prophylaxis), substantially contemporaneously with or following infection of the subject (therapeutic). The antibody can provide a therapeutic benefit which includes, for example, reducing or decreasing progression, severity, frequency, duration or probability of one or more symptoms or complications of influenza virus infection (e.g., chills, fever, cough, sore throat, nasal congestion, sinus congestion, nasal infection, sinus infection, body ache, head ache, fatigue, pneumonia, bronchitis, ear infection or ear ache), virus titer or an amount of a viral protein of one or more influenza virus strains/isolates or subtypes, or susceptibility of a subject to infection by one or more influenza virus strains/isolates or subtypes.

Therapeutic benefits and therefore methods for preventing or inhibiting an increase in influenza virus titer, virus replication, virus proliferation or an amount of an influenza viral protein in a subject are further provided. In one embodiment, a method includes administering to the subject an amount of a human, humanized or chimeric antibody that specifically binds influenza M2 effective to prevent an increase in influenza virus titer, virus replication or an amount of an influenza viral protein of one or more influenza strains/isolates or subtypes in the subject.

Methods for protecting a subject from infection, decreasing susceptibility of a subject to infection and hastening or accelerating a subject's recovery from infection by one or more influenza strains/isolates or subtypes are additionally provided. In one embodiment, a method includes administering to the subject an amount of a human, humanized or chimeric antibody that specifically binds influenza M2 effective to protect the subject from virus infection, effective to decrease susceptibility of the subject to virus infection or hastening or accelerating a subject's recovery from virus infection, by one or more influenza virus strains/isolates or subtypes.

Methods of the invention can be practiced with any antibody having the binding specificity or the same or substantially the same binding affinity of an antibody produced by a cell line (e.g., a hybridoma or a CHO cell line) denoted as no. Z3G1 (ATCC Deposit No. PTA-5967; deposited Mar. 13, 2004, American Type Culture Collection, Manassas, Va., USA) or no. Z3G3 (Z3.16.25.1) (ATCC Deposit No. PTA-5968; deposited Mar. 13, 2004, American Type Culture Collection, Manassas, Va., USA). Methods of the invention can be practiced with any antibody that recognizes the same epitope or the same or substantially the same minimal binding sequence to which an antibody denoted as no. Z3G1 (ATCC Deposit No. PTA-5967; deposited Mar. 13, 2004, American Type Culture Collection, Manassas, Va., USA) or no. Z3G3 (Z3.16.25.1) (ATCC Deposit No. PTA-5968; deposited Mar. 13, 2004, American Type Culture Collection, Manassas, Va., USA) binds.

Methods of the invention, including therapeutic, diagnostic and purification/isolation methods are applicable to any influenza strain/isolate or subtype, or combination of strains/isolates or subtypes. Particular non-limiting examples of influenza strains are A/PR/8/34 (H1N1) or A/HK/1/68 (H3N2) strain/isolate, or subtypes, such as H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 or H5N3.

Human, humanized and chimeric M2 antibodies of the invention may be used alone or in combination with therapeutic agents having anti-influenza activity, e.g., that inhibit influenza virus infection, replication, proliferation, or reduce the progression, severity, frequency, duration or probability of one or more symptoms or complications associated with influenza virus infection. Examples of such combinations include pooled monoclonal or pooled polyclonal antibodies containing two or more different M2 antibodies with different binding specificity, binding affinity, or efficacy in inhibiting influenza virus infection of a cell in vitro or in vivo Accordingly, combination compositions including M2 antibodies are provided, as well as methods of using such combinations in accordance with the methods of the invention.

The methods of the invention, including treating influenza or a disorder or complication associated with influenza virus infection, likely results in an improvement in the subjects' condition, a reduction of the progression, severity, frequency, duration or probability of one or more symptoms or complications associated with influenza virus infection, or decreasing the subject's risk for developing symptoms or contracting the infection, e.g., susceptibility to influenza virus infection. An improvement therefore includes one or more decreased or reduced virus proliferation, replication, or titer, or symptoms or complications associated with influenza virus infection. An improvement also includes reducing or eliminating the need, dosage frequency or amount of an antiviral drug or other agent used for treating a subject having or at risk of having an influenza virus infection, or a symptom or complication associated with influenza virus infection.

An improvement need not be complete ablation of any or all symptoms or complications associated with influenza virus infection. Rather, treatment may be any objective or subjective measurable or detectable anti-influenza virus effect or improvement. Thus, a satisfactory clinical endpoint is achieved when there is an incremental improvement or a partial reduction in the subjects condition or associated symptoms or complications, or an inhibition of worsening or progression of the condition (stabilizing one or more symptoms or complications), over a short or long duration (hours, days, weeks, months, etc.).

In the methods of the invention in which improvement is a desired outcome, such as a prophylactic or therapeutic treatment of a subject that provides an objective or subjective benefit as set forth herein for influenza virus, an antibody can be administered in a sufficient or effective amount. As used herein, an "amount sufficient" or "amount effective" refers to an amount that provides, in single or multiple doses, alone or in combination with one or more other treatments, therapeutic regimens or agents (e.g., a drug), a long or short term detectable response, a desired outcome or beneficial effect in a given subject of any measurable or detectable degree or for any duration (e.g., for minutes, hours, days, months, years, or cured).

An amount sufficient or an amount effective can but need not be provided in a single administration and can but need not be administered alone or in combination with another compound, agent, treatment or therapeutic regimen. In addition, an amount sufficient or an amount effective need not be sufficient or effective if given in single or multiple doses without a second compound, agent, treatment or therapeutic regimen, since additional doses, amounts or duration above and beyond such doses, or additional drugs, agents, treatment or therapeutic regimens may be included in order to be effective or sufficient in a given subject. Further, an amount sufficient or an amount effective need not be effective in each and every subject prophylactically or therapeutically treated, nor a majority of treated subjects in a given group or population. An amount sufficient or an amount effective means sufficiency or effectiveness in a particular subject, not a group or the general population. As is typical for such methods, some subjects will exhibit a greater or less response to a treatment method.

Subjects appropriate for treatment include those having or at risk of having influenza virus infection. Target subjects also include those at risk of developing an influenza associated symptom or complication. The invention methods are therefore applicable to treating a subject who is at risk of influenza virus infection or a complication associated with influenza virus infection. Prophylactic methods are therefore included.

"Prophylaxis" and grammatical variations thereof mean a method in accordance with the invention in which contact, administration or in vivo delivery to a subject is prior to manifestation or onset of influenza infection (or an associated symptom), such that it can eliminate, prevent, inhibit, decrease or reduce the probability or susceptibility of developing a symptom of influenza infection. Target subjects for prophylaxis can be at increased risk (probability or susceptibility) of influenza infection, as set forth herein and known in the art.

At risk subjects appropriate for treatment include subjects exposed to other subjects having influenza virus, or where the risk of influenza virus infection is increased due to changes in virus infectivity or cell tropism, immunological susceptibility (e.g., an immunocompromised subject), or environmental factors. At risk subjects appropriate for treatment therefore include subjects exposed or at risk of exposure to birds in the wild or in an agricultural setting (e.g., poultry farms) which birds may or may not be infected with or carriers of influenza.

M2 antibodies can be administered in accordance with the methods as a single or multiple dose e.g., one or more times daily, weekly, monthly or annually or between about 1 to 10 weeks, or for as long as appropriate, for example, to achieve a reduction in the progression, severity, frequency, duration or probability of one or more symptoms or complications associated with influenza virus infection. Doses can vary depending upon whether the treatment is prophylactic or therapeutic, the progression, severity, frequency, duration or probability of the associated disorder or complication being treated, the type of influenza isolate/strain or subtype to which treatment is directed against, the clinical endpoint desired, previous or simultaneous treatments, the general health, age, gender or race of the subject and other factors that will be appreciated by the skilled artisan. The skilled artisan will appreciate the factors that may influence the dosage and timing required to provide an amount sufficient for prophylactic or therapeutic benefit.

Typically, for therapeutic treatment, M2 antibodies will be administered within 24-72 hours after a subject is exposed to or contacted with influenza, or within 24-48 hours after development of one or more symptoms associated with virus infection. For prophylactic treatment, M2 antibodies can be administered within 0-4 weeks, e.g., 2-3 weeks, of exposure to or contact with influenza. Doses can be empirically determined, determined using animal disease models or optionally in human clinical trials. Initial study doses can be based upon the animal studies set forth herein, for a mouse, which weighs about 30 grams, the amount administered ranges between about 10-1000 µg/animal. The dose can be adjusted according to the mass of a subject, for example, about 10-50 µg/kg, 50-100 µg/kg, 100-500 µg/kg, 500-1,000 µg/kg, 1-5 mg/kg, 5-10 mg/kg, 10-20 mg/kg, 20-50 mg/kg, or more, two, three, four, or more times per hour, day, week, month or annually.

The dose amount, frequency or duration may be proportionally increased or reduced, as indicated by the status of the infection, or any adverse side effects of the treatment or therapy. Dose amounts, frequencies or duration also considered sufficient and effective and are therefore beneficial are those that result in a reduction of the use of another treatment or therapeutic regimen or protocol.

The term "subject" refers to an animal, typically mammalian, such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, the mouse model of influenza infection exemplified herein.

M2 polyclonal and monoclonal antibodies of the invention, including modified forms, variants and subsequences/fragments thereof, and nucleic acids encoding M2 antibodies, can be incorporated into pharmaceutical compositions. Such pharmaceutical compositions are useful for administration to a subject in vivo or ex vivo.

Antibodies can be included in a pharmaceutically acceptable carrier or excipient prior to administration to a subject. As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non aqueous), solutions (aqueous or non aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include respiratory system (nasal, inhalation, respiration, intubation, intrapulmonary instillation), oral, buccal, intrapulmonary, rectal, intrauterine, intradermal, topical, dermal, parenteral, sublingual, subcutaneous, intravascular, intrathecal, intraarticular, intracavity, transdermal, iontophoretic, intraocular, ophthalmic, optical, intravenous, intramuscular, intraglandular, intraorgan, intralymphatic.

Nasal and instillation formulations typically include aqueous solutions of active ingredient (compounds or agents) optionally with one or more preservative or isotonic agents. Such formulations are typically adjusted to a pH and isotonic state compatible with nasal mucous membranes. A solvent may include only water, or it may be a mixture of water and one or more other components (e.g., ethanol). Typically, the maximum ethanol is up to about 70-75%% by volume. The remaining volume may consist of water or one or more other solvents in various proportions.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Pharmaceutical compositions may therefore include preservatives, antioxidants and antimicrobial agents.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9->2-hydroxy-ethoxy methylguanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11th ed., Lippincott Williams & Wilkins, Baltimore, Md.; and Poznansky et al., *Drug Delivery Systems* (1980), R. L. Juliano, ed., Oxford, N.Y., pp. 253-315).

Antibodies and pharmaceutical compositions thereof can be packaged in unit dosage form (capsules, troches, cachets, lozenges, or tablets) for ease of administration and uniformity of dosage. "Unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compositions for transdermal administration, such as "patches" adapted to remain in contact with the epidermis of the intended recipient for an extended or brief period of time. The individual unit dosage forms can be included in multi-dose kits or containers. Pharmaceutical formulations can be packaged in single or multiple unit dosage form for ease of administration and uniformity of dosage.

The invention provides kits comprising M2 antibodies, nucleic acids encoding M2 antibodies and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., two or more human M2 antibodies alone or in combination with an antiviral agent or drug.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder or disease for which a kit component may be used. Labels or inserts can include instructions for the clinician or subject for using one or more of the kit components in a method, or treatment protocol or therapeutic regimen.

Instructions can include dosage amounts, frequency or duration, and instructions for practicing any of the methods, treatment protocols or therapeutic regimes described herein. Exemplary instructions include instructions for treating influenza infection, as set forth herein or known in the art. Kits of the invention therefore can additionally include labels or instructions for practicing any of the methods of the invention described herein including treatment, detection, monitoring or diagnostic methods. Thus, for example, a kit can include a human M2 antibody that has one or more anti-influenza activities as set forth herein, together with instructions for administering the antibody in a treatment method of the invention.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include a growth medium (e.g., for an M2 antibody producing cell line), buffering agent, or a preservative or a stabilizing agent in a pharmaceutical formulation containing a human, humanized or chimeric M2 antibody. Each component of the kit can be enclosed within an individual container and all of the various containers can be within a single package. Invention kits can be designed for cold storage. Invention kits can further be designed to contain human, humanized or chimeric M2 antibody producing hybridoma or other host cells (e.g., CHO cells). The cells in the kit can be maintained under appropriate storage conditions until the cells are ready to be used. For example, a kit including one or more hybridoma or other cells can contain appropriate cell storage medium (e.g., 10-20% DMSO in tissue culture growth medium such as DMEM, α-MEM, etc.) so that the cells can be thawed and grown.

Human, humanized and chimeric M2 antibodies of the invention are useful for isolating, detecting or purifying M2 polypeptides. Such methods include contacting a sample suspected of containing M2 (in solution, in solid phase, in vitro or in vivo, or in an intact cell or organism) with an M2 antibody under conditions allowing binding, and detecting the presence of M2, or purifying the bound M2 protein.

The invention therefore also provides methods for detecting M2 or influenza virus in a test sample. In one embodiment, a method includes contacting a sample having or suspected of having M2 or influenza virus with a human M2 antibody under conditions allowing detection of M2 in the sample and determining whether M2 is present in the test sample. Detection of M2 or influenza virus can be performed by conventional methods such as immunoprecipitation, western blotting, immunohistochemical staining or flow cytometry and ELISA.

M2 and influenza virus detection methods are useful in diagnostic protocols for detecting M2 and influenza virus. For example, where increased or decreased levels of influenza virus are associated with development, progression or regression of influenza infection, invention antibodies can be used to detect any increase or decrease in M2 or influenza virus. In addition, where it is desired to monitor levels of M2 or influenza virus following a treatment therapy that decreases M2 or influenza virus levels, invention antibodies can be used to detect such an increase or decrease in M2 or influenza virus levels before, during or following the treatment, over a long or short period of time.

The invention therefore also provides methods for detecting the presence of M2 or influenza virus in a test sample of a subject (containing biological fluid, cells, or a tissue or organ sample such as a biopsy). In one embodiment, a method includes contacting a sample having or suspected of having M2 or influenza virus obtained from a subject with a human M2 or influenza virus antibody under conditions allowing detection of M2 or influenza virus and determining whether M2 or influenza virus is present in the test sample from the subject.

Human, humanized and chimeric M2 antibodies may also be utilized to monitor the presence of M2 or influenza virus for diagnosis or following treatment of a subject, or to measure in vivo levels of M2 in subjects. For example, sputum suspected of containing M2 or influenza virus is incubated with an M2 antibody, as described above, under conditions allowing binding to occur, which detects the presence of M2 or influenza virus Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "an M2 antibody" includes a plurality of such antibodies and reference to "an anti influenza activity or function" can include reference to one or more activities or functions, and so forth.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.

Peptide synthesis and generation of peptide-BSA conjugates: M2 (SEQ ID NO:2, Table 4) and M2SG (SEQ ID NO:3, Table 4) peptides were synthesized by A & A Labs LLC (San Diego, Calif.). Purity of each peptide was determined as more than 95% by HPLC. The sequence listed as SEQ ID NO:2 (M2) is a typical sequence of extracellular 23-amino-acid peptide of influenza virus matrix M2 protein seen in many influenza A virus strains. These two peptides were conjugated to bovine serum albumin (BSA, Sigma, St. Louis, Mo.) by the EDC conjugation kit (PIERCE Biotechnology, Inc., Rockford, Ill.) according to the manufacturer's instructions. BSA-conjugated M2 and M2SG peptides were used for immunization of mice.

Amino acid sequences of peptides used in the studies of epitope determination and binding specificity of human anti-M2 antibody are listed in Tables 4 and 7. M2 mutant peptide analogues used for the analysis of the binding specificity were designed based on the sequence information of M2 mutant proteins identified in mutant influenza A virus strains, which are listed in GenBank database. The M2 analog peptides and truncated M2 peptides were synthesized by A & A Labs LLC (San Diego, Calif.).

Mice. Human trans-chromosomic mice (WO 02/43478, WO 02/092812, Ishida and Lonberg, IBC's 11th Antibody Engineering Meeting. Abstract (2000); and Kataoka, S. IBC's 13th Antibody Engineering Meeting. Abstract (2002)) harboring human chromosome fragments containing the human immunoglobulin region were obtained from Kirin Brewery Co., Ltd. (Japan). C57BL/6J mice were purchased from Jackson Laboratories at Bar Harbor, Me.

Immunization: M2-BSA and M2SG-BSA (1:1 ratio in PBS (phosphate buffered saline, GIBCO BRL, Rockville, Md.)) were mixed with an equal volume of complete Freund's adjuvant (CFA) (Sigma, St. Louis, Mo.) and an emulsion was prepared. Mice were immunized with 20 µg of the mixture in CFA subcutaneously and were boosted subcutaneously with the same amount of the mixture of M2-BSA and M2SG-BSA in incomplete Freund's adjuvant (IFA) (Sigma, St. Louis, Mo.) on day 21, and followed by the third intraperitoneal injection with RIBI (Corixa, Hamilton, Mont.) on day 42. A final intraperitoneal and intravenous injection of 10 µg of M2 peptide without adjuvant was given 3 days before fusion.

ELISA: Antibody titers and antibody specificity as well as antibody production by hybridomas were determined by ELISA. In brief, 50 µl of M2-BSA or M2 peptide were coated on a 96-well flat bottom plate (Nunc, Denmark) at a concentration of 1 µg/ml with carbonate buffer (pH 9.6) overnight at 4° C. or at 37° C. for 1 hr. After washing twice with PBS/0.1% Tween 20, plates were blocked with PBS/1% BSA (Sigma, St. Louis, Mo.) at 37° C. for 30 min., the antibody or serum was added to the wells and the plates were incubated at 37° C. for 1 hr. After washing four times, diluted HRP conjugated goat anti-human Immunoglobulin gamma chain specific antibody (Jackson Immunoresearch Laboratory, West Grove, Pa.) was added to the wells and incubated for 1 hr at 37° C. After washing four times, TMB substrate solution (DAKO, CA) was added and incubated for 30 min at room temperature. The optical density at 450 nm was measured by a microplate reader.

Isotype ELISA: The isotype of the antibody produced by the hybridomas was determined by ELISA. In brief, 50 µl of M2-BSA or M2 peptide were coated on a 96-well flat bottom plate (Nunc, Denmark) at a concentration of 1 µg/ml with carbonate buffer (pH 9.6) overnight at 4° C. or at 37° C. for 1 hr. After washing twice with PBS/0.1% Tween 20, plates were blocked with PBS/1% BSA (Sigma, St. Louis, Mo.) at room temperature for 1 hr, the antibody was added to the wells and the plates were incubated at room temperature for 1 hr. After washing three times, either of diluted HRP-conjugated mouse anti-human IgG1, IgG2, IgG3 and IgG4 heavy chain detection antibodies (Zymed, San Francisco, Calif.) was added to the wells and incubated for 1 hr at room temperature. After washing three times, TMB substrate solution (DAKO, CA) was added and incubated for 30 min at room temperature. The optical density at 450 nm was measured by a microplate reader.

Influenza A virus-infected cell-based ELISA: MDCK cells (Madin-Darby Canine Kidney epithelial cells; ATCC, Rockville, Md.) were plated in a 96-well flat bottom plate (Falcon®) at $1.5 \times 10^5$ cells/mL in MEM containing 1% non-essential amino acids, 2 mM L-glutamine, 100 U/ml penicillin and 100 µg/ml streptomycin sulfate, 1 mM sodium pyruvate (cMEM) (InVitrogen, Carlsbad, Calif.) and 150 µl per well and cultured for 48 hr at 7% CO2. After 48 hr the plate was washed twice with PBS and infected at room temperature for 30 minutes with 30 µl of 10-fold TCID50 influenza A virus (A/PR/8/34 or A/HK/1/68; ATCC, Rockville, Md.) with periodically swirling. After infection, the plate was washed once with PBS and 150 µl of 1 µg/mL trypsin (TPCK-treated, Worthington, Biochem. Corp.) in Minimal Essential Media (Invitrogen Corp, CA) was added and the plate incubated for 27 hr. After infection, the cell monolayer was washed with PBS/1% FCS (GIBCO BRL, Rockville, Md.) three times and blocked with PBS/1% BSA/5% FCS at room temperature for 30 min. The antibodies were diluted and 50 µl added to each well and incubated at room temperature for 45 min. After washing 4 times, the HRP conjugated Rabbit anti-human immunoglobulin gamma chain antibody (DAKO, Denmark) was diluted 1:3000 and 50 µl added to each well and the plate was incubated at room temperature for 30 min. After washing 5 times, 100 µl of TMB substrate (DAKO, Denmark) containing 1 mM Levamisole solution (Vector Laboratories Inc. Burlingame, Calif.) was added and the plates were incubated at room temperature for 15 min. 50 µl of supernatant were transferred to a new 96-well plate (Nunc, Denmark) containing 100 µl stop solution (1N H2SO4) and the optical density (OD) at 450 nm was measured by a microplate reader. $EC_{50}$ of each antibody was calculated as previously described (Sette et al., Nature 328:395 (1987)). The dissociation constant ($K_d$) was defined as the antibody concentration required to saturate one half (50%) of the binding sites on the M2 antigen on the surface of either A/PR/8/34 or A/HK/1/68 infected MDCK cells.

Peptide competition in Influenza A virus-infected cell-based ELISA: Virus-infected MDCK cells were prepared as described above. The M2 peptide and the anti-M2 antibodies were mixed and incubated at room temperature for 30 min. After incubation, 50 µl of the mixture of peptide and antibodies were added to cells and incubated at room temperature for 30 minutes. After washing 4 times, the HRP conjugated Rabbit anti-human immunoglobulin gamma chain antibody (DAKO, Denmark) was diluted 1:3000 and 50 µl added to each well and the plate was incubated at room temperature for 30 min. After washing for 5 times, 100 µl of TMB substrate (DAKO, Denmark) containing 1 mM Levamisole solution (Vector Laboratories Inc., Burlingame, Calif.) was added and the plates were incubated at room temperature for 15 min Fifty µl of supernatant was transferred to a new 96-well plate (Nunc, Denmark) containing 100 μl stop solution (1N H2SO4) and the optical density at 450 nm was measured by a microplate reader.

Hybridoma production: The mouse having the highest antibody titer was selected for production of monoclonal antibodies. The spleen was harvested and single cell suspension was fused to a myeloma cell line (SP2/O-Ag14) (ATCC, Rockville, Md.) at a 3:1 ratio with 50% PEG (Boehringer Mannheim, Indianapolis, Ind.). The fusions were plated onto 96-well plate at an optimal density and cultured in complete RPMI-10 medium (RPMI 1640 with 10% FCS, 1% nonessential amino acids, 2 mM L-glutamine, 50 μM 2-ME, 100 U/ml penicillin and 100 μg/ml streptomycin sulfate) in a 5% $CO_2$, 37° C. incubator. Approximately 2000 hybridoma growing wells of each fusion were screened by ELISA. Cells positive for binding to the M2 peptide were transferred to 24 well plates and 4 rounds of limiting dilutions were performed to obtain monoclonal antibodies. Anti-M2 monoclonal antibodies were further confirmed by an Influenza A virus infected cell based ELISA.

Antibody purification: For antibody purification, hybridomas were cultured in an Integra system (INTEGRA Bioscience, Inc. Ijamsville, Md.) with hybridoma-SFM (GIBCO BRL, Rockville, Md.). Human monoclonal antibodies were purified from culture media using Protein A-Sepharose Fast Flow gel (Amersham Pharmacia Cat#17-0618-02, Uppsala, Sweden). Briefly, conditioned medium, containing an appropriate amount of the antibody for the column capacity, was filtered with a 0.22 μm disk filter (Minisarto-plus, Sartorius Cat#17822, Gettingen, Germany) and loaded onto a 2.0 ml Protein A-Sepharose Fast Flow column equilibrated with phosphate buffered saline (PBS). The column was washed with more than 40 ml of PBS and the antibody was eluted with 0.1 M Gly-HCl, pH3.6, 0.15 M NaCl. After the initial 1.0 ml of the elution buffer had passed through, 3 separate elution fractions were collected at a volume of 5.0 ml/tube, and neutralized immediately with 250 μl of 1 M Tris-HCl, pH8.0. This purification procedure was repeated until all conditioned media were processed. Antibody concentration was determined with a human IgG-specific ELISA and all fractions containing the antibody were pooled and concentrated with a centrifugal concentrator (Vivaspin 20, 30,000MWCO: Sartorius Cat#VS2022, Gettingen, Germany).

In order to remove pyrogen, the concentrated sample was buffer-exchanged into 20 mM sodium phosphate, pH6.6, and loaded onto a 0.5 ml SP-Sepharose HP column (Amersham Pharmacia, Cat#17-1087-01, Uppsala, Sweden) equilibrated with the same buffer. The pyrogen was removed by first passing the sample through a 2 ml Q-Sepharose Fast Flow column (Amersham Pharmacia, Cat#17-0510-01, Uppsala, Sweden) that was connected in series to a SP-Sepharose HP column. After application, the Q-Sepharose Fast Flow column was removed and the antibody was eluted with a linear gradient ranging from 0 to 0.5 M sodium chloride. The antibody was detected at 280 nm and the antibody containing fractions pooled. The sample was concentrated with a centrifugal concentrator and buffer-exchanged into PBS by using NAP25 desalting columns (Amersham Pharmacia, Cat#17-0852-02, Uppsala, Sweden). Antibody concentration was quantitated by a human IgG specific ELISA. Pyrogen levels of samples were determined to be less than 0.13 EU/mg of protein according to a Limulus Amebocyte Lysate (LAL) assay (Associates of Cape Cod, Inc., Falmouth, Mass.).

Isolation of human anti-M2 antibody (Z3) genes: Cultured hybridoma cells (113Z-3), which produce Z3 antibody (isotype: IgG3) were collected by centrifugation. Total RNA (140 μg) was purified from these cells using RNeasy kit (QIAGEN Inc., Valencia, Calif.) following the manufacturer's instructions. SMART RACE cDNA Amplification Kit (Clontech Co., Ltd., Palo Alto, Calif.) was used for cloning of cDNA of variable region of immunoglobulin genes from total RNA of hybridoma cells as a source. Briefly, first strand cDNA was prepared by reverse transcriptase from 2 microgram of RNA. This cDNA was used as a template for polymerase chain reaction (PCR) to amplify variable region and a part of constant region of heavy chain and light chain containing leader sequences (HV and LV, respectively). The reaction was as follows: 2.5 U KOD-Plus-DNA polymerase (TOYOBO, Tokyo, Japan); 0.2 μM Primer for one side (for Heavy chain: IgG1p, for Light chain: LCR276, see Table 2); 1× Universal Primer Mix A for the other side (UMP primer Mix A attached to SMART RACE Kit); 200 μM each dNTP mix; 1 mM MgSO4; KOD-Plus-Buffer (final concentration is 1×); and cDNA template.

The thermocycling program was 94° C. for 5 min, and then 30 cycles at 94° C. for 5 sec and 68° C. for 10 sec with an extension at 72° C. for 3 min. Amplified DNA fragments were collected after ethanol precipitation and subsequent agarose gel electrophoresis, and purified by QIAquick Gel Extraction Kit (Qiagen Co., Ltd., Germany). Purified DNA fragments of NV and LV were integrated into PCR 4 Blunt-TOPO vector using Zero Blunt TOPO PCR Cloning Kit (Invitrogen, Carlsbad, Calif.), and each construct plasmid was transformed into *E. coli*, and then cloned. Nucleotide sequences of each insert (HV and LV) in construct plasmids were analyzed using specific primers (HV: M13F, M13R and hh-4, LV: M13F, M13R and LCR88, see Table 2).

Nucleotide sequences of both HV and LV from eight independent clones, respectively, were completely identical. Based on the sequence obtained from LV, oligonucleotide primers, Z3LP5BGL and Z3LP3ERI (Table 2) were designed. The light chain cDNA sequence encoding the full-length ORF (LVC), including both variable and constant regions, was obtained by PCR using the first-strand cDNA as a template, Z3LP5BGL and Z3LP3ERI as primers with KOD-Plus-DNA polymerase. Nucleotide and amino acid sequences of HV and LV are shown below.

Nucleotide Sequence of cDNA of Z3 Heavy Chain Variable Region (HV) (from Initiation Codon (ATG) to the End of Variable Region)—

```
                                                          (SEQ ID NO: 32)
ATGGACTGGA  CCTGGAGCAT  CCTTTTCTTG  GTGGCAGCAG  CAACAGGTGC  CCACTCCCAG    60

GTTCAGCTGG  TGCAGTCTGG  AGCTGAGGTG  AAGAAGCCTG  GGGCCTCAGT  GAAGGTCTCC   120

TGCAAGGCTT  CTGGTTACAC  CTTTACCAGC  TATGGTATCA  GCTGGGTGCG  ACAGGCCCCT   180

GGACAAGGGC  TTGAGTGGAT  GGGATGGATC  AGCGCTTACA  ATGGTAACAC  AAACTATGCA   240

CAGAAGCTCC  AGGGCAGAGT  CACCATGACC  ACAGACACAT  CCACGAGCAC  AGCCTACATG   300
```

-continued

```
GAGCTGAGGA GCCTGAGATC TGACGACACG GCCGTGTATT ACTGTGCGAG GGCAGCAGCT    360

GGCGGATACT TCCAGCACTG GGGCCAGGGC ACCCTGGTCA CCGTCTCCTC A             411
```

Nucleotide Sequence of cDNA of Z3 Light Chain Variable and Constant Regions (LVC) (from Initiation Codon (ATG) to the End of Constant Region (Underlined))— maceuticals, San Diego, Calif., N5KG1-Val Lark (a modified vector of N5KG1, U.S. Pat. No. 6,001,358)) which pre-digested with BglII and EcoRI (8.6 kilobases DNA fragment).

```
                                                        (SEQ ID NO: 33)
ATGGCCAGCT TCCCTCTCCT CCTCACCCTC CTCACTCACT GTGCAGGGTC CTGGGCCCAG    60

TCTGTGCTGA CTCAGCCACC CTCAGCGTCT GGGACCCCCG GGCAGAGGGT CACCATCTCT   120

TGTTCTGGAA GCAACTCCAA CATCGGAAGT AAAACTGTAA ACTGGTACCA GCAGCTCCCA   180

GGAACGGCCC CCAAACTCCT CATCTCTAGT AATAATCAGC GGCCCTCAGG GGTCCCTGAC   240

CGATTCTCTG GCTCCAAGTC TGGCACCTCA GCCTCCCTGG CCATCAGTGG GCTCCAGTCT   300

GAGGATGAGG CTGATTATTA CTGTGCAGCA TGGGATGACA GCCTGAATGG TGTGGTATTC   360

GGCGGAGGGA CCAAGCTGAC CGTCCTAGGT CAGCCCAAGG CTGCCCCCTC GGTCACTCTG   420

TTCCCACCCT CCTCTGAGGA GCTTCAAGCC AACAAGGCCA CACTGGTGTG TCTCATAAGT   480

GACTTCTACC CGGGAGCCGT GACAGTGGCC TGGAAGGCAG ATAGCAGCCC CGTCAAGGCG   540

GGAGTGGAGA CCACCACACC CTCCAAACAA AGCAACAACA AGTACGCGGC CAGCAGCTAC   600

CTGAGCCTGA CGCCTGAGCA GTGGAAGTCC CACAAAAGCT ACAGCTGCCA GGTCACGCAT   660

GAAGGGAGCA CCGTGGAGAA GACAGTGGCC CCTACAGAAT GTTCATAG                708
```

Amino Acid Sequence of cDNA of Z3 Heavy Chain Variable Region (HV) (Leader Sequence (Bold) and Variable Region)—

Nucleotide sequence of the insert of the isolated construct (N5L3G1-Z3_LF) was analyzed, and existence of the full-length ORF of Light chain (LVC) was determined. The DNA

```
                                                        (SEQ ID NO: 34)
MDWTWSILFL VAAATGAHSQ VQLVQSGAEV KKPGASVKVS CKASGYTFTS YGISWVRQAP    60

GQGLEWMGWI SAYNGNTNYA QKLQGRVTMT TDTSTSTAYM ELRSLRSDDT AVYYCARAAA   120

GGYFQHWGQG TLVTVSS                                                  137
```

Amino Acid Sequence of cDNA of Z3 Light Chain Variable and Constant Regions (LVC) (Leader Sequence (Bold), Variable Region, and Constant Region (Underlined))— sequence of the insert (LVC) was identical to Light chain variable region sequence of Z3 (LV) and human lambda immunoglobulin light chain constant region, IGLC3 (Gen-

```
                                                        (SEQ ID NO: 35)
MASFPLLLTL LTHCAGSWAQ SVLTQPPSAS GTPGQRVTIS CSGSNSNIGS KTVNWYQQLP    60

GTAPKLLISS NNQRPSGVPD RFSGSKSGTS ASLAISGLQS EDEADYYCAA WDDSLNGVVF   120

GGGTKLTVLG QPKAAPSVTL FPPSSEELQA NKATLVCLIS DFYPGAVTVA WKADSSPVKA   180

GVETTTPSKQ SNNKYAASSY LSLTPEQWKS HKSYSCQVTH EGSTVEKTVA PTECS        235
```

Generation of expression vector of isotype-changed human anti-M2 antibody (Z3-IgG1 type): The expression vector of IgG1 isotype-switched Z3 antibody (original isotype was IgG3) was constructed. Briefly, oligonucleotide primers, Z3LP5BGL and Z3LP3ERI (Table 2) containing 5'-BglII and 3'-EcoRI restriction enzyme sensitive overhang sites, respectively, were designed to amplify the full-length of Light chain (LVC) by PCR. PCR was performed using the first-strand cDNA as a template, Z3LP5BGL and Z3LP3ERI as primers with KOD-Plus-DNA polymerase. After the digestion of the PCR product by BglII and EcoRI, a 718-bp fragment was subcloned into the expression vector (IDEC Phar- Bank Accession NG_000002: *Homo sapiens* immunoglobulin lambda locus on chromosome 22).

As the second step, HV was inserted into N5L3G1-Z3_LF DNA vector as follows: the DNA vector was digested by two DNA restriction enzymes, NheI and SalI, and subsequently dephosphorylated. 9.2 kilobases DNA fragment (fragment A) was isolated. Similarly to the light chain construct, the primer set for PCR of HV was designed to have the sensitive region to these restriction enzymes in the both sides of HV. The primers are Z3HP5SAL and Z3HP3NHE (Table 2), and the construct plasmid of HV was used as a template. Purified PCR-amplified product of HV was subcloned into pGEM®-T Easy Vector System. Nucleotide sequence of the insert in the subcloned construct was confirmed. The plasmid DNA was digested by two restriction enzymes, NheI and SalI, and 0.44 kilobases DNA insert (fragment B) was isolated and purified after agarose gel electrophoresis.

Two DNA fragments A and B were ligated with T4 DNA ligase, and ligated construct (N5LG1_M2_Z3) was electroporated into E. coli ΔH5 strain to generate transformants. Positive E. coli transformants were selected. This expression vector was purified, and nucleotide sequences of both LVC and HV regions were confirmed using specific primers (SEQ ID NOs:46-49, Table 2). No mutations were introduced during the process.

Nucleotide and amino acid sequences of the full length ORF of heavy chain of Z3G1 are illustrated below. The nucleotide and amino acid sequences of the full length ORF of light chain of Z3G1 are the same of those of LVC of Z3 illustrated above.

Nucleotide Sequence of cDNA of Z3G1 Heavy Chain Variable and Constant Regions (from Initiation Codon (ATG) to the End of Constant Region (Underlined)—

(SEQ ID NO: 36)
ATGGACTGGACCTGGAGCATCCTTTTCTTGGTGGCAGCAGCAACAGGTGC

CCACTCCCAGGTTCAGCTGGTGCAGTCTGGAGCTGAGGTGAAGAAGCCTG

GGGCCTCAGTGAAGGTCTCCTGCAAGGCTTCTGGTTACACCTTTACCAGC

TATGGTATCAGCTGGGTGCGACAGGCCCCTGGACAAGGGCTTGAGTGGAT

GGGATGGATCAGCGCTTACAATGGTAACACAAACTATGCACAGAAGCTCC

AGGGCAGAGTCACCATGACCACAGACACATCCACGAGCACAGCCTACATG

GAGCTGAGGAGCCTGAGATCTGACGACACGGCCGTGTATTACTGTGCGAG

GGCAGCAGCTGGCGGATACTTCCAGCACTGGGGCCAGGGCACCCTGGTCA

CCGTCTCCTCA<u>GCTAGCACCAAGGGCCCATCGGTCTTCCCCCTGGCACCC

TCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGA

CCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGAC

CTACATCTGCAACGTGAATCACAAGCCCAGCAACACCAAGGTGGACAAGA

AAGTTGAGCCCAAATCTTGTGACAAAACTCACACATGCCCACCGTGCCCA

GCACCTGAACTCCTGGGGGGACCGTCAGTCTTCCTCTTCCCCCCAAAACC

CAAGGACACCCTCATGATCTCCCGGACCCCTGAGGTCACATGCGTGGTGG

TGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGC

TGAATGGCAAGGAGTACAAGTGCAAGGTCTCCAACAAAGCCCTCCCAGCC

CCCATCGAGAAAACCATCTCCAAAGCCAAAGGGCAGCCCCGAGAACCACA

GGTGTACACCCTGCCCCCATCCCGGGATGAGCTGACCAAGAACCAGGTCA

GCCTGACCTGCCTGGTCAAAGGCTTCTATCCCAGCGACATCGCCGTGGAG

TGGGAGAGCAATGGGCAGCCGGAGAACAACTACAAGACCACGCCTCCCGT

GCTGGACTCCGACGGCTCCTTCTTCCTCTACAGCAAGCTCACCGTGGACA

AGAGCAGGTGGCAGCAGGGGAACGTCTTCTCATGCTCCGTGATGCATGAG

GCTCTGCACAACCACTACACGCAGAAGAGCCTCTCCCTGTCTCCGGGTAA

ATGA</u>

Amino Acid Sequence of cDNA of Z3G1 Heavy Chain Variable and Constant Regions (Leader Sequence (Bold), Variable Region, and Constant Region (Underlined))—

(SEQ ID NO: 37)
MDWTWSILFLVAAATGAHSQVQLVQSGAEVKKPGASVKVSCKASGYTFTS

YGISWVRQAPGQGLEWMGWISAYNGNTNYAQKLQGRVTMTTDTSTSTAYM

ELRSLRSDDTAVYYCARAAAGGYFQHWGQGTLVTVS<u>SASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK</u>

TABLE 1

Synthesized DNA primers (SEQ ID NOS:38-51)

| No | Name | Sequence 5' to 3' | Length |
|---|---|---|---|
| (SEQ ID NO: 38) | IgG1p | TCTTGTCCACCTTGGTGTT GCTGGGCTTGTG | 31-mer |
| (SEQ ID NO: 39) | LCR276 | GGGGCCACTGTCTTCTCCA CGGTGCTC | 27-mer |
| (SEQ ID NO: 40) | hh-4 | GGTGCCAGGGGAAGACCG ATGG | 23-mer |
| (SEQ ID NO: 41) | LCR88 | CACGGCTCCCGGGTAGAAG TCACT | 24-mer |
| (SEQ ID NO: 42) | M13F | GTAAAACGACGGCCAGTG | 18-mer |
| (SEQ ID NO: 43) | M13R | CAGGAAACAGCTATGAC | 17-mer |
| (SEQ ID NO: 44) | Z3HP5SAL | AGAGAGAGAGGTCGACCCA C CATGGACTGG ACCTGG AGCA TCCTTTT | 47-mer |
| (SEQ ID NO: 45) | Z3HP3NHE | GAGAGAGG CTAGCTGA 37-mer GG AGACGGTGAC CAGGG TG | 37-mer |
| (SEQ ID NO: 46) | Z3LP5BGL | AGAGAGAG ATCTCACC AT GGCCAGCTTC CCTCT CCTCC T | 41-mer |
| (SEQ ID NO: 47) | Z3LP3ERI | AGAGAGAGAGGAATTCCTA TGAACATTCTGTAGGGGCC ACTGTC | 44-mer |
| (SEQ ID NO: 48) | SEQU1783 | GGTACGTGAACCGTCAGAT CGCCTGGA | 27-mer |
| (SEQ ID NO: 49) | SEQU4618 | TCTATATAAGCAGAGCTGG GTACGTCC | 27-mer |
| (SEQ ID NO: 50) | IgG2pG134 | TGCACGCCGCTGGTCAGGG CGCCTGAGTTCC | 31-mer |

TABLE 1-continued

Synthesized DNA primers (SEQ ID NOS:38-51)

| No | Name | Sequence 5' to 3' | Length |
|---|---|---|---|
| (SEQ ID NO: 51) | LC3F81 | TCTCATAAGTGACTTCTAC CCGGGAGC | 27-mer |

Production of recombinant human anti-M2 antibody from CHO cells: For the production of recombinant antibody, N5LG1_M2_Z3 vector containing the anti-M2 antibody was eletroporated into host cell dhfr-defective strain of Chinese Hamster Ovary cell (CHO cells, ATCC #CRL-9096) and recombinant antibody was isolated from the supernatant of the transfected cells. Briefly, ten microgram of purified DNA expression vector, N5LG1_M2_Z3, was linearized by a DNA restriction enzyme, AscI, and the DNA was transfected into $4 \times 10^6$ cells of CHO cells using a Bio Rad electroporator (350V, 500 μF). The transfected cells were seeded in 96-well culture plate, and cultured in the culture medium with Geneticin (Gibco-BRL) for selecting CHO cells containing the DNA vector. After the selection of several stable transfectant lines, high human IgG producers were screened by ELISA, and used for production of recombinant antibody.

Isolation and purification of recombinant antibody protein: CHO cells expressing recombinant antibody were cultured in a serum-free Ex-Cell 325-PE medium (JRH Bioscience, Co., Ltd.) supplemented with 2 mM glutamine, 100 units/ml penicillin, 100 μg/ml streptomycin and a hypoxanthine and thymidine (HT) supplement (1:100) (Invitrogen) in 5% $CO_2$, 37° C. incubator 20 liters of culture supernatant was used for purification of antibody protein as follows: The supernatant was applied to MabSelect Protein A column (Amersham Pharmacia Biotech, Co., Ltd.). For adsorption of antibody to protein A, phosphate-buffered saline (PBS) was used, and for elution 20 mM sodium citrate buffer and 50 mM sodium chloride (pH 2.7) was used. The pH of elution fraction was adjusted to pH5.5 by addition of 50 mM sodium phosphate buffer (pH 7.0). After the conductivity of the load material is adjusted to <4 ms/cm by adding of 1.5 volume of Milli-Q grade water (Millipore, Bedford, Mass.), the sample was first pass through a 2 ml Q-Sepharose Fast Flow column (Amersham Pharmacia, Cat# 17-0510-01, Uppsala, Sweden) that was connected with a series of a 0.5 ml SP-Sepharose HP columns (Amersham Pharmacia, Cat#17-1087-01, Uppsala, Sweden). After these steps, the Q-Sepharose Fast Flow column was removed and the antibody was eluted with PBS.

Purified antibody was sterilized by filtering with Super Cup 100 Capsule membrane filter (0.22 μm diameter pore size). The concentration of the purified antibody was measured by spectrophotometry at 280 nm, in which 1 mg/ml of protein shows 1.4 OD at 280 nm. Recombinant Z3G1 antibody (41 mg) was purified from 20 liters of CHO cell culture supernatant. Pyrogen levels of samples were determined to be less than 0.1 EU/mg of protein according to a Limulus Amebocyte Lysate (LAL) assay, Pyrocell Single Test (SEIKAGAKU Corp., Tokyo, Japan).

Virus isolation and titer measurements: For virus isolation, infected mouse lungs were removed at various days after infection, frozen in liquid nitrogen and weighed in a pre-weighed tube. Actual lung weight was calculated by subtracting tube weight and PBS was added at 1:10 ratio of weight (gram) to volume (mL) and then homogenized by using the Fisher TissueMiser (Fisher Scientific, Pittsburgh, Pa.). The sample was centrifuged for 5 minutes at 3000 rpm with Centra GP8R centrifuge (International Equipment Company, Needham Heights, Mass.) to remove cell debris. Supernatants containing virions were aliquoted and frozen in liquid nitrogen. The virus was stored at −80° C.

Virus titer was measured by a plaque assay. In brief, confluent MDCK cell monolayers in a 6-well flat bottom plate were infected with 10-fold dilutions of virus in a total volume of 100 μl in PBS for 30 minutes with periodic swirling. The monolayers were washed with PBS once and overlayed with 46° C. pre-warmed 0.9% ultra pure agarose (Invitrogen, Carlsbad, Calif.) in MEM containing 1% nonessential amino acids, 2 mM L-glutamine, 100 U/ml penicillin and 100 μg/ml streptomycin sulfate, 1 mM sodium Pyruvate (GIBCO BRL, Rockville, Md.) and 1 μg/ml of trypsin (TPCK-treated, Worthington, Biochem. Corp., Lakewood, N.J.). Cells were incubated in a 37° C., 5% CO2 incubator. The plaques were observed in 3 days postinfection and stained with 0.1% crystal violet in a 10% formaldehyde solution. The number of plaques was counted.

Example 2

This example describes characterization of human and chimeric M2 monoclonal antibodies. This example also describes data indicating that anti-M2 human monoclonal antibody Z3G1 has a broad M2 binding spectrum and is capable of high affinity binding.

Using recombinant technology, the isotype of Z3 was converted to IgG1 with the Z3 Fab, and the CHO expression system of recombinant IgG1 type Z3 (Z3G1). The methods used to produce Z3G1 antibody are as described in Example 1.

Z3G1 specifically binds to M2 peptide and M2-BSA conjugates, but did not bind to BSA, KLH (carriers for immunization) or mGAD (a synthetic irrelevant peptide derived from mouse Glutamic Acid Decarboxylase, amino acids 246 to 266) in a manner similar to original Z3.

TABLE 2

Z3G1 is specific for M2

| mAbs | M2 peptide* | M2 on infected cells** | BSA | OVA | KLH | mGAD*** |
|---|---|---|---|---|---|---|
| C40G1 | + | + | − | − | − | − |
| L66 | + | + | − | − | − | − |
| N547 | + | + | − | − | − | − |
| Z3G1 | + | + | − | − | − | − |

*Most common extracellular portion of M2 protein; the sequence is:
SLLTEVETPIRNEWGCRCNDSSD (SEQ ID NO: 1)
**M2 expressed on A/PR/8/34 and A/HK/1/68 infected MDCK cells
***A synthetic peptide derived from mouse GAD, at position from 246 to 266
+ Positive was defined as more than 2-fold higher $OD_{450\,nm}$ than control antibody or no antibody.

Binding specificity of Z3G1 was further confirmed by a cell-based ELISA. Z3G1 recognizes the extracellular/ectodomain of M2 protein (M2e) expressed on MDCK cells T0 infected with influenza virus (Table 2). Moreover, Z3G1 antibody binding to virus infected cells is specifically inhibited when M2 peptide was added (FIG. 1). Thus, Z3G1 is specific for M2 peptide and also specific for M2 protein expressed on the surface of influenza A virus-infected MDCK cells. The binding affinity of Z3G1 was slightly greater, as reflected by a relatively lower Kd value, than three other human monoclonal anti-M2 antibodies (C40G1, N547 and L66), as determined by cell-based ELISA (Table 3).

TABLE 3

Affinity comparison among human anti-M2 antibodies

| Abs | Sub-class | Light chain usage | $K_d (\times 10^{-9} M)$* PR8 infected | $K_d (\times 10^{-9} M)$* HK1 infected |
|---|---|---|---|---|
| Z3G1 | IgG1 | Lambda | 0.497 ± 0.030 | 0.488 ± 0.070 |
| C40G1 | IgG1 | kappa | 0.519 ± 0.033 | 0.542 ± 0.063 |
| N547 | IgG1 | Lambda | 1.047 ± 0.165 | 1.219 ± 0.061 |
| L66 | IgG1 | Lambda | 0.563 ± 0.099 | 0.531 ± 0.048 |

The extracellular/ecto-domain of the M2 sequence of the two virus strains in Table 3, namely A/PR/8/34 and A/PR/1/68, differs by a single amino acid: a substitution of an aspartic acid to glycine at position 20 in the extracellular portion of M2 in the A/PR/8/34 strain. The sequence derived from A/HK/1/68, which has been referred to as M2e, is shared among most influenza strains (Neirynck et al., Nature Med. 5:1157 (1999)).

Z3G1 antibody recognizes M2e proteins expressed on MDCK cells infected with both virus strains (Table 3). This conclusion is supported by the peptide ELISA data illustrated in Table 5 (+binding of Z3G1 antibody to M2 and M2G, see Table 4 for the sequences of M2 and M2G). These results indicate that Z3 recognizes both M2 and M2G proteins expressed on MDCK cells infected with these two different virus strains.

Reactivity of antibody nos. Z3G1, N547, L66, C40G1, was comparable with slightly better binding affinity (Kd) of Z3G1 (Table 3). As expected, isotype matched irrelevant human anti-HSA antibody (anti-human serum albumin) did not show any reactivity (FIG. 1).

TABLE 4

Sequences of M2 variant/mutant peptides

| M2 peptide | Sequence | SEQ ID NO |
|---|---|---|
| M2 | SLLTEVETPIRNEWGCRCNDSSD | (SEQ ID No: 2) |
| M2SG | SLLTEVETPIRSEWGCRCNDSGD | (SEQ ID No: 3) |
| M2EG | SLLTEVETPIRNEWECRCNGSSD | (SEQ ID No: 4) |
| M2P | SLPTEVETPIRNEWGCRCNDSSD | (SEQ ID No: 5) |
| M2G | SLLTEVETPIRNEWGCRCNGSSD | (SEQ ID No: 6) |
| M2DLTGS | SLLTEVDTLTRNGWGCRCSDSSD | (SEQ ID No: 7) |
| M2KNS | SLLTEVETPIRKEWGCNCSDSSD | (SEQ ID No: 8) |
| M2LGS | SLLTEVETLIRNGWGCRCSDSSD | (SEQ ID No: 9) |
| M2LTKGS | SLLTEVETLTKNGWGCRCSDSSD | (SEQ ID No: 10) |
| M2SY | SLLTEVETPIRSEWGCRYNDSSD | (SEQ ID No: 11) |
| M2TGEKS | SLLTEVETPTRNGWECKCSDSSD | (SEQ ID No: 12) |
| M2HTGEKS | SLLTEVETHTRNGWECKCSDSSD | (SEQ ID No: 13) |
| M2KTGEKS | SLLTEVKTPTRNGWECKCSDSSD | (SEQ ID No: 14) |
| M2LTGS | SLLTEVETLTRNGWGCRCSDSSD | (SEQ ID No: 15) |
| M2TDGEKS | SLLTEVETPTRDGWECKCSDSSD | (SEQ ID No: 16) |
| M2TGS | SLLTEVETPTRNGWGCRCSDSSD | (SEQ ID No: 17) |
| M2TGEK | SLLTEVETPTRNGWECKCNDSSD | (SEQ ID No: 18) |
| M2LTGEKS | SLLTEVETLTRNGWECKCSDSSD | (SEQ ID No: 19) |
| M2K | SLLTEVETPIRNEWGCKCNDSSD | (SEQ ID No: 20) |
| M2FG | SFLTEVETPIRNEWGCRCNGSSD | (SEQ ID No: 21) |
| M2TGE | SLLTEVETPTRNGWECRCNDSSD | (SEQ ID No: 22) |
| M2KGENS | SLLTEVETPIRKGWECNCSDSSD | (SEQ ID No: 23) |
| M2TES | SLLTEVETPTRNEWECRCSDSSD | (SEQ ID No: 24) |
| M2GHTGKS | SLLTGVETHTRNGWGCKCSDSSD | (SEQ ID No: 25) |
| M2PHTGS | SLLPEVETHTRNGWGCRCSDSSD | (SEQ ID No: 26) |

Underlined bold characters are the regions of mutation compared to M2 sequence of SEQ ID NO:2.

Binding activity of anti-M2 antibodies to mutant M2 peptides was analyzed with an ELISA assay using 25 different M2 peptides (SEQ ID NOs:2-26, Table 4) that have been reported in influenza A virus strains. Human anti-M2 antibody nos. Z3G1, C40G1, L66, N547 and mouse 14C2 antibody (Affinity Bioreagents, Golden, Colo.) were used in the study.

The results in Table 5 indicate that Z3G1 binds to almost all M2 mutants (except M2 GHTGKS and M2PHTGS) as well as it binds to wild type M2 peptide. This was even the case with the M2LTGEKS, which differed at six amino acid positions from the wild type M2 peptide. Whereas L66 and N547 showed relatively reduced binding to M2 mutants M2P, M2LGS and M2FG, Z3G1 binds to each of M2P, M2LGS and M2FG. Moreover, C40G1 and 14C2 exhibited no binding or reduced binding activity to M2LGS, M2LTKGS, M2HTGEKS, M2KTGEKS, M2LTGS, M2TGEK, M2LTGEKS and M2TGE but Z3G1 antibody binds to all of these variant/mutant M2 peptides. These results, which demonstrate that Z3G1 binds with high affinity to different M2 mutant peptides, indicate that Z3G1 has a broader range for binding M2e sequences than L66, N547 and C40G1. Z3G1 antibody may therefore be useful for treating various strains/isolates and subtypes of influenza A virus having different M2 sequences.

TABLE 5

Cross-reactivity of anti-M2 antibodies to M2 peptides*

| M2 analogs | Z3G1 | L66 | N547 | C40G1 | 14C2** |
|---|---|---|---|---|---|
| M2 | + | + | + | + | + |
| M2SG | + | + | + | + | + |
| M2EG | + | + | + | + | + |
| M2P | + | − | − | + | + |
| M2G | + | + | + | + | + |
| M2DLTGS | + | W | + | + | W |
| M2KNS | + | + | + | + | + |
| M2LGS | + | W | W | W | − |
| M2LTKGS | + | + | + | − | − |
| M2SY | + | + | + | + | + |
| M2TGEKS | + | + | + | + | − |
| M2HTGEKS | + | + | + | − | − |
| M2KTGEKS | + | + | + | − | − |
| M2LTGS | + | + | + | − | − |
| M2TDGEKS | + | + | + | + | − |
| M2TGS | + | + | + | W | + |
| M2TGEK | + | + | + | W | − |

TABLE 5-continued

Cross-reactivity of anti-M2 antibodies to M2 peptides*

| M2 analogs | Z3G1 | L66 | N547 | C40G1 | 14C2** |
|---|---|---|---|---|---|
| M2LTGEKS | + | + | + | W | − |
| M2K | + | + | + | + | + |
| M2FG | + | W | W | + | + |
| M2TGE | + | + | + | W | − |
| M2KGENS | + | + | + | − | + |
| M2TES | + | + | + | + | W |
| M2GHTGKS | − | + | + | − | − |
| M2PHTGS | W | + | + | − | − |

*Percentage compared relative to binding to wild-type M2 peptide (SEQ ID NO: 1):
<10%: −
10-50%: W (weak)
>50%: +
**14C2 is a commercially available mouse monoclonal antibody to M2 peptide.

TABLE 6

Binding of anti-M2 antibodies to the M2 peptide variants from recent Avian Flu outbreak

| Avian Flu | Year | Subtype | M2 variants | Z3G1 | L66 | N547 | C40G1 | 14C2 |
|---|---|---|---|---|---|---|---|---|
| Hong Kong | 1997 | H5N1 | M2DLTGS | + | W | + | + | W |
| | | | M2LTKGS | + | + | + | − | − |
| | | | M2LTGS | + | + | + | − | − |
| Hong Kong | 1999 | H9N2 | M2LTGEKS | + | + | + | W | − |
| Southeast Asia | 2004/2005 | H5N1 | M2TES | + | + | + | + | W |

The M2e sequences of recent outbreak of avian influenza A strains were derived from The Center for Disease Control (CDC) influenza A database at http://www.flu.lan1.gov/ as shown in Tables 4 and 6. M2DLTGS, M2LTKGS and M2LTGS sequences are derived from avian H5N1 influenza A viruses that emerged as a pandemic threat to humans in 1997, and M2LTGEKS and M2TES are derived from avian influenza A viruses from 1999 and 2004 outbreak, respectively. All three of these strains are highly pathogenic and caused high mortality in humans (Suzuki, *Biol. Pharm. Bull.* 28:399 (2005); Katz, *Avian Dis.* 47(3 suppl):914 (2003)). In order to identify the human antibodies that can treat these potential pandemic infections, human anti-M2 antibodies nos. Z3G1, L66, N547 and C40G1 were studied for binding to these five M2e variant peptides (Table 6).

As shown in Table 6, Z3G1 and N547 bind to all five M2e variant peptides as well as to the wild type M2 peptide. L66 bound well to most of the variants except for M2DLTGS. However, C40G1 did not bind to M2LTKGS and M2LTGS, and bound only weakly to M2LTGEKS. As a reference, a mouse monoclonal anti-M2 antibody, 14C2 only bound weakly to M2DLTGS and M2TES, and did not bind to M2LTKGS, M2LTGS and M2LTGEKS.

These results indicate that Z3G1 as well as L66 and N547 may provide a powerful strategy to treat pandemic H5N1 and H9N2 threat and other potential avian influenza outbreak.

These results also indicate that Z3G1 as well as L66 and N547 are capable of binding to a broad range of M2e peptides found among influenza A strains. Further analysis of the CDC influenza A database indicated that certain M2e sequences predominate between human and avian influenza. While wild type M2 (SEQ ID NO:2) was dominantly expressed in human influenza A strains, M2TES was commonly expressed in avian strains. Because Z3G1, L66, N547 and C40G1 could bind to M2TES, these human anti-M2 antibodies could be potential therapeutic drugs for most avian influenza strains/isolates and subtypes.

Example 3

This example includes data indicating the antigenic determinant recognized by Z3G1, which differs from those recognized by human anti-M2 monoclonal antibodies, L66, N547 and C40G1. Minimal binding sequences of antibodies were mapped using various peptides having truncations of the M2 N-terminus and C-terminus (Tables 7 and 8). The epitope of each antibody is within the minimal binding sequence.

The data indicates that the antigenic determinant (i.e. epitope) of N547 is within an amino acid sequence, LLTEVETPIRNEWGC (SEQ ID NO: 52); that the epitope recognized by L66 is within an amino acid sequence, SLLTEVETPIRNEWGC (SEQ ID NO:53); and that the epitope recognized by C40G1 is within an amino acid sequence, TPIRNE (SEQ ID NO:54)

With the N-terminal 12-amino acid peptide (NM12, SEQ ID NO:69), no or poor binding with C40G1, L66 and N547 were observed by ELISA (Table 7). In contrast, Z3G1 bound well to NM12. Further studies with a series of N-terminal peptides, positive binding to M16 (16-mer), but negative to further truncations indicated that Z3G1 tolerates one amino acid deletion from the N-terminus (i.e., Serine at position one).

Z3G1 showed significant binding to NM11, whereas the antibody did not detectably bind to NM10. Taken together, the minimal binding sequence of Z3G1 antibody was determined as LLTEVETPIR (SEQ ID NO: 1), indicating that the epitope recognized by Z3G1 is within the sequence, LLTEVETPIR (SEQ ID NO: 1). The data also indicates that antibody Z3G1 recognizes a different epitope from those of N547, L66 and C40G1 antibodies.

TABLE 7

Binding activity of anti-M2 monoclonal antibodies to M2 truncated peptides.

| M2 ID Peptide | Amino acid sequence | ELISA (OD$_{450}$)* | | | | Seq No. |
|---|---|---|---|---|---|---|
| | | Z3G1 | L66 | N547 | C40G1 | |
| M2 | SLLTEVETPIRNEWGCRCNDSSD | 2.45 | 1.04 | 1.26 | 2.38 | 1 |
| M16 | LLTEVETPIRNEWGCR | 1.73 | 0.27 | 1.68 | 1.75 | 55 |
| M15 | LTEVETPIRNEWGCR | 0.05 | 0.20 | 0.18 | 1.93 | 56 |

TABLE 7-continued

Binding activity of anti-M2 monoclonal antibodies to M2 truncated peptides.

| M2 ID | Peptide Amino acid sequence | ELISA (OD₄₅₀)* | | | | Seq No. |
|---|---|---|---|---|---|---|
| | | Z3G1 | L66 | N547 | C40G1 | |
| M12 | VETPIRNEWGCR | 0.05 | 0.19 | 0.14 | 1.95 | 57 |
| CM17 | ETPIRNEWGCRCNDSSD | 0.05 | 0.14 | 0.14 | 3.01 | 58 |
| CM16 | TPIRNEWGCRCNDSSD | 0.05 | 0.13 | 0.13 | 1.41 | 59 |
| CM15 | PIRNEWGCRCNDSSD | 0.05 | 0.13 | 0.15 | 0.10 | 60 |
| CM14 | IRNEWGCRCNDSSD | 0.05 | 0.13 | 0.13 | 0.10 | 61 |
| CM13 | RNEWGCRCNDSSD | 0.06 | 0.15 | 0.16 | 0.11 | 62 |
| CM12 | NEWGCRCNDSSD | 0.05 | 0.16 | 0.14 | 0.11 | 63 |
| NM17 | SLLTEVETPIRNEWGCR | 2.48 | 1.92 | 2.22 | 2.18 | 64 |
| NM16 | SLLTEVETPIRNEWGC | 2.38 | 2.52 | 2.78 | 2.17 | 65 |
| NM15 | SLLTEVETPIRNEWG | 1.75 | 0.28 | 0.33 | 2.67 | 66 |
| NM14 | SLLTEVETPIRNEW | 2.00 | 0.16 | 0.16 | 1.93 | 67 |
| NM13 | SLLTEVETPIRNE | 0.13 | 0.17 | 0.16 | 1.82 | 68 |
| NM12 | SLLTEVETPIRN | 1.32 | 0.12 | 0.16 | 0.16 | 69 |
| NM11 | SLLTEVETPIR | 0.69 | 0.17 | 0.15 | 0.15 | 29 |
| NM10 | SLLTEVETPI | 0.09 | 0.16 | 0.14 | 0.11 | 70 |
| NM9 | SLLTEVETP | 0.06 | 0.16 | 0.13 | 0.13 | 71 |
| NM8 | SLLTEVET | 0.06 | 0.18 | 0.15 | 0.10 | 72 |
| NM7 | SLLTEVE | 0.05 | 0.18 | 0.14 | 0.09 | 73 |

*All antibodies were used at 10 µg/ml.

TABLE 8

Minimal binding sequences of anti-M2 antibodies

| Antibody | Minimal binding sequence | SEQ ID NO |
|---|---|---|
| L66 | SLLTEVETPIRNEWG | 74 |
| C40G1 | TPIRNE | 54 |
| N547 | LLTEVETPIRNEWG | 75 |
| Z3G1 | LLTEVETPIR | 1 |

Example 4

This example describes several animal studies indicating that administering an M2 monoclonal antibody of the invention prior to infection with influenza virus protects the animal against a subsequent lethal challenge of virus.

In Vivo Efficacy of Anti-M2 Monoclonal Antibody for Prophylaxis Treatment (Prior to Virus Infection) in an Influenza a Virus Infection Model in Mice:

To evaluate the efficacy of anti-M2 human monoclonal antibody in an animal, antibody no. Z3G1 was administered at doses of 100, 30 and 10 µg/mouse intraperitoneally to female C57BL/6J mice (6-8 weeks old). One day after antibody administration, anesthetized mice (15 µl/g of Avertin (1:1 w/v of 2,2,2 tribromoethanol:tert-amyl-OH) Sigma, St. Louis, Mo.) were infected with 30 µl (3.2-fold of MLD50) of a lethal dose of influenza A/HK/1/68 (CDC, Atlanta, Ga.) intranasally. As a control, an isotype matched human monoclonal anti-HSA IgG1 antibody generated from a KM Mouse™ was used at 100 µg/mouse (Kirin Brewery Co., Ltd., Japan). Mice were observed daily for 23 days for survival. Surviving mice were sacrificed after that time and the lungs were removed for histological analysis.

Figure 2:
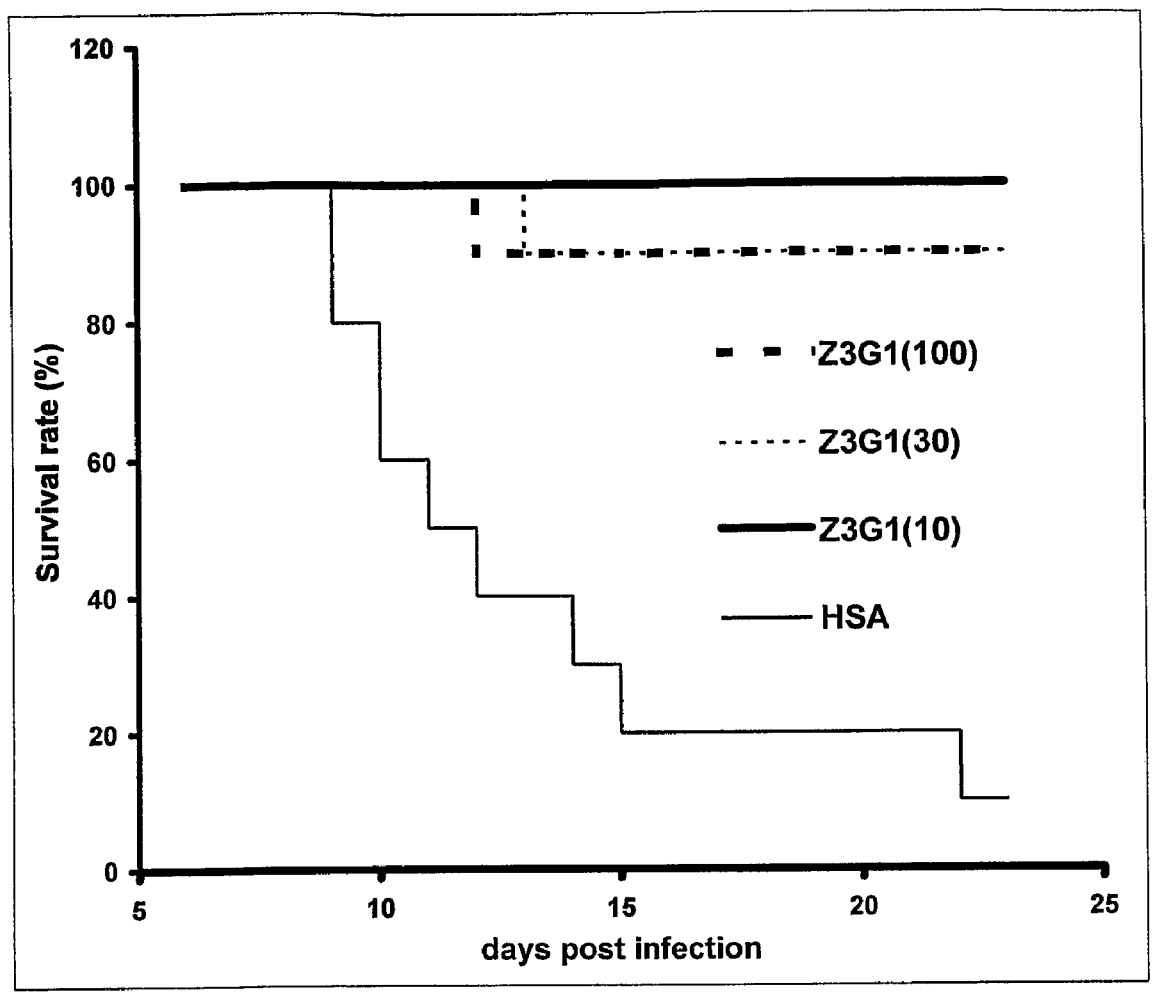
FIG. 2 shows prophylactic protection of animals from influenza virus infection-induced death by administration of M2 antibody Z3G1 (100 μg, 30 μg or 10 μg/mouse), or an isotype control antibody (HSA) at 100 μg/mouse. Z3G1 or HSA was administered one day before infection of a lethal dose of A/HK/1/68. Survival rate was measured from days 1 to 23 post infection.

Anti-M2 antibody no. Z3G1 treated mice were significantly protected even at a dose as low as 10 µg/mouse (FIG. 2). Ten of 10 mice (100%) were still alive over the 23-day period of observation. In contrast, in the control group, 9 of 10 mice (90%) died within 22 days post infection (FIG. 2).

In Vivo Inhibition of Virus Replication by Z3G1 Measured by Plaque Assay in a Mouse Influenza A Virus Infection Model:

Anesthetized female C57BL/6J mice (6-8 weeks old) were infected with 30 µl of a sub lethal dose of influenza A/HK/1/68 (CDC, Atlanta, Ga.) intranasally. Anesthetization was performed using Avertin as previously described. The lungs of infected mice were removed at day 2, 5, 7, 9, 11 to determine virus titer by a plaque assay. To determine efficacy of anti-M2 monoclonal antibody for its prophalytic treatment of influenza virus, 30 µg of Z3G1 was administered one day prior to virus infection. Isotype-matched anti-HSA IgG1 antibody was used as a control.

Figure 3:
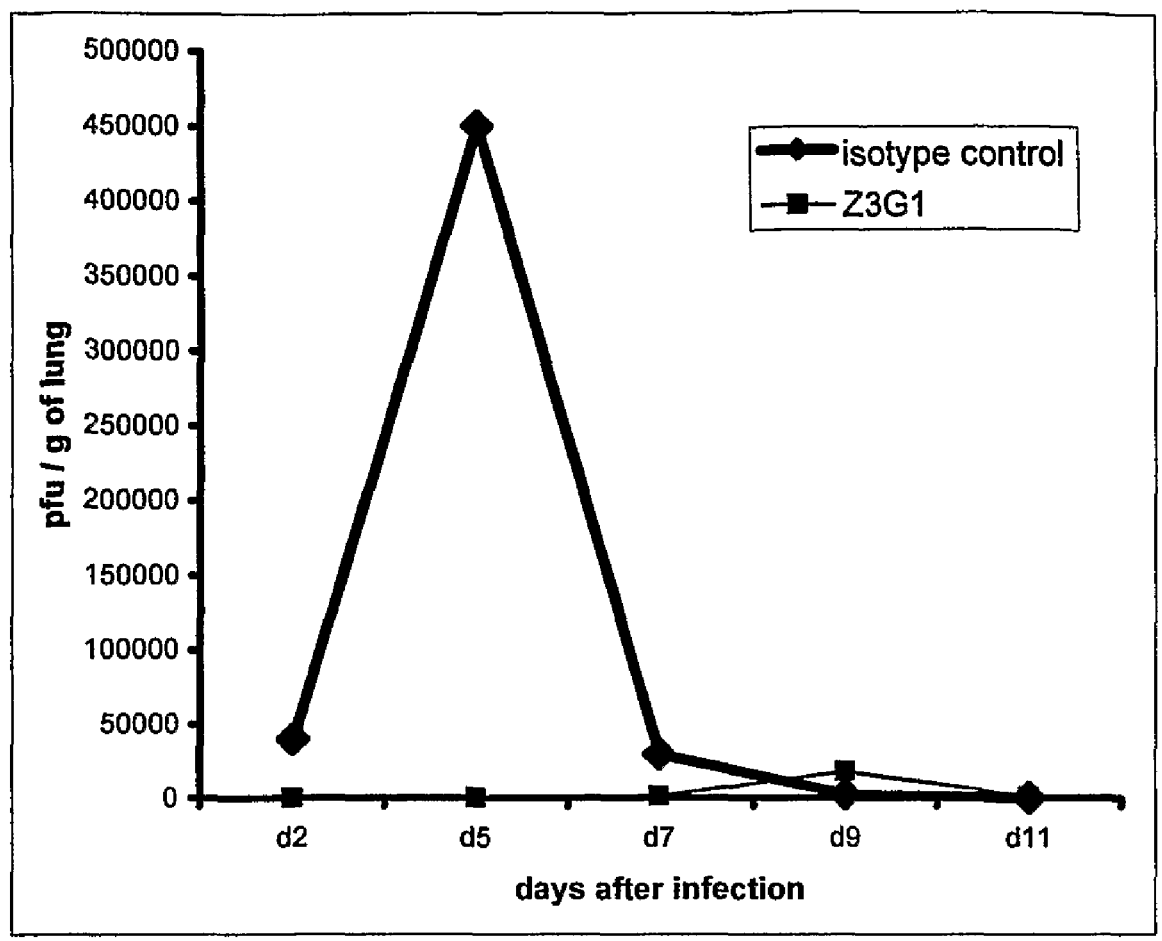
FIG. 3 shows prophylactic effect of administration of M2 antibody Z3G1 on the inhibition of virus replication in the lung of infected animals. Z3G1 or HSA (isotype control) was administered at 30 μg/mouse 1 day before a sub-lethal dose of A/HK1/68. Lung virus titer was measured by a plaque assay at the indicated time points.

The results in FIG. 3 indicate that at 2 days post infection no virus was detectable in mice treated with Z3G1. In contrast, $3.95\times10^4$ pfu/g virus in lungs was observed at 2 days post infection in isotype control (HSA) treated mice. At 5 days post infection, virus was present at 212 pfu/g of lungs in Z3G1 treated mice. In contrast, virus titer increased to $45\times10^4$ pfu/g of lungs at 5 days post infection in control (HSA) treated mice. Thus, Z3G1 treatment resulted in an about 1,000 to 10,000-fold reduction of virus titer. At 7 days post infection, virus titer dropped and at 11 days post infection, virus was virtually cleared likely due to host adaptive immunity-based clearance of the virus. The data demonstrates that anti-M2 antibody Z3G1 effectively inhibits influenza virus replication in vivo.

Example 5

This example describes studies indicating that M2 monoclonal antibodies of the invention have complement dependent cytotoxicity and antibody-dependent cell-mediated cytotoxicity.

Complement Dependent Cytotoxicity (CDC) Activity of Anti-M2 Antibodies:

Since M2 protein is highly expressed on infected cell surface, one of the mechanisms for anti-M2 antibody to protect a host from influenza A infection is to activate complement, which enhances opsonization and lyses infected cells thereby killing virus and preventing virus propagation in vivo. Anti-M2 antibodies were therefore studied for Complement Dependent Cytotoxicity on influenza A virus infected cells in vitro.

MDCK cells were plated in a 96-well flat bottom plate (Falcon®) at $2.5\times10^5$ cells per mL and 150 µl per well in complete minimal Essential Media (cMEM) containing 20 mM L-Glutamine, 10 mM Sodium Pyruvate, 1000 Units/mL Pen-Strep, MEM Vitamin Solution, MEM Eagle Non-essential amino acids (Invitrogen, Carlsbad, Calif.) supplemented with 10% fetal bovine serum (FBS) and cultured for 24 hr at 7% $CO_2$, 37° C. After 24 hr, the plate was washed twice with PBS and infected at room temperature for 30 minutes with 30 µl/well of 10-fold TCID50 influenza A virus (A/PR/8/34; ATCC, Rockville, Md.) with periodic swirling. After infection, the plate was washed once with PBS and 150 µl of 1 µg/mL trypsin (TPCK-treated, Worthington, Biochem. Corp.) in cMEM was added and the plate was incubated for 26 hr at 7% $CO_2$, 37° C. Cell monolayers were then washed with minimal essential media (MEM) three times. Antibodies were diluted at the desired concentration in blocking buffer (the same buffer used for cell based ELISA) and 50 µl added to each well and incubated at room temperature for 30 min. Following incubation, wells were washed with MEM once. 100 µL of Low Tox M Rabbit Complements (Cedarlane Lab Limited—Accurate, Hornby, Ontario, CANADA) reconstituted in 1 mL of MEM and further diluted to 1:10 was then added to cells. After 1 hour incubation at 37° C., the cell monolayer was washed with MEM three times, and the number of viable cells determined using CellTiter 96® $AQ_{ueous}$ one solution Cell Proliferation assay (Promega, Madison, Wis.) following the manufacturer's instructions. The greater the numbers of viable cells, the higher the optical density at 495 nm.

Figure 4:
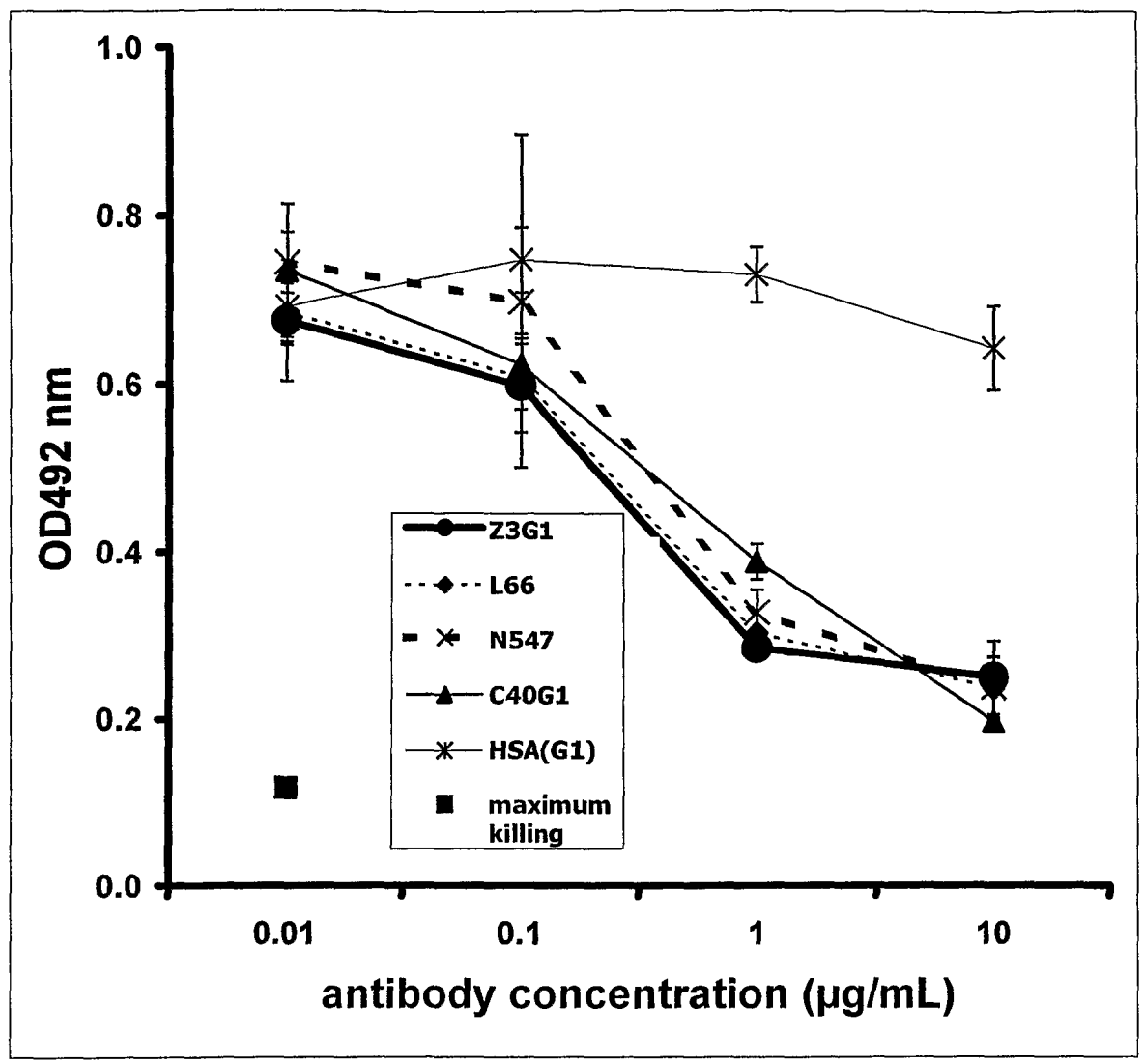
FIG. 4 shows complement dependent cytotoxicity (CDC) activity of anti-M2 antibodies Z3G1, L66, N547 and C40G1 compared to a control antibody (HSA).
Figure 5:
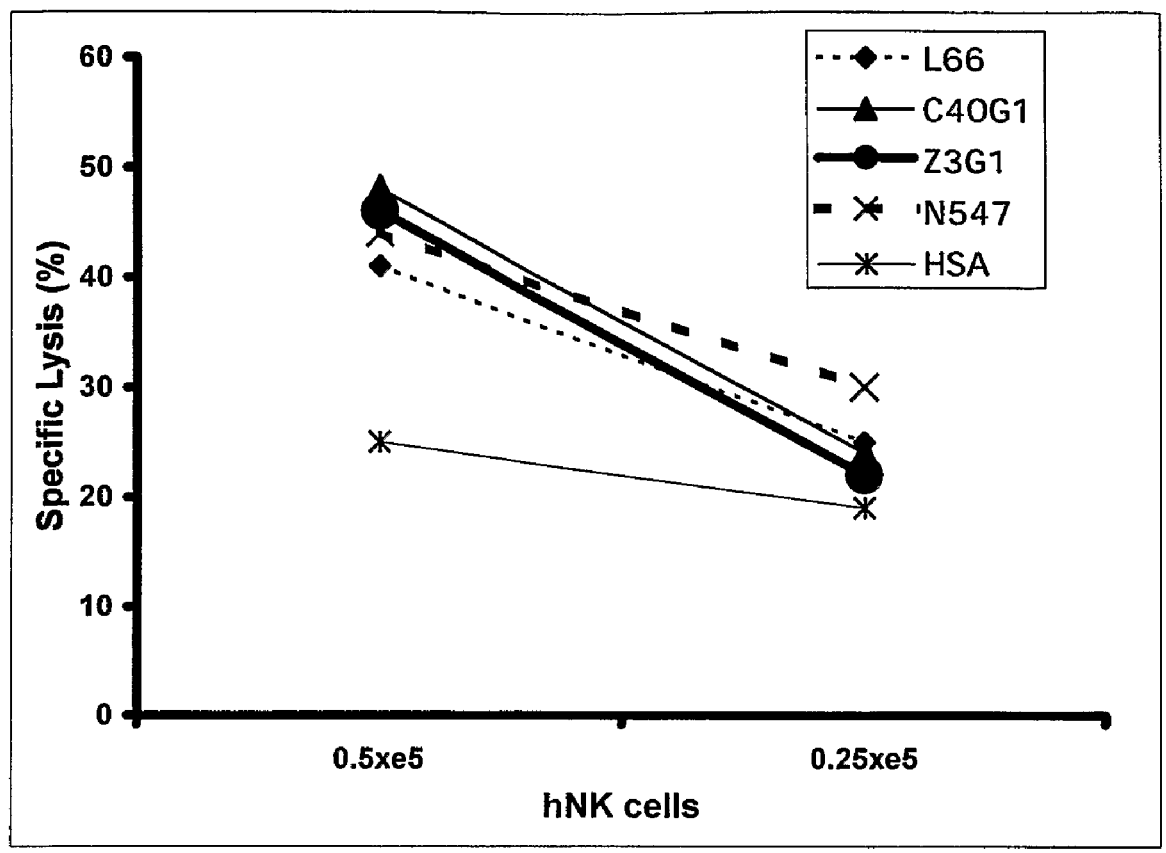
FIG. 5 shows antibody-dependent cell-mediated cytotoxicity (ADCC) activity of anti-M2 antibodies Z3G1, L66, N547 and C40G1 compared to a control antibody (HSA).

As shown in FIG. 4, the optical density, when cells were lysed by detergent (Triton X-100), was below 0.2. This was regarded as positive control showing maximum killing. The isotype control human antibody (HSA) could not lyse influenza A virus infected MDCK cells at any concentration. In contrast, all human anti-M2 antibodies in the study (Z3G1, L66, N547 and C40G1) lysed virus infected MDCK cell in a dose dependent manner. All antibodies lysed cells at 1 µg/mL, and the lysing effect close to maximum killing was observed at 10 µg/mL dose.

Antibody-Dependent Cell-Mediated Cytotoxicity (ADCC) Activity of Anti-M2 Antibodies:

Influenza A virus infected cells bound by anti-M2 antibody can be killed by a specialized non-T, non-B lymphoid cell called a natural killer cell (NK cell). The destruction of antibody-bound target cells by NK cells is called antibody-dependent cell-mediated cytotoxicity (ADCC), and is another mechanism by which anti-M2 antibody can protect a host from influenza A viral infection MDCK cells were plated in a 96-well flat bottom plate (Falcon®) at $0.25\times10^5$ cells/mL of cMEM with 10% FBS and 150 µl per well and cultured for 24 hr at 7% $CO_2$, 37° C. After 24 hr, the plate was washed twice with PBS and infected at room temperature for 30 minutes with 30 µl/well of 10-fold TCID50 influenza A virus (A/PR/8/34; ATCC, Rockville, Md.) with periodic swirling. After infection, the plate was washed once with PBS and 150 µl of 1 µg/mL trypsin (TPCK-treated, Worthington, Biochem. Corp.) in cMEM was added and the plate incubated for 22 hour at 7% $CO_2$, 37° C. Cell monolayers were then washed with blocking buffer three times. Antibodies were added at 5 µg/mL in blocking buffer, 50 µL/well, and incubated at room temperature for 30 min. Following incubation, wells were washed once with blocking buffer, and NK cells from normal human peripheral blood were purified using the MACS purification system (Miltenyi Biotec, Inc., Auburn, Calif.) according to the manufacturer's instructions. NK cells pre-incubated with 200 ng/mL of human IL-2 in 10% low Ig FCS containing RPMI 1640 (no phenol red) (Invitrogen, Carlsbad, Calif.) were added to the wells at different cell numbers. Cell lysis was determined by CytoTox 96® Non-Radioactive Cytotoxicity Assay system (Promega, Madison, Wis.) according to the manufacturer's instructions.

All human anti-M2 antibodies in the study, Z3G1, L66, N547 and C40G1, can lyse about 50% of virus infected MDCK cells when $0.5\times10^5$ NK cell were present. In contrast, only 25% lysis was observed with IgG1 isotype control antibody (HSA). Note that this 25% of non-antibody-coated target cell lysis in control group was observed because activated NK cells can lyse virus infected cells and non-self cells such as MDCK cell. Nevertheless, the lysis can be enhanced to 50% when target cells bind to anti-M2 antibody. Thus, all four human anti-M2 antibodies had ADCC activity.

Example 6

This example includes studies demonstrating the prophylactic and therapeutic activity of anti-M2 human monoclonal antibody Z3G1. This example also includes studies indicating little if any toxicity anti-M2 human monoclonal antibody Z3G1 in monkeys.

In Vivo Prophylactic Effect of the Anti M2 Human Monoclonal Antibody, Z3G1 on Influenza A Virus Infection in NK Cell Depleted (Immunocompromised) Animal NK cell depletion: In order to deplete NK cells, C57BL/6J mice were treated with 100 µg of PK136 (ATCC, Manassas, Va.), a mouse monoclonal IgG2a antibody to NK1.1 antigen, which is known to be specifically expressed in NK cells. An isotype matched antibody (clone C44, ATCC) was used as a control. The antibodies were given 2 and 5 days before and 1 and 4 days after infection. After three injections of anti NK1.1 antibody or control antibody, one mouse from each group was sacrificed, and lymph nodes, spleen and peripheral blood were collected. Single cell suspensions were prepared after lysis of red blood cells by Red Blood Cell lysing buffer (Sigma, St Louis, Mo.) and stained with DX5 FITC and CD3 PE (eBioscience, San Diego, Calif.) or the appropriate isotype control on ice for 45 minutes after blocking with anti-Fc receptor antibody (clone 2.4G2 from eBioscience) for 20 minutes. After washing two times with PBS containing 2% FCS, 10 mM EDTA, 0.05% NaN$_3$, and once with PBS, cells were fixed with 4% paraformaldehyde for 30 minutes and then analyzed by Flow Cytometry. DX5 is an NK cell marker in mice. Percentage of NK cells present in each tissue was calculated based on the number of DX5 positive cells among the total number of cells in the suspension.

Anti M2 antibody treatment of influenza A infection in NK cell depleted mouse: Anti-M2 antibody Z3G1 was administered at a dose of 100 μg/mouse intraperitoneally one day before the viral infection. As a control, an isotype matched human monoclonal anti human serum albumin (HSA) IgG1 antibody was administered at 100 μg/mouse. For the viral infection, mice were anesthetized with 15 μL/g of Avertin (1:1 w/v of 2,2,2 tribromoethanol and tert amyl alcohol, Sigma, St. Louis, Mo.), and were administered intranasally 30 μL of a lethal dose (3.2 fold of MLD50) of influenza A/HK/1/68 (CDC, Atlanta, Ga.). Mice were then observed daily for 23 days for survival.

As shown in Table 9 below, the percentages of NK cells were reduced in all three tissues analyzed in the mouse treated with the anti NK1.1 antibody compared to the mouse treated with the isotype control antibody. DX5 positive cells that represented NK cells were reduced from 0.93% to 0.02% in the lymph node, from 1.74% to 0.52% in the spleen and from 3.45% to 0.75% in the peripheral blood. These results showed that NK cells were efficiently depleted by the treatment with the anti NK1.1 antibody.

TABLE 9

Percentage of DX5+ cells in the mouse treated with the anti NK1.1 antibody and the mouse with the isotype control antibody.

|  | Lymph node (%) | Spleen (%) | Peripheral blood (%) |
| --- | --- | --- | --- |
| isotype control antibody treated mouse | 0.93 | 1.74 | 3.45 |
| anti-NK1.1 antibody treated mouse | 0.02 | 0.52 | 0.75 |

Protective Effect of the Anti M2 Antibody, Z3G1, on the Influenza a Infection in NK Depleted Mice Anti-M2 antibody, Z3G1, at 100 μg/mouse, protected mice from A/HK/1/68 infection in either NK cell depleted (Z3G1/NK−) or non depleted (Z3G1NK+) condition; whereas isotype control anti HSA antibody did not protect mice from the virus infection regardless whether NK cells were depleted or not (FIG. 6; HSA/NK− and HSA/NK+). In Z3G1/NK− and Z3G1/NK+ groups, 6 of 7 and 6 of 8 mice respectively, survived over the 23 day period of observation. No statistical difference was observed between these two groups (p>0.05, by Kaplan Meier survival analysis). In contrast, 1 of 8 and 0 of 8 mice were alive in HSA/NK- and HSA/NK+ groups respectively. The change in time course of the survival of infected mice between Z3G1 treated and anti-HSA treated groups were statistically significant in both NK depleted and non depleted condition (p<0.001).

Reports on the effect of a vaccine composed of M2 extracellular portion coupled to HBc (hepatitis B core particle) named M2 HBc have been reported (Jegerlehner, et al., *J. Immunol.* 172:5598 (2004)). These authors report the diminished vaccine effect on the infection in the NK cells depleted condition. Furthermore, these authors report that passive transfer of the serum obtained from vaccinated mice with the M2-HBc did not protect mice from a lethal challenge of influenza A when NK cells were depleted. These results indicate that the protective effect of M2-HBc vaccine on the influenza A infection was mainly mediated by NK cells. In contrast, anti-M2 antibody Z3G1 effectively protected mice from a lethal influenza A challenge even in the NK cell depleted condition. These results indicate that anti-M2 human monoclonal antibody Z3G1 can be effective in immunocompromised subjects, such as cancer patients where NK cell function may be impaired. These results also indicate that passive immunotherapy with anti-M2 antibody Z3G1 may offer a superior protection against influenza A infection compared to the vaccine.

Therapeutic Effect of Anti M2 Antibody, Z3G1, on Influenza A Infection in Mice

Anesthetized mice (15 μL/g of Avertin (1:1 w/v of 2,2,2 tribromoethanol and tert amyl alcohol)) (Sigma, St. Louis, Mo.) were infected intranasally with 30 μL (3.2 fold of MLD50) of a lethal dose of influenza A/HK/1/68 (CDC, Atlanta, Ga.). Z3G1 was administered at doses of 200, 100 and 30 μg/mouse intraperitoneally to female C57BL/6J mice (6~8 weeks old) one day after viral infection. As a control, an isotype matched human monoclonal anti HSA IgG1 antibody was administered at 200 μg/mouse. Mice were observed daily for 23 days for survival.

Data are shown in FIG. 7. In the control anti-HSA IgG1 group, 7 of 8 mice died by day 11 post infection. In contrast, 7 out of 8 mice survived in the group treated with 200 μg/mouse Z3G1 by day 11 post infection, and 4 of 8 mice were alive at day 23. Changes in time course of the survival rate between the control group and 200 μg/mouse of Z3G1 treated groups were statistically significant (p<0.02, by Kaplan Meyer survival analysis). At a dose of 100 μg/mouse, 7 out of 8 and 3 out of 8 mice were alive at days 11 and 23, respectively, but this difference was not statistically significant compared to the control group (p=0.068). At a dose of 30 μg/mouse, 3 out of 8 and 1 out of 8 mice were alive at days 11 and 23, respectively, and no protection was seen in treated group compared to the control group. These results indicate that anti-M2 antibody Z3G1 has a therapeutic effect on influenza A infection even when antibody is administered after influenza infection.

Toxicity Study of a Single Dose of Z3G1 in Cynomolgus Monkeys:

In order to evaluate toxicity of Z3G1, the antibody was administered by intravenous infusion over approximately 45 minutes with a single dose at 30 mg/kg to two cynomolgus monkeys. Animals were studied for three weeks after which they were necropsied. As a control, the vehicle, PBS was given to two monkeys. Treatment with 30 mg/kg of Z3G1 did not meaningfully change clinical observations, such as food consumption and body weight compared to control group. The antibody did not have a specific effect on hematologic parameters and serum chemistry, indicating that there was no meaningful change in clinical pathology as well. Taken together, a single intravenous treatment with 30 mg/kg of Z3G1 to cynomolgus monkeys did not show any noticeable toxicity based on the parameters tested such as serum chemistry, hematology, food consumption, body weight, gross pathology or histopathology. It appears that Z3G1 is well tolerated.

What is claimed:

1. An isolated antibody that specifically binds to an epitope in influenza A virus protein M2 extracellular domain, wherein the antibody comprises the heavy chain and light chain variable region sequences of the antibody produced by the CHO cell line deposited as ATCC PTA-5967.

2. The antibody of claim 1, wherein the antibody binds to an epitope within the amino acid sequence LLTEVETPIR (SEQ ID NO:1).

3. The antibody of claim 1, wherein a minimal binding sequence for antibody binding is LLTEVETPIR (SEQ ID NO:1).

4. The antibody of claim 1, wherein the extracellular domain comprises a sequence selected from: SLLTEVETPIRNEWGCRCNDSSD; SLLTEVETPIRSEWGCRCNDSGD; SLLTEVETPIRNEWECRCNGSSD; SLPTEVETPIRNEWGCRCNDSSD; SLLTEVETPIRNEWGCRCNGSSD; SLLTEVDTLTRNGWGCRCSDSSD; SLLTEVETPIRKEWGCNCSDSSD; SLLTEVETLIRNGWGCRCSDSSD; SLLTEVETLTKNGWGCRCSDSSD; SLLTEVETPIRSEWGCRYNDSSD; SLLTEVETPTRNGWECKCSDSSD; SLLTEVETHTRNGWECKCSDSSD; SLLTEVKTPTRNGWECKCSDSSD; SLLTEVETLTRNGWGCRCSDSSD; SLLTEVETPTRDGWECKCSDSSD; SLLTEVETPTRNGWGCRCSDSSD; SLLTEVETPTRNGWECKCNDSSD; SLLTEVETLTRNGWECKCSDSSD; SLPTEVETPIRNEWGCRCNDSSD; SFLTEVETPIRNEWGCRCNGSSD; SLLTEVETPTRNGWECRCNDSSD; SLLTEVETPIRKGWECNCSDSSD; SLLTEVETPTRNEWECRCSDSSD; SLLTEVETPTRNEWECRCSDSSD (SEQ ID NO:s 2-24), respectively.

5. The antibody of claim 1, wherein the antibody has detectable complement dependent cytotoxicity activity.

6. The antibody of claim 1, wherein the antibody has detectable antibody-dependent cell-mediated cytotoxicity activity.

7. The antibody of claim 1, wherein the antibody is selected from IgG, IgA, IgM, IgE, and IgD isotypes.

8. The antibody of claim 7, wherein the IgG isotype is selected from $IgG_1$, $IgG_2$, $IgG_3$ and $IgG_4$.

9. The antibody of claim 1, wherein the M2 extracellular domain consists of the amino acid sequence of SLLTEVETPIRNEWGCRCNDSSD (SEQ ID NO:2).

10. The antibody of claim 1, wherein the influenza A virus protein M2 is from a human or avian influenza A virus.

11. The antibody of claim 10, wherein the influenza virus is a strain, isolate or subtype selected from A/PR/8/34, A/HK/1/68, A/HK/156/97, H1N1, H2N2, H3N2, H5N1, H9N2, H2N1, H4N6, H6N2, H7N2, H7N3, H4N8, H5N2, H2N3, H11N9, H3N8, H1N2, H11N2, H7N7, H6N1, H13N6, H7N1, H11N1 and H5N3.

12. The antibody of claim 1, wherein the antibody comprises an antibody multimer.

13. A nucleic acid encoding the antibody produced by the CHO cell line deposited as ATCC Deposit No. PTA-5967.

14. The nucleic acid of claim 13, further comprising a vector.

15. A composition comprising the antibody of claim 1, and an antiviral agent.

16. A composition comprising the antibody of claim 1, and an agent that inhibits one or more symptoms or complications associated with influenza virus infection.

17. The composition of claim 16, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

18. A pharmaceutical composition comprising the antibody of claim 1, and a pharmaceutically acceptable carrier or excipient.

19. A kit comprising the antibody of claim 1, and instructions for treating, inhibiting or decreasing susceptibility of infection of a subject by one or more influenza virus strains or isolates.

20. The kit of claim 19, further comprising an article of manufacture for delivery of the antibody into a mucosal tissue.

21. The kit of claim 20, wherein the article of manufacture comprises an inhaler, aerosol, spray or squeeze bottle suitable for inhalation or nasal administration to a subject.

22. The kit of claim 20, wherein the mucosal tissue comprises nasal passages, sinuses, mouth, throat, larynx or lungs.

23. The kit of claim 19, further comprising an antiviral agent.

24. The kit of claim 19, further comprising an agent that inhibits one or more symptoms or complications associated with influenza virus infection.

25. A method for treating influenza virus infection of a subject, comprising administering to the subject an antibody or subsequence of claim 1 in an amount effective to treat influenza virus infection of the subject.

26. The method of claim 25, wherein the antibody is administered prior to, substantially contemporaneously with or following influenza virus infection of the subject.

27. The method of claim 25, wherein the subject is immunocompromised.

28. The method of claim 25, wherein the administration provides a therapeutic benefit.

29. The method of claim 28, wherein the therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject.

30. The method of claim 29, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

31. The method of claim 28, wherein the therapeutic benefit comprises hastening a subject's recovery from influenza virus infection.

32. The method of claim 25, wherein the influenza virus is from a human or avian host.

33. The method of claim 25, wherein the influenza virus is a strain, isolate or subtype selected from A/PR/8/34, A/HK/1/68, A/HK/156/97, H1N1, H2N2, H3N2, H5N1, H9N2, H2N1, H4N6, H6N2, H7N2, H7N3, H4N8, H5N2, H2N3, H11N9, H3N8, H1N2, H11N2, H7N7, H6N1, H13N6, H7N1, H11N1 and H5N3.

34. The method of claim 25, wherein the antibody binds to a minimal binding sequence that is LLTEVETPIR (SEQ ID NO: 1).

35. A method for inhibiting infection of a subject by one or more influenza virus strains or isolates comprising administering to the subject an antibody of claim 1 in an amount effective to inhibit infection of the subject by one or more influenza virus strains or isolates.

36. The method of claim 35, wherein the subject is not currently infected with influenza virus.

37. The method of claim 35, wherein the subject does not exhibit one or more symptoms or complications associated with influenza virus infection.

38. The method of claim 35, wherein the subject has been exposed to or contacted with influenza but does not exhibit one or more symptoms or complications associated with influenza virus infection.

39. The method of claim 35, wherein the antibody is administered prior to, substantially contemporaneously with or following influenza virus infection of the subject.

40. The method of claim 35, wherein the subject is immunocompromised.

41. The method of claim 35, wherein the administration provides a therapeutic.

42. The method of claim 35, wherein the influenza virus strain or isolate is human or avian.

43. The method of claim 35, wherein the influenza virus is a strain, isolate or subtype selected from A/PR/8/34, A/HK/1/68, A/HK/156/97, H1N1, H2N2, H3N2, H5N1, H9N2, H2N1, H4N6, H6N2, H7N2, H7N3, H4N8, H5N2, H2N3, H11N9, H3N8, H1N2, H11N2, H7N7, H6N1, H13N6, H7N1, H11N1 and H5N3.

44. The method of claim 35, wherein the antibody comprises a heavy-chain variable sequence encoded by SEQ ID NO:s 32 or 36 and a light-chain variable sequence encoded by SEQ ID NO: 33.

45. The method of claim 35, wherein the antibody comprises the heavy-chain variable sequence of SEQ ID NO:s 34 or 37 and the light-chain variable sequence of SEQ ID NO: 35.

46. An isolated nucleic acid that encodes the heavy-chain variable sequence as set forth in SEQ ID NO:s 34 or 37 or the light-chain variable sequence as set forth in SEQ ID NO: 35.

47. An isolated nucleic acid that encodes the heavy-chain variable and constant region, wherein the sequence comprises SEQ ID NO: 36 or the light-chain variable and constant region, wherein the sequence comprises SEQ ID NO: 33.

48. A method of producing the human M2 antibody of claim 1, comprising:
   a) providing a CHO cell line deposited as ATCC Deposit No. PTA-5967 that produces a human M2 antibody; and
   b) isolating an antibody from the CHO cell line.

49. The method of claim 48, wherein the minimal binding sequence for the human M2 antibody is LLTEVETPIR (SEQ ID NO: 1).

50. The antibody of claim 1, wherein the amino acid sequence of the heavy chain variable region comprises amino acids 20-137 of SEQ. ID NO:37, and wherein the amino acid sequence of the light chain variable region comprises amino acids 20-130 of SEQ ID NO:35.

51. The antibody of claim 50, wherein the amino acid sequence of the heavy chain constant region comprises amino acids 138-467 of SEQ ID NO:37, and wherein the amino acid sequence of the light chain constant region comprises amino acids 131-235 of SEQ ID NO:35.

52. An isolated antibody, comprising SEQ ID NO: 34 and SEQ ID NO: 35.

53. An isolated antibody, comprising SEQ ID NO: 37 and SEQ ID NO: 35.

54. An isolated host cell that expresses the antibody of claim 52.

55. An isolated host cell that expresses the antibody of claim 53.

56. The isolated host cell of claim 54 or 55, wherein the cell is a bacteria, a yeast, from a plant or from an animal.

* * * * *